US010894818B2

(12) United States Patent
Sasisekharan et al.

(10) Patent No.: US 10,894,818 B2
(45) Date of Patent: Jan. 19, 2021

(54) ANTIBODIES THAT BIND EBOLA GLYCOPROTEIN AND USES THEREOF

(71) Applicant: Massachusetts Institute of Technology, Cambridge, MA (US)

(72) Inventors: Ram Sasisekharan, Lexington, MA (US); Kannan Tharakaraman, Arlington, MA (US); Devin Quinlan, Cambridge, MA (US); Vidya Subramanian, Concord, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 282 days.

(21) Appl. No.: 15/515,746

(22) PCT Filed: Oct. 2, 2015

(86) PCT No.: PCT/US2015/053871
§ 371 (c)(1),
(2) Date: Mar. 30, 2017

(87) PCT Pub. No.: WO2016/054598
PCT Pub. Date: Apr. 7, 2016

(65) Prior Publication Data
US 2017/0298120 A1    Oct. 19, 2017

Related U.S. Application Data

(60) Provisional application No. 62/059,746, filed on Oct. 3, 2014.

(51) Int. Cl.
C07K 16/00       (2006.01)
A61K 39/00       (2006.01)
(Continued)

(52) U.S. Cl.
CPC ............ *C07K 16/10* (2013.01); *A61K 38/212* (2013.01); *A61K 39/42* (2013.01);
(Continued)

(58) Field of Classification Search
None
See application file for complete search history.

(56) References Cited

U.S. PATENT DOCUMENTS 4,439,196 A    3/1984  Higuchi
4,447,224 A    5/1984  DeCant, Jr. et al.
(Continued)

FOREIGN PATENT DOCUMENTS

CN    101137673 A    3/2008
CN    101287498 A    10/2008
(Continued)

OTHER PUBLICATIONS

Qiu et al. Characterization of Zaire ebolavirus glycoprotein-specific monoclonal antibodies. Clin. Immunol. 2011; 141: 218-227.*
(Continued)

*Primary Examiner* — Michelle S Horning
(74) *Attorney, Agent, or Firm* — Nelson Mullins Riley & Scarborough LLP; Amy E. Mandragouras, Esq.; Erika L. Wallace

(57) ABSTRACT

Isolated monoclonal antibodies which bind to Ebola virus glycoprotein and related antibody-based compositions and molecules are disclosed. Also disclosed are therapeutic and diagnostic methods for using the antibodies.

30 Claims, 6 Drawing Sheets

Specification includes a Sequence Listing.

(51) Int. Cl.
   *C07K 16/10* (2006.01)
   *A61K 38/21* (2006.01)
   *A61K 39/42* (2006.01)
(52) U.S. Cl.
   CPC .... *A61K 2039/505* (2013.01); *C07K 2317/21* (2013.01); *C07K 2317/34* (2013.01); *C07K 2317/50* (2013.01); *C07K 2317/56* (2013.01); *C07K 2317/565* (2013.01); *C07K 2317/567* (2013.01); *C07K 2317/732* (2013.01); *C07K 2317/734* (2013.01); *C07K 2317/76* (2013.01); *C07K 2317/92* (2013.01); *C12N 2760/14122* (2013.01)

(56) References Cited

U.S. PATENT DOCUMENTS

| | | |
|---|---|---|
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,704,362 A | 11/1987 | Itakura et al. |
| 4,790,824 A | 12/1988 | Morrow et al. |
| 4,941,880 A | 7/1990 | Burns |
| 5,064,413 A | 11/1991 | McKinnon et al. |
| 5,223,409 A | 6/1993 | Ladner et al. |
| 5,225,539 A | 7/1993 | Winter |
| 5,304,489 A | 4/1994 | Rosen |
| 5,312,335 A | 5/1994 | McKinnon et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,403,484 A | 4/1995 | Ladner et al. |
| 5,427,908 A | 6/1995 | Dower et al. |
| 5,476,996 A | 12/1995 | Wilson et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,677,425 A | 10/1997 | Bodmer et al. |
| 5,693,761 A | 12/1997 | Queen et al. |
| 5,693,762 A | 12/1997 | Queen et al. |
| 5,698,767 A | 12/1997 | Wilson et al. |
| 5,714,350 A | 2/1998 | Co et al. |
| 5,741,957 A | 4/1998 | Deboer et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,849,992 A | 12/1998 | Meade et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,172,197 B1 | 1/2001 | McCafferty et al. |
| 6,350,861 B1 | 2/2002 | Co et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,630,144 B1 | 10/2003 | Hart et al. |
| 7,335,356 B2 | 2/2008 | Hart et al. |
| 8,513,391 B2 | 8/2013 | Jones et al. |
| 2004/0014194 A1 | 1/2004 | Beyer et al. |
| 2004/0110704 A1 | 6/2004 | Yamane et al. |
| 2010/0069614 A1 | 3/2010 | Houtzager et al. |
| 2012/0070861 A1 | 3/2012 | Macdonald et al. |
| 2012/0073004 A1 | 3/2012 | MacDonald et al. |

FOREIGN PATENT DOCUMENTS

| | | |
|---|---|---|
| EP | 0154316 A2 | 9/1985 |
| EP | 338 841 A1 | 10/1989 |
| EP | 0401384 A1 | 12/1990 |
| EP | 1176195 A1 | 1/2002 |
| WO | 87/02671 A1 | 5/1987 |
| WO | 87/04462 A1 | 7/1987 |
| WO | 89/01036 A1 | 2/1989 |
| WO | 90/07861 A1 | 7/1990 |
| WO | 9203918 A1 | 3/1992 |
| WO | 92/22645 A1 | 12/1992 |
| WO | 92/22653 A1 | 12/1992 |
| WO | 93/01227 A1 | 1/1993 |
| WO | 94/25585 A1 | 11/1994 |
| WO | 98/24884 A1 | 6/1998 |
| WO | 99/54342 A1 | 10/1999 |
| WO | 0243478 A2 | 6/2002 |
| WO | 03/035835 A2 | 5/2003 |
| WO | 2004/018649 A2 | 3/2004 |
| WO | 2005/044853 A2 | 5/2005 |
| WO | 06/089231 A2 | 8/2006 |
| WO | 2009/15777 A1 | 2/2009 |
| WO | 2009/094755 A1 | 8/2009 |
| WO | 2010/080538 A1 | 7/2010 |
| WO | 2011/071574 A2 | 6/2011 |
| WO | 2011/072204 A1 | 6/2011 |
| WO | 2011/097603 A1 | 8/2011 |
| WO | 2011/163311 A1 | 12/2011 |
| WO | 2011/163314 A1 | 12/2011 |
| WO | 2012148873 A2 | 11/2012 |
| WO | 2015187885 A1 | 12/2015 |

OTHER PUBLICATIONS

Rudikoff et.al., Single amino acid substitution altering antigen-binding specificity. PNAS 1982; 79: 1979-1983.*
Panka et.al., Variable region framework differences result in decreased or increased affinity of variant anti-digoxin antibodies. PNAS , 1985; 85: 3080-3084.*
International Preliminary Report on Patentability, PCT/US2015/053871, dated Apr. 4, 2017, 14 pages.
International Search Report and Written Opinion, PCT/US2015/053871, dated Mar. 31, 2016, 23 pages.
Martinez, O. et al., "Impact of Ebola Mucin-Like Domain on Antiglycoprotein Antibody Responses Induced by Ebola Virus-Like Particles", Journal of Infectious Diseases, JID., vol. 204 (suppl 3):S825-S832 (2011).

Qiu, X. et al., "Ebola GP-Specific Monoclonal Antibodies Protect Mice and Guinea Pigs from Lethal Ebola Virus Infection," Plos Neglected Tropical Diseases, vol. 6(3):e1575 (2012).

Qiu, X. et al., "Characterization of Zaire of glycoprotein-specific monoclonal antibodies," Clinical Immunology, Academic Press, US, vol. 141(2): 218-227(2011).

Qiu, X. et al., "Successful Treatment of Ebola Virus-Infected Cynomolgus Macaques with Monoclonal Antibodies," Science Translation Medicine,vol. 4 (138): 1-11(2012).

Shedlock D J. et al., "Antibody-mediated neutralization of Ebola virus can occur by two distinct mechanisms," Virology, vol. 401 (2):228-235:(2010).

Qui, X. et al., "mAbs and Ad-vectored IFN-a therapy rescue Ebola-infected nonhuman primates when administered after the detection of viremia and symptoms," Sci Transl Med. vol. 5(207): 12 pages (2013).

Qui, X. et al., "Reversion of advanced Ebola virus disease in nonhuman primates with ZMapp," Nature, vol. 514 (7520):47-53 (2014).

(56) References Cited

OTHER PUBLICATIONS

Ding Guoyong et al., Advances in the study of envelope glycoprotein of Ebola Virus," Journal of virus," vol. 29 (Issue 2): 5 pages (2013).

* cited by examiner

Figure 2

\> ZEBOV 2014 GP

MGVTGILQLPRDRFKRTSFFLWVIILFQRTFSIPLGVIHNSTLQVSDVDKLVCR
DKLSSTNQLRSVGLNLEGNGVATDVPSVTKRWGFRSGVPPKVVNYEAGEWAENC
YNLEIKKPDGSECLPAAPDGIRGFPRCRYVHKVSGTGPCAGDFAFHKEGAFFLY
DRLASTVIYRGTTFAEGVVAFLILPQAKKDFFSSHPLREPVNATEDPSSGYYST
TIRYQATGFGTNETEYLFEVDNLTYVQLESRFTPQFLLQLNETIYASGKRSNTT
GKLIWKVNPEIDTTIGEWAFWETKKNLTRKIRSEELSFTAVSNGPKNISGQSPA
RTSSDPETNTTNEDHKIMASENSSAMVQVHSQGRKAAVSHLTTLATISTSPQPP
TTKTGPDNSTHNTPVYKLDISEATQVGQHHRRADNDSTASDTPPATTAAGPLKA
ENTNTSKSADSLDLATTSPQNYSETAGNNNTHHQDTGEESASSGKLGLITNTI
AGVAGLITGGRRTRREVIVNAQPKC**NPNLHYWTTQDEGAAIGLAWIPYFGPAAE
GIYTEGLMHNQDGLICGLRQLANETTQALQLFLRATTELRFTFSILNRKAIDFLL
QRWGGTCHILGPDCCIEPHDWTKNITDKIDQIIHDFVDKTLPDQGDNDNWWTGW
RQWIPAGIGVTGVIIAVIALFCICKFVF (SEQ ID NO: 91)

■ GP1 AMINO ACIDS     ■ GP2 AMINO ACIDS

Figure 5

| Antibody | Neutralising titre (PRNT80) | | |
| --- | --- | --- | --- |
| | Mayinga 1976 strain | Kikwit 1995 strain | Makona 2014 strain |
| *13C6.1* | >50 μg/mL | >50 μg/mL | >50 μg/mL |
| *2G4.6* | 2 μg/mL | 4 μg/mL | 2 μg/mL |
| *4G7.9* | 1 μg/mL | 1 μg/mL | 1 μg/mL |

ANTIBODIES THAT BIND EBOLA GLYCOPROTEIN AND USES THEREOF

RELATED APPLICATIONS

This application is a 35 U.S.C. 371 national stage filing of International Application PCT/US2015/053871, filed on Oct. 2, 2015, which claims the priority benefit of U.S. Provisional Application 62/059,746 filed on Oct. 3, 2014. The entire contents of these applications are incorporated herein by reference in their entirety.

GOVERNMENT FUNDING

This invention was made with Government support under Grant Nos. R01 AI111395 and R37 GM057073 awarded by the National Institutes of Health. The Government has certain rights in the invention.

REFERENCE TO THE SEQUENCE LISTING

The instant application contains a Sequence Listing which has been submitted electronically in ASCII format and is hereby incorporated by reference in its entirety. Said ASCII copy, created on Mar. 30, 2017, is named MITN_030US_SL.txt and is 73501 bytes in size.

BACKGROUND

Ebola virus (EBOV) is a virulent pathogen which causes severe hemorrhagic fever in humans with a fatality rate of 50-90%. The acute form of the illness (approximately 3-5 weeks from contraction to death) means that there is little opportunity to develop an adaptive immunity. There is an urgent need for effective counter measures as there are no approved vaccines or therapies against EBOV.

The EBOV glycoprotein (GP) is the predominant surface protein expressed by the virus. The GP protein is responsible for two main functions: (1) viral entry into host cells and (2) catalysis of membrane fusion. Mice experiments have demonstrated that EBOV GP is the main target of neutralizing antibodies. Additionally, animal studies have shown that such antibodies have prophylactic and therapeutic potential in non-human primates, which mimic important aspects of EBOV infection in humans. However, mutations in the Ebola virus glycoprotein may affect the efficacy of current vaccines or antibody treatments. Therefore, new antibody-based agents and vaccines against EBOV GP provide a promising option for combating EBOV outbreaks in humans.

SUMMARY

The invention described herein pertains to monoclonal antibodies and antigen binding portions thereof directed towards Ebola virus glycoprotein (GP), which have desirable functional properties. These properties include high affinity binding to Ebola virus GP and neutralizing activity against the Zaire Ebola Virus, including the Makona 2014 strain. As described herein, the present invention identifies regions within Ebola virus GP that serve as specific neutralization epitopes for the monoclonal antibodies of the invention. These epitopes also serve to provide fragments of Ebola virus GP that are useful for eliciting an active and specific immune response against Ebola virus GP, both in vitro, e.g., for detection of GP, and in vivo, for inducing a protective immune response in subjects in need thereof. The epitopes are useful in vaccine compositions as immunogens for eliciting an anti-Ebola virus GP immune response in subjects. Also provided herein are methods for treating Ebola virus infection in patients in need thereof as well as methods of detecting Ebola virus in a sample.

In one aspect, provided herein are isolated monoclonal antibodies, or antigen binding portions thereof, which binds to Ebola virus glycoprotein, wherein the monoclonal antibody is selected from the group consisting of:

(a) a monoclonal antibody 4G7.9 comprising a variable heavy chain and a variable light chain set forth in SEQ ID NOs: 39 and 14;

(b) a monoclonal antibody 2G4.6 comprising a variable heavy chain and a variable light chain set forth in SEQ ID NOs: 32 and 37; and (c) a monoclonal antibody 13C6.1 comprising a variable heavy chain and a variable light chain set forth in SEQ ID NOs: 15 and 17.

In some aspects, the invention relates to a monoclonal antibody 4G7.9, or antigen binding portion thereof. In other aspects, the invention relates to a monoclonal antibody 2G4.6, or antigen binding portion thereof. Yet other aspects of the invention relate to a monoclonal antibody 13C6.1, or antigen binding portion thereof.

In one aspect, provided herein are pharmaceutical compositions comprising a combination of monoclonal antibodies or antigen binding portions thereof, which bind to Ebola virus glycoprotein, and a pharmaceutically acceptable carrier, wherein the combination of monoclonal antibodies is selected from the group consisting of:

(a) monoclonal antibody 4G7.9 comprising a variable heavy chain and a variable light chain set forth in SEQ ID NOs: 39 and 14 and monoclonal antibody 2G4.6 comprising a variable heavy chain and a variable light chain set forth in SEQ ID NOs: 32 and 37, and optionally, monoclonal antibody 13C6.1 comprising a variable heavy chain and a variable light chain set forth in SEQ ID NOs: 15 and 17;

(b) monoclonal antibody 4G7.9 comprising a variable heavy chain and a variable light chain set forth in SEQ ID NOs: 39 and 14 and monoclonal antibody 13C6.1 comprising a variable heavy chain and a variable light chain set forth in SEQ ID NOs: 15 and 17, and optionally monoclonal antibody 2G4.6 comprising a variable heavy chain and a variable light chain set forth in SEQ ID NOs: 32 and 37; and (c) monoclonal antibody 13C6.1 comprising a variable heavy chain and a variable light chain set forth in SEQ ID NOs: 15 and 17, and optionally monoclonal antibody 2G4.6 comprising a variable heavy chain and a variable light chain set forth in SEQ ID NOs: 32 and 37, and optionally, monoclonal antibody 4G7.9 comprising a variable heavy chain and a variable light chain set forth in SEQ ID NOs: 39 and 14.

In some aspects, the invention relates to a pharmaceutical composition comprising monoclonal antibodies 4G7.9, 2G4.6 and 13C6.1, and a pharmaceutically acceptable carrier.

Another aspect of the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and b) a light chain comprising CDR1, CDR2, and CDR3 sequences set forth in SEQ ID NOs: 87, 88, and 89 respectively, wherein the remainder of the light chain is from a human immunoglobulin.

Another aspect of the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 74, 75, and 76, respectively, and variable region framework residues selected from the group consisting of 49H, 50H, or a combination thereof (Kabat numbering convention) from the heavy chain variable region set forth in SEQ ID NO: 94, wherein the remainder of the heavy chain is from a human immunoglobulin; and b) a light chain comprising CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In another aspect, the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 45, 46, and 47, respectively, wherein the remainder of the heavy chain is from a human immunoglobulin; and b) a light chain comprising CDR1, CDR2, and CDR3 sequences set forth in SEQ ID NOs: 48, 50, and 51, respectively, wherein the remainder of the light chain is from a human immunoglobulin.

Another aspect of the invention relates to an isolated monoclonal antibody, or antigen binding portion thereof, which binds to Ebola virus glycoprotein, and comprises a heavy chain variable region and light chain variable region comprising an amino acid sequence at least 90% identical to the amino acid sequences selected from the group consisting of:

(a) SEQ ID NOs: 15 and 17, respectively;
(b) SEQ ID NOs: 32 and 37, respectively; and
(c) SEQ IS NOs: 39 and 14, respectively;

wherein the monoclonal antibody is a neutralizing antibody and specifically binds to Ebola virus glycoprotein with an $EC_{50}$ of 200 pM or less, as measured by ELISA.

Another aspect of the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, wherein the remainder of the heavy chain is from a human immunoglobulin; and b) a light chain comprising CDR1, CDR2, and CDR3 sequences set forth in SEQ ID NOs: 87, 88, and 89 respectively, wherein the remainder of the light chain is from a human immunoglobulin.

In another aspect, the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, wherein the remainder of the heavy chain is from a human immunoglobulin; and b) a light chain comprising CDR1, CDR2, and CDR3 sequences set forth in SEQ ID NOs: 87, 88, and 89, respectively, and variable region framework residues selected from the group consisting of 43 L, 87 L, or a combination thereof (Kabat numbering convention) from the light chain variable region set forth in SEQ ID NO: 97, wherein the remainder of the light chain is from a human immunoglobulin.

In another aspect, the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, wherein the remainder of the heavy chain is from a human immunoglobulin; and b) a light chain comprising CDR1, CDR2, and CDR3 sequences set forth in SEQ ID NOs: 87, 88, and 89 respectively, and variable region framework residues selected from the group consisting of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

Another aspect of the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 74, 75, and 76, respectively, wherein the remainder of the heavy chain is from a human immunoglobulin; and b) a light chain comprising CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

Yet another aspect of the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and b) a light chain comprising CDR1, CDR2, and CDR3 sequences set forth in SEQ ID NOs: 87, 88, and 89 respectively, and variable region framework residues selected from the group consisting of 43 L, 87 L, or a combination thereof (Kabat numbering convention) from the light chain variable region set forth in SEQ ID NO: 97, wherein the remainder of the light chain is from a human immunoglobulin.

Another aspect of the inventions relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and b) a light chain comprising CDR1, CDR2, and CDR3 sequences set forth in SEQ ID NOs: 87, 88, and 89 respectively, and variable region framework residues selected from the group consisting of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

Another aspect of the invention relates to an isolated monoclonal antibody, or antigen binding portion thereof, which binds to Ebola virus glycoprotein, comprising:

a) a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and b) a light chain comprising CDR1, CDR2, and CDR3 sequences set forth in SEQ ID NOs: 87, 90, and 89 respectively, and variable region framework residues selected from the group consisting of 3 L, 43 L, 52 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

Another aspect of the invention relates to an isolated monoclonal antibody, or antigen binding portion thereof, which specifically binds to Ebola virus glycoprotein and competes for binding to Ebola virus glycoprotein with a monoclonal antibody selected from the group consisting of 13C6.1, 2G4.6, and 4G7.9, wherein the monoclonal antibody exhibits at least one (or more) of the following properties:

(a) binds to Ebola virus glycoprotein with an $EC_{50}$ of 200 pM or less, as measured by ELISA;

(b) binds to a conformational epitope on Ebola virus glycoprotein (SEQ ID NO: 91);

(c) binds within the region V505-C511 of Ebola virus glycoprotein (SEQ ID NO: 91);

(d) binds within the region N550-E564 of Ebola virus glycoprotein (SEQ ID NO: 91);

(e) binds within the region T270-P279 of Ebola virus glycoprotein (SEQ ID NO: 91);

(f) binds within the region Y394-R404 of Ebola virus glycoprotein (SEQ ID NO: 91); and (g) engages immune components such as antibody-dependent cellular cytotoxicity (ADCC) or complement-dependent cytotoxicity (CDC).

Some aspects of the invention relate to any of the preceding antibodies, or antigen binding portions thereof, which specifically bind to a conformational epitope on Ebola virus glycoprotein (SEQ ID NO: 91) that spans V505-C511 and N550-E564.

Some aspects of the invention relate to any of the preceding antibodies, or antigen binding portions thereof, which specifically binds to a conformational epitope on Ebola virus glycoprotein (SEQ ID NO: 91) that spans T270-P279 and Y394-R409.

In other aspects, the invention relates to an isolated monoclonal antibody, or antigen binding portion thereof, which specifically binds to Ebola virus glycoprotein, comprises a variable heavy chain and a variable light chain selected from the group consisting of:

(a) SEQ ID NOs: 15 and 17;
(b) SEQ ID NOs: 32 and 37;
(c) SEQ IS NOs: 39 and 14;
(d) SEQ ID NOs: 11 and 37;
(e) SEQ ID NOs: 13 and 14;
(f) SEQ ID NOs: 13 and 42;
(g) SEQ ID NOs: 13 and 43;
(h) SEQ ID NOs: 39 and 42;
(i) SEQ ID NOs: 39 and 43; and
(j) SEQ ID NOs: 39 and 44.

Some aspects of the invention relate to any of the preceding antibodies, or antigen binding portions thereof, having neutralizing activity against the Zaire Ebola Virus.

Some aspects of the invention relate to any of the preceding antibodies, or antigen binding portions thereof, which specifically bind to Ebola virus glycoprotein with an $EC_{50}$ of 200 pM or less, 150 pM or less, or 100 pM or less, as measured by ELISA. Some aspects of the invention relate to any of the preceding antibodies, or antigen binding portions thereof, which specifically bind to Ebola virus glycoprotein with an $EC_{50}$ of 150 pM or less, as measured by ELISA. Some aspects of the invention relate to any of the preceding antibodies, or antigen binding portions thereof, which specifically bind to Ebola virus glycoprotein with an $EC_{50}$ of 100 pM or less, as measured by ELISA.

One aspect of the invention relates to a monoclonal antibody 4G7.9 comprising a variable heavy chain and a variable light chain set forth in SEQ ID NOs: 39 and 14, which binds to V505-C511 and N550-E564 of Ebola virus glycoprotein (SEQ ID NO: 91). Other aspects of the invention relate to monoclonal antibodies 4G7.1, 4G7.2, 4G7.3, 4G7.10, 4G7.11, and 4G7.12, which bind within the region V505-C511 or within the region N550-E564, or both.

Yet other aspects of the invention relate to a monoclonal antibody 4G7.9 which binds to Ebola virus glycoprotein with an $EC_{50}$ of 200 pM or less, as measured by ELISA. Another aspect of the invention relates to a monoclonal antibody 4G7.9 which binds to Ebola virus glycoprotein with an $EC_{50}$ of 100 pM or less, as measured by ELISA. Other aspects of the invention relate to monoclonal antibody 4G7.9 which binds to Ebola virus glycoprotein with an $EC_{50}$ of 99.7 pM or less, as measured by ELISA. Other aspects of the invention relate to a monoclonal antibody 4G7.1 which binds to Ebola virus glycoprotein with an $EC_{50}$ of 200 pM or less, as measured by ELISA. Other aspects of the invention relate to a monoclonal antibody 4G7.1 which binds to Ebola virus glycoprotein with an $EC_{50}$ of 182 pM or less, as measured by ELISA. In other aspects, the invention relates to a monoclonal antibody 4G7.2 which binds to Ebola virus glycoprotein with an $EC_{50}$ of 200 pM or less, as measured by ELISA. Other aspects of the invention relate to a monoclonal antibody 4G7.2 which binds to Ebola virus glycoprotein with an $EC_{50}$ of 95.2 pM or less, as measured by ELISA. In other aspects, the invention relates to a monoclonal antibody 4G7.3 which binds to Ebola virus glycoprotein with an $EC_{50}$ of 200 pM or less, as measured by ELISA. Other aspects of the invention relate to a monoclonal antibody 4G7.3 which binds to Ebola virus glycoprotein with an $EC_{50}$ of 176 pM or less, as measured by ELISA. Other aspects of the invention relate to a monoclonal antibody 4G7.10 which binds to Ebola virus glycoprotein with an $EC_{50}$ of 200 pM or less, as measured by ELISA. Another aspect of the invention relates to monoclonal antibody 4G7.10 which binds to Ebola virus glycoprotein with an $EC_{50}$ of 120 pM or less, as measured by ELISA. Other aspects of the invention relate to a monoclonal antibody 4G7.11 which binds to Ebola virus glycoprotein with an $EC_{50}$ of 200 pM or less, as measured by ELISA. Another aspect of the invention relates to monoclonal antibody 4G7.11 which binds to Ebola virus glycoprotein with an $EC_{50}$ of 145 pM or less, as measured by ELISA. Other aspects of the invention relate to a monoclonal antibody 4G7.12 which binds to Ebola virus glycoprotein with an $EC_{50}$ of 200 pM or less, as measured by ELISA. Another aspect of the invention relates to monoclonal antibody 4G7.12 which binds to Ebola virus glycoprotein with an $EC_{50}$ of 88.8 pM or less, as measured by ELISA.

Yet other aspects of the invention relate to a monoclonal antibody 4G7.9 which has neutralizing activity against Zaire Ebola Virus. In one aspect, the invention relates to a monoclonal antibody 4G7.9 which neutralizes Ebola virus Mayinga 1976 strain at 1 μg/mL, as measured by a plaque reduction neutralization assay. In another aspect, the invention relates to a monoclonal antibody 4G7.9 which neutralizes Ebola virus Kikwit 1995 strain at 1 μg/mL, as measured by a plaque reduction neutralization assay. Another aspect of the invention relates to a monoclonal antibody 4G7.9 neutralizes Ebola virus Makon 2014 strain at 1 μg/mL, as measured by a plaque reduction neutralization assay.

Other aspects of the invention relate to a monoclonal antibody 4G7.9 comprising a variable heavy chain and a variable light chain set forth in SEQ ID NOs: 39 and 14, which engages immune components such as antibody-dependent cellular cytotoxicity (ADCC) or complement-dependent cytotoxicity (CDC). Yet other aspects of the invention relate to monoclonal antibodies 4G7.1, 4G7.2, 4G7.3, 4G7.10, 4G7.11, and 4G7.12, which engage immune components such as antibody-dependent cellular cytotoxicity (ADCC) or complement-dependent cytotoxicity (CDC).

In another aspect, the invention relates to an isolated monoclonal antibody, or antigen binding portion thereof, which specifically binds to Ebola virus glycoprotein and competes for binding to Ebola virus glycoprotein with a monoclonal antibody 4G7.9, wherein the monoclonal antibody exhibits at least one, two, three, four, five or all of the following properties:

(a) binds to Ebola virus glycoprotein with an $EC_{50}$ of 200 pM or less, as measured by ELISA;

(b) binds to a conformational epitope on Ebola virus glycoprotein (SEQ ID NO: 91);

(c) binds within the region V505-C511 of Ebola virus glycoprotein (SEQ ID NO: 91);

(d) binds within the region N550-E564 of Ebola virus glycoprotein (SEQ ID NO: 91); and (e) engages immune components such as antibody-dependent cellular cytotoxicity (ADCC) or complement-dependent cytotoxicity (CDC).

One aspect of the invention relates to a monoclonal antibody 13C6.1 comprising a variable heavy chain and a variable light chain set forth in SEQ ID NOs: 15 and 17, which binds to T270-P279 and Y394-R409 of Ebola virus glycoprotein (SEQ ID NO: 91).

Yet other aspects of the invention relate to a monoclonal antibody 13C6.1 which binds to Ebola virus glycoprotein with an $EC_{50}$ of 200 pM or less, as measured by ELISA. Other aspects of the invention relate to monoclonal antibody 13C6.1 which binds to Ebola virus glycoprotein with an $EC_{50}$ of 136 pM or less, as measured by ELISA.

Yet other aspects of the invention relate to a monoclonal antibody 13C6.1 which has neutralizing activity against Zaire Ebola Virus. In one aspect, the invention relates to a monoclonal antibody 13C6.1 which neutralizes Ebola virus Mayinga 1976 strain at >50 μg/mL, as measured by a plaque reduction neutralization assay. In another aspect, the invention relates to a monoclonal antibody 13C6.1 which neutralizes Ebola virus Kikwit 1995 strain at >50 μg/mL, as measured by a plaque reduction neutralization assay. Another aspect of the invention relates to a monoclonal antibody 13C6.1 neutralizes Ebola virus Makon 2014 strain at >50 μg/mL, as measured by a plaque reduction neutralization assay.

Other aspects of the invention relate to a monoclonal antibody 13C6.1 comprising a variable heavy chain and a variable light chain set forth in SEQ ID NOs: 15 and 17, which engages immune components such as antibody-dependent cellular cytotoxicity (ADCC) or complement-dependent cytotoxicity (CDC).

In another aspect, the invention relates to an isolated monoclonal antibody, or antigen binding portion thereof, which specifically binds to Ebola virus glycoprotein and competes for binding to Ebola virus glycoprotein with a monoclonal antibody 13C6.1, wherein the monoclonal antibody exhibits at least one, two, three, four, five or all of the following properties:

(a) binds to Ebola virus glycoprotein with an $EC_{50}$ of 200 pM or less, as measured by ELISA;

(b) binds to a conformational epitope on Ebola virus glycoprotein (SEQ ID NO: 91);

(c) binds within the region T270-P279 of Ebola virus glycoprotein (SEQ ID NO: 91);

(d) binds within the region Y394-R409 of Ebola virus glycoprotein (SEQ ID NO: 91); and (e) engages immune components such as antibody-dependent cellular cytotoxicity (ADCC) or complement-dependent cytotoxicity (CDC).

One aspect of the invention relates to a monoclonal antibody 2G4.6 comprising a variable heavy chain and a variable light chain set forth in SEQ ID NOs: 32 and 37, which binds to V505-C511 and N550-E564 of Ebola virus glycoprotein (SEQ ID NO: 91). Other aspects of the invention relate to monoclonal antibody 2G4.3, which binds within the region V505-C511 or within the region N550-E562, or both.

Yet other aspects of the invention relate to a monoclonal antibody 2G4.6 which binds to Ebola virus glycoprotein with an $EC_{50}$ of 200 pM or less, as measured by ELISA. Another aspect of the invention relates to a monoclonal antibody 2G4.6 which binds to Ebola virus glycoprotein with an $EC_{50}$ of 109 pM or less, as measured by ELISA. Other aspects of the invention relate to a monoclonal antibody 2G4.3 which binds to Ebola virus glycoprotein with an $EC_{50}$ of 200 pM or less, as measured by ELISA. Other aspects of the invention relate to a monoclonal antibody 2G4.3 which binds to Ebola virus glycoprotein with an $EC_{50}$ of 129 pM or less, as measured by ELISA.

Yet other aspects of the invention relate to a monoclonal antibody 2G4.6 which has neutralizing activity against Zaire Ebola Virus. In one aspect, the invention relates to a monoclonal antibody 2G4.6 which neutralizes Ebola virus Mayinga 1976 strain at 2 μg/mL, as measured by a plaque reduction neutralization assay. In another aspect, the invention relates to a monoclonal antibody 2G4.6 which neutralizes Ebola virus Kikwit 1995 strain at 4 μg/mL, as measured by a plaque reduction neutralization assay. Another aspect of the invention relates to a monoclonal antibody 2G4.6 neutralizes Ebola virus Makon 2014 strain at 2 μg/mL, as measured by a plaque reduction neutralization assay.

Other aspects of the invention relate to a monoclonal antibody 2G4.6 comprising a variable heavy chain and a variable light chain set forth in SEQ ID NOs: 32 and 37, which engages immune components such as antibody-dependent cellular cytotoxicity (ADCC) or complement-dependent cytotoxicity (CDC). Yet other aspects of the invention relate to monoclonal antibodies 2G4.3, which engages immune components such as antibody-dependent cellular cytotoxicity (ADCC) or complement-dependent cytotoxicity (CDC).

In another aspect, the invention relates to an isolated monoclonal antibody, or antigen binding portion thereof, which specifically binds to Ebola virus glycoprotein and competes for binding to Ebola virus glycoprotein with a monoclonal antibody 2G4.6, wherein the monoclonal antibody exhibits at least one, two, three, four, five or all of the following properties:

(a) binds to Ebola virus glycoprotein with an $EC_{50}$ of 200 pM or less, as measured by ELISA;

(b) binds to a conformational epitope on Ebola virus glycoprotein (SEQ ID NO: 91);

(c) binds within the region V505-C511 of Ebola virus glycoprotein (SEQ ID NO: 91);

(d) binds within the region N550-E564 of Ebola virus glycoprotein (SEQ ID NO: 91); and (e) engages immune components such as antibody-dependent cellular cytotoxicity (ADCC) or complement-dependent cytotoxicity (CDC).

Yet other aspects of the invention relate to a pharmaceutical composition comprising a combination of monoclonal antibodies or antigen binding portions thereof, which bind to Ebola virus glycoprotein, and a pharmaceutically acceptable carrier, wherein the combination of monoclonal antibodies is selected from the foregoing monoclonal antibodies.

Some aspects of the invention relate to any of the preceding antibodies, or antigen binding portions thereof, in which the monoclonal antibody is an IgG1, an IgG2, an IgG3, an IgG4, an IgM, an IgA1, an IgA2, an IgD, or an IgE antibody. In some aspects of the invention, any of the preceding antibodies, or antigen binding portions thereof, is a monoclonal IgG1 antibody.

Other aspects of the invention relate to pharmaceutical compositions comprising any of the preceding monoclonal antibodies or antigen binding portions thereof, and a pharmaceutically acceptable carrier.

Other aspects of the invention relate to pharmaceutical compositions comprising one or more (e.g., two or three different monoclonal antibodies) of the preceding monoclonal antibodies or antigen binding portions thereof, and a pharmaceutically acceptable carrier.

Another aspect of the invention relates to methods for treating Ebola virus infection in a subject in need thereof, comprising administering a pharmaceutical composition comprising an effective amount of any of the preceding monoclonal antibodies or antigen binding portions thereof, or a combination of monoclonal antibodies (e.g., two or three different monoclonal antibodies) or antigen binding portions thereof; and a pharmaceutically acceptable carrier.

Other aspects of the invention relate to methods for treating Ebola virus infection in a subject in need thereof, comprising administering a first pharmaceutical composition comprising an effective amount of a first monoclonal antibody of any of the preceding monoclonal antibodies or antigen binding portions thereof, and a pharmaceutically acceptable carrier; and a second pharmaceutical composition comprising an effective amount of a second monoclonal antibody (different from the first) from any of the preceding monoclonal antibodies or antigen binding portions thereof, and a pharmaceutically acceptable carrier. In other aspects, a third pharmaceutical composition comprising an effective amount of a third monoclonal antibody (different from the first and second) from any of the preceding monoclonal antibodies or antigen binding portions thereof, and a pharmaceutically acceptable carrier is administered to the subject in need thereof.

In another aspect, the methods of the invention further comprise administering a therapeutic agent to a subject in need thereof. In one aspect, the therapeutic agent is interferon alpha.

Other aspects of the invention relate to a monoclonal antibody or antigen binding portion thereof of the preceding antibody, or one or more monoclonal antibodies or antigen binding portions thereof of the preceding antibodies, for use in treating Ebola virus infection. In some aspects, the use further comprises administering a therapeutic agent. In some embodiments, the therapeutic agent is interferon alpha.

Yet other aspects of the invention relate to methods for detecting Ebola virus infection in a subject, comprising obtaining a sample from the subject and contacting the sample with any of the preceding monoclonal antibodies or antigen binding portions thereof, or a combination of monoclonal antibodies (e.g., two or three different monoclonal antibodies) or antigen binding portions thereof; and detecting the presence of Ebola virus glycoprotein in the subject.

Some aspects of the invention relate to peptide or peptide mimetics based on one or more epitopes within Ebola virus glycoprotein region V505-C511, region N550-E564, region T270-P279, or region Y394-R404 of Ebola virus glycoprotein (SEQ ID NO: 91). Some aspects of the invention relate to peptide or peptide mimetics based on one or more epitopes within Ebola virus glycoprotein (SEQ ID NO: 91) that spans V505-C511 and N550-E564. Some aspects of the invention relate to peptide or peptide mimetics based on one or more conformational epitopes on Ebola virus glycoprotein (SEQ ID NO: 91) that spans T270-P279 and Y394-R409.

Some aspects of the invention relate to peptide or peptide mimetics based on one or more epitopes Ebola virus glycoprotein TGKLIWKVNP (SEQ ID NO: 98), YKLDISEATQVGQHHR (SEQ ID NO: 99), VNAQPKC (SEQ ID NO: 100), and NQDGLICGLRQLANE (SEQ ID NO: 101).

Other aspects of the invention relate to vaccine compositions that comprise the foregoing peptides, peptide mimetics (or fusion protein thereof). Such vaccine compositions may include one or more adjuvants. Methods of eliciting an anti-Ebola virus GP immune response in a subject, comprising administering to the animal an effective amount of the vaccine composition, are also provided.

BRIEF DESCRIPTION OF THE FIGURES

FIG. 2 is the sequence of the Ebola virus glycoprotein with amino acids marked as black or black with an underline if they had an effect on binding as determined in FIG. 1. GP=glycoprotein.

FIG. 5 is a table showing the neutralization titers of antibodies 13C6.1, 2G4.6, and 4G7.9 on three different Ebola virus strains.

DETAILED DESCRIPTION

Figure 1:
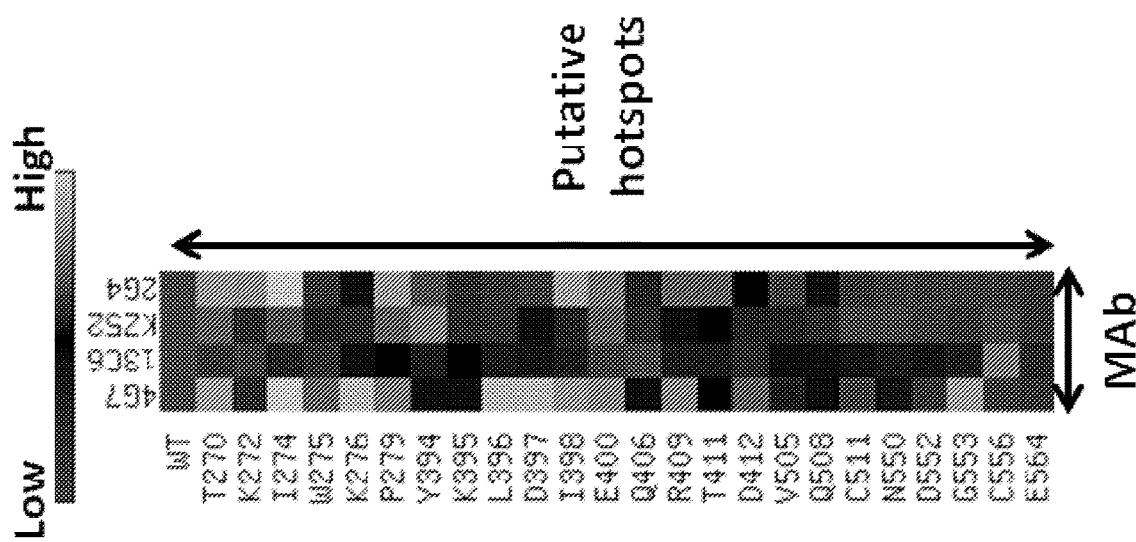
FIG. 1 is a heat map showing the effects of various point mutations in the Ebola virus glycoprotein on the binding of antibodies 4G7, 13C6, KZ52, and 2G4. Mutations that result in higher binding affinity are shown as a light color and mutations that that result in lower binding affinity are shown in a darker color. WT=wild-type Ebola virus glycoprotein.

The invention described herein pertains to monoclonal antibodies and antigen binding portions thereof directed towards Ebola virus glycoprotein (GP), which have desirable functional properties. These properties include high affinity binding to Ebola virus GP and neutralizing activity against the Zaire Ebola Virus, including the Makona 2014 strain. As described herein, the present invention identifies regions within Ebola virus GP that serve as specific neutralization epitopes for the monoclonal antibodies of the invention. These epitopes also serve to provide fragments of Ebola virus GP that are useful for eliciting an active and specific immune response against Ebola virus GP, both in vitro, e.g., for detection of GP, and in vivo, for inducing a protective immune response in subjects in need thereof.

Definitions

Terms used in the claims and specification are defined as set forth below unless otherwise specified.

The term "Ebola virus", refers to members of the family Filoviridae, which are associated with outbreaks of highly lethal hemorrhagic fever in humans and nonhuman primates. Human pathogens include Ebola Zaire, Ebola Sudan, and Ebola Ivory Coast. Ebola Reston is a monkey pathogen and is not considered a human pathogen. The natural reservoir of the virus is unknown and there are currently no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection. Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) Virus Res. 24, 1-19; Sanchez et al., (1993) Virus Res. 29, 215-240; reviewed in Peters et al. (1996) In *Fields Virolooy*, Third ed. pp. 1161-1176. Fields, B. N., Knipe, D. M., Howley, P. M., et al. eds. Lippincott-Raven Publishers, Philadelphia).

The term "Ebola virus glycoprotein (GP)" refers to the predominant surface protein expressed by the virus. The sequence of the Ebola virus GP (Zaire Ebola virus glycoprotein precursor, Genebank Accession: AR 96634.1) is set forth as SEQ ID NO: 91.

The glycoprotein of Ebola virus is the main surface antigen and responsible for viral entry and fusion, expressed as a trimer on the viral surface. It is unusual in that it is encoded in two open reading frames. Transcriptional editing is needed to express the transmembrane form that is incorporated into the virion (Sanchez et al. (1996) *Proc. Nati. Acad. Sci. USA* 93, 3602-3607; Volchkov et al, (1995) *Virology* 214, 421-430). The unedited form produces a nonstructural secreted glycoprotein (sGP) that is synthesized in large amounts early during the course of infection. During assembly of the virus, the glycoprotein undergoes enzymatic cleavage by furin and generates GP1 and GP2 domains. Little is known about the biological functions of these proteins and it is not known which antigens significantly contribute to protection and should therefore be used to induce an immune response.

The term "antibody" as referred to herein includes whole antibodies and any antigen binding fragment (i.e., "antigen-binding portion") or single chain thereof. An "antibody" refers, in certain embodiments, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., Ebola virus GP). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody," as used herein, refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, "neutralizing antibody" refers to an antibody, for example, a monoclonal antibody, capable of disrupting a formed viral particle or inhibiting formatting of a viral particle or prevention of binding to or infection of mammalian cells by a viral particle.

As used herein, "diagnostic antibody" or "detection antibody" or "detecting antibody" refers to an antibody, for example, a monoclonal antibody, capable of detecting the presence of an antigenic target within a sample. As will be appreciated by one of skill in the art, such diagnostic antibodies preferably have high specificity for their antigenic target.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90%, preferably at least 90-95%, more preferably at least 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, e.g., a non-human mammal.

Preferably, residue positions which are not identical differ by conservative amino acid substitutions. For purposes of classifying amino acids substitutions as conservative or nonconservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

Preferably, humanized immunoglobulins or antibodies bind antigen with an affinity that is within a factor of three, four, or five of that of the corresponding non-humanized antibody. For example, if the nonhumanized antibody has a binding affinity of $10^9$ $M^{-1}$, humanized antibodies will have a binding affinity of at least 3 times $10^9$ $M^{-1}$, 4 times $10^9$ $M^{-1}$ or $10^9$ $M^{-1}$. When describing the binding properties of an immunoglobulin or antibody chain, the chain can be described based on its ability to "direct antigen (e.g., Ebola GP) binding". A chain is said to "direct antigen binding" when it confers upon an intact immunoglobulin or antibody (or antigen binding fragment thereof) a specific binding property or binding affinity. A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

An "isolated antibody," as used herein, is intended to refer to an antibody which is substantially free of other antibodies having different antigenic specificities (e.g., an isolated antibody that specifically binds to Ebola virus GP is substantially free of antibodies that specifically bind antigens other than Ebola virus GP). An isolated antibody is typically substantially free of other cellular material and/or chemicals. In certain embodiments of the invention, a combination of "isolated" antibodies having different Ebola virus GP specificities is combined in a well defined composition.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from Ebola virus GP are tested for reactivity with the given anti-GP antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

The term "epitope mapping" refers to the process of identification of the molecular determinants for antibody-antigen recognition. Numerous methods for epitope mapping are known in the art, such as x-ray analysis, protease mapping, hydrogen/deuterium exchange mass spectrometry (HDX-MS), 2D nuclear magnetic resonance, alanine scanning, and deep mutational scanning.

To facilitate the engineering of antibodies that target the Ebola virus glycoprotein (GP), epitope hotspots were determined using alanine scanning, as described herein. Based on the binding analysis, antibodies 4G7, K252, and 2G4 were found to bind to a conformational epitope that included regions V505-C511 and N550-E564 of SEQ ID NO: 91, whereas antibody 13C6 was found to bind within the regions T270-P279 and Y394-R409 of SEQ ID NO: 91 (FIG. 1). FIG. 2 summarizes the hotspots in the Ebola virus glycoprotein identified through this mutational analysis. Some aspects of the invention relate to peptide or peptide mimetics based on one or more epitopes within Ebola virus glycoprotein region V505-C511, region N550-E564, region T270-P279, or region Y394-R404 of Ebola virus glycoprotein (SEQ ID NO: 91). Some aspects of the invention relate to peptide or peptide mimetics based on one or more epitopes within Ebola virus glycoprotein (SEQ ID NO: 91) that spans V505-C511 and N550-E564. Some aspects of the invention relate to peptide or peptide mimetics based on one or more conformational epitopes on Ebola virus glycoprotein (SEQ ID NO: 91) that spans T270-P279 and Y394-R409. Some aspects of the invention relate to peptide or peptide mimetics based on one or more epitopes Ebola virus glycoprotein TGKLIWKVNP (SEQ ID NO: 98), YKLDIS-EATQVGQHHR (SEQ ID NO: 99), VNAQPKC (SEQ ID NO: 100), and NQDGLICGLRQLANE (SEQ ID NO: 101).

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 2000 instrument using recombinant Ebola virus GP as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "$K_D$," as used herein, is intended to refer to the dissociation equilibrium constant of a particular antibody-antigen interaction.

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline. In some aspects of the invention, monoclonal antibodies or antigen binding portions thereof, bind to Ebola virus glycoprotein with an $EC_{50}$ of 300 pM or less, as measured by ELISA. In some aspects of the invention, monoclonal antibodies or antigen binding portions thereof, bind to Ebola virus glycoprotein with an $EC_{50}$ of 200 pM or less, as measured by ELISA. In some aspects of the invention, monoclonal antibodies or antigen binding portions thereof, bind to Ebola virus glycoprotein with an $EC_{50}$ of 150 pM or less, as measured by ELISA. In some aspects of the invention, monoclonal antibodies or antigen binding portions thereof, bind to Ebola virus glycoprotein with an $EC_{50}$ of 100 pM or less, as measured by ELISA.

As used herein, "isotype" refers to the antibody class (e.g., IgM or IgG1) that is encoded by heavy chain constant region genes. In one embodiment, a human monoclonal antibody of the invention is of the IgG1 isotype. In certain embodiments, the human IgG1 has a heavy chain constant domain sequence as set forth in SEQ ID NO: 1 and a light chain constant domain sequence as set forth in SEQ ID NO: 2.

The term "binds to Ebola virus glycoprotein (GP)," refers to the ability of a monoclonal antibody of the invention to specifically bind to Ebola virus GP, for example, expressed on the surface of a cell or which is attached to a solid support.

As used herein, the term "having neutralizing activity" refers to the reduction in viral infectivity by the binding of a monoclonal antibody of the invention, or antigen binding portion thereof, to Ebola Virus GP. Neutralization is measured in the presence or absence of complement.

As used herein, a plaque reduction neutralization assay is used to quantify the titre of neutralizing antibody for a virus. A serum sample or solution of antibody to be tested is diluted and mixed with a viral suspension. This is incubated to allow the antibody to react with the virus and poured over a confluent monolayer of host cells. The concentration of plaque forming units can be estimated by the number of plaques (regions of infected cells) formed after a few days. The concentration of serum to reduce the number of plaques by 50% compared to the serum free virus gives the measure of how much antibody is present or how effective it is. This measurement is denoted as the plaque reduction neutralization $(PRNT)_{50}$ value.

The term "nucleic acid molecule," as used herein, is intended to include DNA molecules and RNA molecules. A nucleic acid molecule may be single-stranded or double-stranded, but preferably is double-stranded DNA.

The present invention also encompasses "conservative sequence modifications" of the sequences set forth in the Sequence Table i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into sequences set forth in the Sequence Table by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted non-essential amino acid residue in a human anti-GP antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997))

Alternatively, in certain embodiments, mutations can be introduced randomly along all or part of an anti-Ebola Virus GP antibody coding sequence, such as by saturation mutagenesis, and the resulting modified anti-Ebola Virus GP antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

When given an amino acid sequence, one versed in the art can make conservative substitutions to the nucleotide sequence encoding it without altering the amino acid sequence, given the redundancy in the genetic code. The nucleic acid compositions, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "peptide" as used herein is defined as a chain of amino acid residues, usually having a defined sequence. As used herein the term peptide is interchangeable with the terms "polypeptide" and "protein". In the context of the present invention, the term "peptide" is defined as being any peptide or protein comprising at least two amino acids linked by a modified or unmodified peptide bond. The term "peptide" refers to short-chain molecules such as oligopeptides or oligomers or to long-Chain molecules such as proteins. A peptide according to the present invention can comprise modified amino acids. Thus, the peptide of the present invention can also be modified by natural processes such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, covalent bonding to a modified or unmodified carbohydrate moiety, bonding with a lipid or a lipid derivative, covalent bonding with a phosphotidylinositol, cross-linking, cyclization, disulfide bond formation, demethylation, cysteine molecule formation, pyroglutamate formation, formylation, gamma-carboxylation, hydroxylation, iodination, methylation, oxidation, phosphorylation, racemization, hydroxylation, etc. Thus, any modification of the peptide which does not have the effect of eliminating the immunogenicity of the peptide, is covered within the scope of the present invention.

The individual residues of the peptides of the invention protein can be incorporated in the peptide by a peptide bond or peptide bond mimetic. A peptide bond mimetic of the invention includes peptide backbone modifications well known to those skilled in the art. Such modifications include modifications of the amide nitrogen, the a-carbon, amide carbonyl, complete replacement of the amide bond, extensions, deletions or backbone cross-links. See, generally, Spatola, Chemistry and Biochemistry of Amino Acids, Peptides and Proteins, Vol. VII (Weinstein ed., 1983). Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ $CH=CH]$. The nomenclature used above, follows that suggested by Spatola, above. In this context, $\psi$ indicates the absence of an amide bond. The structure that replaces the amide group is specified within the brackets.

Amino acid mimetics may also be incorporated in the peptides. An "amino acid mimetic" as used here is a moiety other than a naturally occurring amino acid that conformationally and functionally serves as a substitute for an amino acid in a peptide of the present invention. Such a moiety serves as a substitute for an amino acid residue if it does not interfere with the ability of the peptide to bind to Ebola virus antibodies. Amino acid mimetics may include non-protein amino acids, such as $\beta$-, $\gamma$-, $\delta$-amino acids, $\beta$-, $\gamma$-, $\delta$-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. In addition, D-amino acids can be regarded as mimetics. Peptide mimetics suitable for peptides of the present invention are discussed by Morgan and Gainor, (1989) Ann. Repts. Med. Chem. 24:243-252.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, in need of such treatment, a human antibody of the present invention, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

Production of Antibodies to Ebola Virus Glycoprotein

The present invention encompasses antibodies, e.g., monoclonal antibodies that bind Ebola virus GP. Exemplary monoclonal antibodies that bind Ebola virus GP are optimized monoclonal antibodies which include CDRs or optimized CDRs based on the mouse monoclonal antibodies 13C6, 6D8, and 13F6 (as disclosed in U.S. Pat. Nos. 6,630,144 and 7,335,356), and mouse monoclonal antibodies 1H3, 2G4, and 4G7 (as disclosed in U.S. Pat. No. 8,513,391). Provided herein are isolated monoclonal antibodies or antigen binding portions thereof, comprising heavy and light chain variable sequences comprising (further described in Tables 1 and 2):

(a) SEQ ID NOs: 15 and 17, respectively;
(b) SEQ ID NOs: 15 and 18, respectively;
(c) SEQ ID NOs: 16 and 17, respectively;
(d) SEQ ID NOs: 16 and 18, respectively;
(e) SEQ ID NOs: 19 and 20, respectively;
(f) SEQ ID NOs:19 and 21, respectively;
(g) SEQ ID NOs: 22 and 23, respectively;
(h) SEQ ID NOs: 22 and 24, respectively;
(i) SEQ ID NOs: 9 and 10, respectively;
(j) SEQ ID NOs: 9 and 27, respectively;
(k) SEQ ID NOs: 9 and 28, respectively;
(l) SEQ ID NOs: 9 and 29, respectively;
(m) SEQ ID NOs: 9 and 30, respectively;
(n) SEQ ID NOs: 9 and 31, respectively;
(o) SEQ ID NOs: 25 and 10, respectively;
(p) SEQ ID NOs: 25 and 27, respectively;
(q) SEQ ID NOs: 25 and 28, respectively;
(r) SEQ ID NOs: 25 and 29, respectively;
(s) SEQ ID NOs: 25 and 30, respectively;
(t) SEQ ID NOs: 25 and 31, respectively;
(u) SEQ ID NOs: 26 and 10, respectively;
(v) SEQ ID NOs: 26 and 27, respectively;
(w) SEQ ID NOs: 26 and 28, respectively;
(x) SEQ ID NOs: 26 and 29, respectively;
(y) SEQ ID NOs: 26 and 30, respectively;
(z) SEQ ID NOs: 26 and 31, respectively;
(aa) SEQ ID NOs: 11 and 12, respectively;
(bb) SEQ ID NOs: 11 and 36, respectively;
(cc) SEQ ID NOs: 11 and 37, respectively;
(dd) SEQ ID NOs: 32 and 12, respectively;
(ee) SEQ ID NOs: 32 and 36, respectively;
(ff) SEQ ID NOs: 32 and 37, respectively;
(gg) SEQ ID NOs: 33 and 12, respectively;
(hh) SEQ ID NOs: 33 and 36, respectively;
(ii) SEQ ID NOs: 33 and 37, respectively;
(jj) SEQ ID NOs: 34 and 12, respectively;
(kk) SEQ ID NOs: 34 and 36, respectively;
(ll) SEQ ID NOs: 34 and 37, respectively;
(mm) SEQ ID NOs: 35 and 12, respectively;
(nn) SEQ ID NOs: 35 and 36, respectively;
(oo) SEQ ID NOs: 35 and 37, respectively;
(pp) SEQ ID NOs: 13 and 14, respectively;

(qq) SEQ ID NOs: 13 and 42, respectively;
(rr) SEQ ID NOs: 13 and 43, respectively;
(ss) SEQ ID NOs: 13 and 44, respectively;
(tt) SEQ ID NOs: 38 and 14, respectively;
(uu) SEQ ID NOs: 38 and 42, respectively;
(vv) SEQ ID NOs: 38 and 43, respectively;
(ww) SEQ ID NOs: 38 and 44, respectively;
(xx) SEQ ID NOs: 39 and 14, respectively;
(yy) SEQ ID NOs: 39 and 42, respectively;
(zz) SEQ ID NOs: 39 and 43, respectively;
(aaa) SEQ ID NOs: 39 and 44, respectively;
(bbb) SEQ ID NOs: 40 and 14, respectively;
(ccc) SEQ ID NOs: 40 and 42, respectively;
(ddd) SEQ ID NOs: 40 and 43, respectively;
(eee) SEQ ID NOs: 40 and 44, respectively;
(fff) SEQ ID NOs: 41 and 14, respectively;
(ggg) SEQ ID NOs: 41 and 42, respectively;
(hhh) SEQ ID NOs: 41 and 43, respectively; and
(iii) SEQ ID NOs: 41 and 44, respectively.

Monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

Accordingly, in certain embodiments, a hybridoma method is used for producing an antibody that binds Ebola virus GP. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies:Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In certain embodiments, antibodies and antibody portions that bind Ebola virus GP can be isolated from antibody phage libraries generated using the techniques described in, for example, McCafferty et al., Nature, 348:552-554 (1990). Clackson et al., Nature, 352:624-628 (1991), Marks et al., J. Mol. Biol., 222:581-597 (1991) and Hoet et al (2005) Nature Biotechnology 23, 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)) may also be used.

In certain embodiments, the antibody that binds Ebola virus GP is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to Ebola virus GP.

The preferred animal system for generating hybridomas which produce antibodies of the invention is the murine system. Hybridoma production in the mouse is well known in the art, including immunization protocols and techniques for isolating and fusing immunized splenocytes.

In certain embodiments, antibodies directed against Ebola virus GP are generated using transgenic or transchromosomal mice carrying parts of the human immune system rather than the mouse system. In one embodiment, the invention employs transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). The preparation of HuMAb mice is described in detail below and in Taylor, L. et al. (1992) Nucleic Acids Research 20:6287-6295; Chen, J. et al. (1993) International Immunology 5: 647-656; Tuaillon et al. (1993) Proc. Natl. Acad. Sci USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Lonberg et al., (1994) Nature 368(6474): 856-859; Lonberg, N. (1994) Handbook of Experimental Pharmacology 113:49-101; Taylor, L. et al. (1994) International Immunology 6: 579-591; Lonberg, N. and Huszar, D. (1995) Intern. Rev. Immunol. Vol. 13: 65-93; Harding, F. and Lonberg, N. (1995) Ann. N.Y. Acad. Sci 764:536-546; Fishwild, D. et al. (1996) Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

In certain embodiments, human antibodies of the invention can be raised using a mouse that carries human immunoglobulin sequences on transgenes and transchomosomes, such as a mouse that carries a human heavy chain transgene and a human light chain transchromosome. Such mice, referred to in the art as "KM mice", are described in detail in PCT Publication WO 02/43478 to Ishida et al.

Still further, alternative transgenic animal systems expressing human immunoglobulin genes are available in the art and can be used to raise anti-Ebola virus GP antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-Ebola virus GP antibodies of the invention. For example, mice carrying both a human heavy chain transchromosome and a human light chain tranchromosome, referred to in the art as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-Ebola virus GP antibodies of the invention.

Additional mouse systems described in the art for raising human antibodies also can be applied to raising anti-Ebola virus GP antibodies of the invention, including but not limited to (i) the VelocImmune® mouse (Regeneron Pharmaceuticals, Inc.), in which the endogenous mouse heavey and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the mAbs described herein can be produced in plants using deconstructed viral vectors, as described in Olinger et al., *PNAS* 2012; 109, 18030-18035, herein incorporated by reference. In certain embodiments, the mAbs are produced in tobacco plants.

In certain embodiments, chimeric antibodies can be prepared based on the sequence of a murine monoclonal antibodies described herein. A chimeric antibody refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

Production of Humanized Antibodies

The term "humanized antibody" refers to an antibody comprising at least one chain comprising variable region framework residues substantially from a human antibody chain (referred to as the acceptor immunoglobulin or antibody) and at least one complementarity determining region substantially from a mouse antibody, (referred to as the donor immunoglobulin or antibody). See, Queen et al., Proc. Natl. Acad. Sci. USA 86:10029-10033 (1989), U.S. Pat. Nos. 5,530,101, 5,585,089, 5,693,761, 5,693,762, Selick et al., WO 90/07861, and Winter, U.S. Pat. No. 5,225,539 (incorporated by reference in their entirety for all purposes). The constant region(s), if present, are also substantially or entirely from a human immunoglobulin.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:
  (1) noncovalently binds antigen directly,
  (2) is adjacent to a CDR region,
  (3) otherwise interacts with a CDR region (e.g., is within about 3-6 angstroms of a CDR region as determined by computer modeling), or
  (4) participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like.

CDR and framework regions are as defined by Kabat et al. or Chothia et al., supra. When framework residues, as defined by Kabat et al., supra, constitute structural loop residues as defined by Chothia et al., supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to affect a CDR region. In certain embodiments, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (A) of some atom in the CDRs and must contain an atom that could interact with the CDR atoms according to established chemical forces, such as those listed above.

In the case of atoms that may form a hydrogen bond, the 3 Angstroms is measured between their nuclei, but for atoms that do not form a bond, the 3 Angstroms is measured between their Van der Waals surfaces. Hence, in the latter case, the nuclei must be within about 6 Angstroms (3 Angstroms plus the sum of the Van der Waals radii) for the atoms to be considered capable of interacting. In many cases the nuclei will be from 4 or 5 to 6 Angstroms apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many antibodies (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criteria help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding are retained, whereas residues predicted to be unimportant for binding can be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

The humanized antibodies preferably exhibit a specific binding affinity for antigen of at least $10^7$, $10^8$, $10^9$ or $10^{10}$ $M^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

Immunizations

To generate fully human antibodies to Ebola virus GP, transgenic or transchromosomal mice containing human immunoglobulin genes (e.g., HCo12, HCo7 or KM mice) can be immunized with a purified or enriched preparation of the Ebola virus GP antigen and/or cells expressing Ebola virus GP, as described, for example, by Lonberg et al. (1994) *Nature* 368(6474): 856-859; Fishwild et al. (1996) *Nature Biotechnology* 14: 845-851 and WO 98/24884. As described herein, HuMAb mice are immunized either with recombinant Ebola virus GP proteins or cell lines expressing Ebola virus GP as immunogens. Alternatively, mice can be immunized with DNA encoding Ebola virus GP. Preferably, the mice will be 6-16 weeks of age upon the first infusion. For example, a purified or enriched preparation (5-50 μg) of the recombinant Ebola virus GP antigen can be used to immunize the HuMAb mice intraperitoneally.

Cumulative experience with various antigens has shown that the transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-Ebola virus GP human immunoglobulin can be used for fusions. Mice can be boosted intravenously with antigen 3 days before sacrifice and removal of the spleen.

Generation of Hybridomas Producing Monoclonal Antibodies to Ebola Virus GP

To generate hybridomas producing monoclonal antibodies to Ebola virus GP, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human anti-Ebola virus GP monoclonal IgM and IgG antibodies. Once extensive hybridoma growth occurs, medium can be observed usually after 10-14 days. The antibody secreting hybridomas can be replated, screened again, and if still positive for IgG, anti-Ebola virus GP monoclonal antibodies can be subcloned at least twice by limiting dilution. The stable subclones can then be cultured in vitro to generate antibody in tissue culture medium for characterization.

Generation of Transfectomas Producing Monoclonal Antibodies to Ebola Virus GP

Antibodies of the invention also can be produced in a host cell transfectoma using, for example, a combination of recombinant DNA techniques and gene transfection methods as is well known in the art (Morrison, S. (1985) Science 229:1202).

For example, in certain embodiments, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and up scaled to produce antibodies. Recombinant antibodies can be isolated and purified from these culture supernatants and/or cells.

Alternatively these cloned antibody genes can be expressed in other expression systems such as E. coli or in complete organisms or can be synthetically expressed.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:

19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors were constructed so that PCR amplified V heavy and V kappa light chain cDNA sequences could be used to reconstruct complete heavy and light chain minigenes. These plasmids can be used to express completely human $IgG_1\kappa$ or $IgG_4\kappa$ antibodies.

Fully human, humanized, and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 45-47; and (2) light chain framework regions and light chain CDRs, where at least one of the light chain CDRs includes an amino acid sequence selected from the amino acid sequences of CDRs shown in SEQ ID NOs: 48, 50, and 51; where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 52-54; and (2) light chain framework regions and light chain CDRs, where at least one of the light chain CDRs includes an amino acid sequence selected from the amino acid sequences of CDRs shown in SEQ ID NOs: 55, 56, and 58; where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 52-54 and (2) light chain framework regions and light chain CDRs, where at least one of the light chain CDRs includes an amino acid sequence selected from the amino acid sequences of CDRs shown in SEQ ID NOs: 55, 56, and 59; where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 60, 61, and 63; and (2) light chain framework regions and light chain CDRs, where at least one of the light chain CDRs includes an amino acid sequence selected from the amino acid sequences of CDRs shown in SEQ ID NOs: 64, 65, and 67; where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 74, 77, and 78; and (2) light chain framework regions and light chain CDRs, where at least one of the light chain CDRs includes an amino acid sequence selected from the amino acid sequences of CDRs shown in SEQ ID NOs: 80-82; where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 74, 77, and 79 and (2) light chain framework regions and light chain CDRs, where at least one of the light chain CDRs includes an amino acid sequence selected from the amino acid sequences of CDRs shown in SEQ ID NOs: 80-82 where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 83-85 and (2) light chain framework regions and light chain CDRs, where at least one of the light chain CDRs includes an amino acid sequence selected from the amino acid sequences of CDRs shown in SEQ ID NOs: 87, 90, and 89; where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 86, 84, and 85; and (2) light chain framework regions and light chain CDRs, where at least one of the light chain CDRs includes an amino acid sequence selected from the amino acid sequences of CDRs shown in SEQ ID NOs:87-89 where the antibody retains the ability to bind to Ebola virus GP. The ability of the antibody to bind Ebola virus GP can be determined using standard binding assays (e.g., an ELISA or a FLISA).

In certain embodiments, the invention provides a method for preparing an anti-Ebola virus GP antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 86, 84, and 85; and (2) light chain framework regions and light chain CDRs, where at least one of the light chain CDRs includes an amino acid sequence selected from the amino acid sequences of CDRs shown in SEQ ID NOs: 87, 90, and 89; where the antibody retains the ability to bind to Ebola virus GP. The ability of the antibody to bind Ebola virus GP can be determined using standard binding assays (e.g., an ELISA or a FLISA).

Accordingly, in certain embodiments, the invention further provides anti-Ebola virus GP antibodies comprising: (1) heavy chain framework regions, a heavy chain CDR1 region, a heavy chain CDR2 region, and a heavy chain CDR3 region, wherein the heavy chain CDR3 region is selected from the CDR3s of the antibodies disclosed herein and (2) light chain framework regions, a light chain CDR1 region, a light chain CDR2 region, and a light chain CDR3 region, wherein the light chain CDR3 region is selected from the CDR3s of the antibodies disclosed herein, wherein the antibody binds Ebola virus GP. The antibody may further include the heavy chain CDR2 and/or the light chain CDR2 of the antibodies disclosed herein. The antibody may further comprise the heavy chain CDR1 and/or the light chain CDR1 of the antibodies disclosed herein.

Generation of Antibodies Having Modified Sequences

In another embodiment, the variable region sequences, or portions thereof, of the anti-Ebola virus GP antibodies of the invention are modified to create structurally related anti-Ebola virus GP antibodies that retain binding (i.e., to the same epitope as the unmodified antibody).

Accordingly, in one aspect of the invention, the CDR1, 2, and/or 3 regions of the engineered antibodies described above can comprise the exact amino acid sequence(s) as those of antibodies disclosed herein. However, in other aspects of the invention, the antibodies comprise derivatives from the exact CDR sequences of the antibodies disclosed herein, still retain the ability of to bind Ebola virus GP effectively. Such sequence modifications may include one or more amino acid additions, deletions, or substitutions, e.g., conservative sequence modifications as described above. Sequence modifications may also be based on the consensus sequences described above for the particular CDR1, CDR2, and CDR3 sequences of antibodies disclosed herein.

Accordingly, in another embodiment, the engineered antibody may be composed of one or more CDRs that are, for example, 90%, 95%, 98% or 99.5% identical to one or more CDRs of antibodies disclosed herein. Ranges intermediate to the above-recited values, e.g., CDRs that are 90-95%, 95-98%, or 98-100% identical identity to one or more of the above sequences are also intended to be encompassed by the present invention.

In another embodiment, one or more residues of a CDR may be altered to modify binding to achieve a more favored on-rate of binding, a more favored off-rate of binding, or both, such that an idealized binding constant is achieved. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Thus, for variable region modification within the VH and/or VL CDR1, CDR2 and/or CDR3 regions, site-directed mutagenesis or PCR-mediated mutagenesis can be performed to introduce the mutation(s) and the effect on antibody binding, or other functional property of interest, can be evaluated in in vitro or in vivo assays. Preferably conservative modifications (as discussed herein) are introduced. The mutations can be amino acid substitutions, additions or deletions, but are preferably substitutions. Moreover, typically no more than one, two, three, four or five residues within a CDR region are altered.

Accordingly, in another embodiment, the instant invention provides isolated anti-Ebola virus GP monoclonal antibodies, or antigen binding portions thereof, comprising: (a) a VH CDR1 region comprising an amino acid sequence selected from the group consisting of SEQ ID NOs: 45, 52, 60, 68, 74, and 83, or an amino acid sequence having one, two, three, four or five amino acid substitutions, deletions or additions as compared to SEQ ID NOs: 45, 52, 60, 68, 74, and 83; (b) a VH CDR2 region comprising an amino acid sequence selected from the group consisting of SEQ ID NOs: 46, 53, 61, 69, 75, and 84, or an amino acid sequence having one, two, three, four or five amino acid substitutions, deletions or additions as compared to SEQ ID NOs: 46, 53, 61, 69, 75, and 84; (c) a VH CDR3 region comprising an amino acid sequence selected from the group consisting of SEQ ID NOs: 47, 54, 62, 70, 76, and 85, or an amino acid sequence having one, two, three, four or five amino acid substitutions, deletions or additions as compared to SEQ ID NOs: 47, 54, 62, 70, 76, and 85; (d) a VL CDR1 region comprising an amino acid sequence selected from the group consisting of SEQ ID NOs: 48, 55, 64, 71, 80, and 87, or an amino acid sequence having one, two, three, four or five amino acid substitutions, deletions or additions as compared to SEQ ID NOs: 48, 55, 64, 71, 80, and 87; (e) a VL CDR2 region comprising an amino acid sequence selected from the group consisting of SEQ ID NOs: 49, 56, 65, 72, 81, and 88, or an amino acid sequence having one, two, three, four or five amino acid substitutions, deletions or additions as compared to SEQ ID NOs: 49, 56, 65, 72, 81, and 88; and (f) a VL CDR3 region comprising an amino acid sequence selected from the group consisting of SEQ ID NOs: 51, 57, 66, 73, 82, and 89, or an amino acid sequence having one, two, three, four or five amino acid substitutions, deletions or additions as compared to SEQ ID NOs: 51, 57, 66, 73, 82, and 89.

In addition to or instead of modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody. In certain embodiments, the isolated monoclonal antibody comprises a heavy chain comprising CDR1, CDR2, and CDR3 sequences set forth in SEQ ID NOs: 68, 69, and 70, respectively, and any one of variable region framework residue mutations 49H, 71H, or a combination thereof (Kabat numbering convention) from the heavy chain variable region set forth in SEQ ID NO: 92, wherein the remainder of the heavy chain is from a human immunoglobulin; and a light chain comprising CDR1, CDR2, and CDR3 sequences set forth in SEQ ID NOs: 71, 72, and 73, respectively, and any one of variable region framework residue mutations 42 L, 59 L, 70 L, 99 L, or a combination thereof (Kabat numbering convention) from the light chain variable region set forth in SEQ ID NO: 93, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 74, 75, and 76, respectively, and any one of variable region framework residue mutations 49H, 50H, or a combination thereof (Kabat numbering convention) from the heavy chain variable region set forth in SEQ ID NO: 94, wherein the remainder of the heavy chain is from a human immunoglobulin; and a light chain comprising CDR1, CDR2, and CDR3 sequences set forth in SEQ ID NOs: 80, 81, and 82, respectively, and variable region framework residue mutations 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 74, 77, and 78, respectively, wherein the remainder of the heavy chain is from a human immunoglobulin; and a light chain comprising CDR1, CDR2, and CDR3 sequences set forth in SEQ ID NOs: 80, 81, and 82, respectively, and any one of variable region framework residue mutations 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 74, 77, and 79, respectively, wherein the remainder of the heavy chain is from a human immunoglobulin; and a light chain comprising CDR1, CDR2, and CDR3 sequences set forth in SEQ ID NOs: 80, 81, and 82, respectively, and any one of variable region framework residue mutations 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 83, 84, and 85, respectively, and any one of variable region framework residue mutations 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 88, and 89, respectively, and any one of variable region framework residue mutations of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 86, 84, and 85, respectively, and any one of variable region framework residue mutations 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 88, and 89, respectively, and any one of variable region framework residue mutations 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 83, 84, and 85, respectively, and any one of variable region framework residue mutations 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 90, and 89, respectively, and any one of variable region framework residue mutations 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the monoclonal antibody used herein comprises a heavy chain comprising CDR1, CDR2, and CDR3 sequences set forth in SEQ ID NOs: 86, 84, and 85, respectively, and any one of variable region framework residue mutations 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 90, and 89, respectively, and any one of variable region framework residue mutations 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In general, the framework regions of antibodies are usually substantially identical, and more usually, identical to the framework regions of the human germline sequences from which they were derived. Of course, many of the amino acids in the framework region make little or no direct contribution to the specificity or affinity of an antibody.

Thus, many individual conservative substitutions of framework residues can be tolerated without appreciable change of the specificity or affinity of the resulting immunoglobulin. Thus, in one embodiment the variable framework region of the antibody shares at least 85% sequence identity to a human germline variable framework region sequence or consensus of such sequences. In another embodiment, the variable framework region of the antibody shares at least 90%, 95%, 96%, 97%, 98% or 99% sequence identity to a human germline variable framework region sequence or consensus of such sequences.

In certain embodiments, framework regions are mutated. In certain embodiments, alanine is substituted for a glycine at residue 49 in the heavy chain variable region of SEQ ID NO: 9. In certain embodiments, serine is substituted for a threonine at residue 71 in the heavy chain variable region of SEQ ID NO: 9. In certain embodiments, alanine is substituted for a serine at residue 42 in the light chain variable region of SEQ ID NO: 10. In certain embodiments alanine is substituted for a valine at residue 59, phenylalanine is substituted for tyrosine at residue 70, and glutamine is substituted for glycine at residue 99 in the light chain variable region of SEQ ID NO: 10.

In certain embodiments, glycine is substituted for an alanine at residue 49 and phenylalanine is substituted for glutamic acid at residue 50 in the heavy chain variable region of SEQ ID NO: 11. In certain embodiments, alanine is substituted for a valine at residue 102 in the heavy chain variable region of SEQ ID NO: 11. In certain embodiments, alanine is substituted for a serine at residue 43, lysine is substituted for a glutamine at residue 45, and glutamine is substituted for a glycine at residue 100 in the light chain variable region of SEQ ID NO: 12. In certain embodiments, glutamine is substituted for valine at residue 3, aspartic acid is substituted for glutamine at residue 70, and phenylalanine is substituted for tyrosine at reside 71, in the light chain variable region of SEQ ID NO: 12.

In certain embodiments, glycine is substituted for serine at residue 44 in the heavy chain variable region of SEQ ID NO: 13. In certain embodiments, methionine is substituted for isoleucine at residue 48, isoleucine is substituted for leucine at residue 70, and alanine is substituted for valine at reside 72, in the heavy chain variable region of SEQ ID NO: 13. In certain embodiments, asparagine is substituted for valine at residue 50 in the heavy chain variable region of SEQ ID NO: 13. In certain embodiments, phenylalanine is substituted for valine at residue 32 in the heavy chain variable region of SEQ ID NO: 13. In certain embodiments, alanine is substituted for serine at residue 43 and tyrosine is substituted for phenylalanine at residue 87, in the light chain variable region of SEQ ID NO: 14. In certain embodiments, glutamine is substituted for valine at residue 3, aspartic acid is substituted for glutamine at residue 70, threonine is substituted for serine at residue 72, phenylalanine is substituted for leucine at residue 73, and glutamine is substituted for serine at residue 100, in the light chain variable region of SEQ ID NO: 14. In certain embodiments, lysine is substituted for valine at residue 52 in the light chain variable region of SEQ ID NO: 14.

Framework modifications can also be made to reduce immunogenicity of the antibody or to reduce or remove T cell epitopes that reside therein, as described for instance by Carr et al in US2003/0153043.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

Additional Antibody Modifications

Antibodies of the present disclosure can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N—X—S/T sequence. In some instances, it is preferred to have an anti-Ebola virus antibody that does not contain variable region glycosylation. This can be achieved either by selecting antibodies that do not contain the glycosylation motif in the variable region or by mutating residues within the glycosylation region.

For example, in certain embodiments, the glycosylation of an antibody is modified, e.g., the variable region is altered to eliminate one or more glycosylation sites resident in the variable region. More particularly, it is desirable in the sequence of the present antibodies to eliminate sites prone to glycosylation. This is achieved by altering the occurrence of one or more N—X—(S/T) sequences that occur in the parent variable region (where X is any amino acid residue), particularly by substituting the N residue and/or the S or T residue. In one embodiment, T95 is mutated to K95. In another embodiment, N47 is mutated to R47.

For example, aglycoslated antibodies can be made (i.e., which lack glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, the antibody can have an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha(1,6)$-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. Patent application filed on Aug. 11, 2006. PCT Publication WO 99/54342 describes cell lines engineered to express glycoprotein-modifying glycosyl transferases (e.g., $\beta(1,4)$-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase $\alpha$-L-fucosidase removes fucosyl residues from antibodies (Tarentino et al. (1975) Biochem. 14:5516-23).

The variable segments of antibodies produced as described supra (e.g., the heavy and light chain variable regions of chimeric or humanized antibodies) are typically linked to at least a portion of an immunoglobulin constant region (Fc region), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. When it is desired that the antibody (e.g., humanized antibody) exhibit cytotoxic activity, the constant domain is usually a complement fixing constant domain and the class is typically IgG1. Human isotype IgG1 is preferred. Light chain constant regions can be lambda or kappa. The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In certain embodiments, the antibody comprises a variable region that is mutated to improve the physical stability of the antibody. In one embodiment, the antibody is an IgG4 isotype antibody comprising a serine to proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). For example, in certain embodiments, an anti-Ebola virus GP antibody of the invention can comprise the heavy chain variable region of any of the antibodies described herein linked to a human IgG4 constant region in which the Serine at a position corresponding to position 241 as described in Angal et al., supra, has been mutated to Proline. Thus, for the heavy chain variable regions linked to a human IgG4 constant region, this mutation corresponds to an S228P mutation by the EU index.

In certain embodiments, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In addition, the antibody can be pegylated, for example, to increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Expression of Recombinant Antibodies

Chimeric and humanized antibodies are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilis*, and other enterobacteriaceae, such as Salmonella, Serratia, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Other microbes, such as yeast, are also useful for expression.

*Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., J. Immunol. 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., Molecular Cloning: A Laboratory Manual (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

Antibody Fragments

Also contemplated within the scope of the instant invention are antibody fragments. In one embodiment, fragments of non-human, and/or chimeric antibodies are provided. In another embodiment, fragments of humanized antibodies are provided. Typically, these fragments exhibit specific binding to antigen with an affinity of at least $10^7$, and more typically $10^8$ or $10^9 M^{-1}$. Humanized antibody fragments include separate heavy chains, light chains, Fab, Fab', F(ab')2, Fabc, and Fv. Fragments are produced by recombinant DNA techniques, or by enzymatic or chemical separation of intact immunoglobulins.

Assays for Characterization of Antibodies

Antibodies described herein can be tested for binding to Ebola virus glycoprotein (GP) by, for example, standard ELISA. Briefly, microtiter plates are coated with purified Ebola virus (i.e., Ebola Zaire 1995 virions) at 10-20 µg/ml in PBS, and then blocked with 5% nonfat dry milk in PBS. After washing, 0.05 mL of purified mAbs were added to wells containing antigen and incubated for 2 hours at room temperature. Bound mAbs were detected using horseradish peroxidase conjugated goat anti-mouse IgA+IgG+IgM secondary antibodies and ABTS substrate (Kirkegaard and Perry Laboratories).

An ELISA assay as described above can be used to screen for antibodies and, thus, hybridomas that produce antibodies that show positive reactivity with the Ebola virus GP. Hybridomas that produce antibodies that bind, preferably with high affinity, to Ebola virus GP can then be subcloned and further characterized. One clone from each hybridoma, which retains the reactivity of the parent cells (by ELISA), can then be chosen for making a cell bank, and for antibody purification.

The ELISA assay described above can also be used to confirm that framework mutation(s) do not affect the ability of the anti-GP antibodies disclosed herein to bind to GP.

To purify anti-Ebola virus GP antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-Ebola virus GP monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using Ebola virus GP coated-ELISA plates as described above.

To determine the isotype of purified antibodies, isotype ELISAs can be performed using reagents specific for antibodies of a particular isotype. For example, plates are coated with anti-IgG, IgA, or IgM heavy-chain specific antibodies (100 ng/well) and incubated with hybridoma culture supernatants. The subtype of the mAb is detected by using anti-IgG1, IgG2a, IgG2b, IgG3, IgM, or IgA heavy-chain specific antibodies conjugated to alkaline phosphatase.

Anti-Ebola virus GP antibodies can be further tested for reactivity with the Ebola virus GP antigen by Western blotting. Briefly, unlabeled Ebola Zaire 1995 virion proteins are resolved on a 10% SDS-polyacrylaminde gel and transferred to PVDF membranes. After nonspecific bindings sites are blocked using nonfat dry milk in PBS containing 0.02% TWEEN-20 (polysorbate-20), purified mAb (10 ug/ml) are added to the membranes for 1 hour at room temperature. Membranes are then incubated with horseradish peroxidase-conjugated goat anti-mouse IgA+IgG+IgM secondary antibodies for 1 hour and develobed using ECL chemiluminescence kit (Amersham).

Methods for analyzing binding affinity, cross-reactivity, and binding kinetics of various anti-Ebola virus GP antibodies include standard assays known in the art, for example, Biacore™ surface plasmon resonance (SPR) analysis using a Biacore™ 2000 SPR instrument (Biacore AB, Uppsala, Sweden).

To determine the neutralization of mAbs described herein, in vitro plaque reduction neutralization assays can be performed. Briefly, plaque assays are done using confluent Vero-E6 cells. Four-fold serial dilutions of mAbs are mixed with 100 pfu of mouse-adapted Ebola virus at 37° C. for 1 hour. In certain embodiments, the Ebloa virus is the Mayinga 1976 strain. In certain embodiments, the Ebola virus is the Kikwit 1995 strain. In certain embodiments, the Ebola virus is the Makona 2014 strain. Cells are covered with an agarose overlay and a second overlay containing 5% neutral red solution in PBS or agarose is added 6 days later. Plaques are counted the following day and endpoint titers are determined to be the last dilution of mAb that reduced the number of plaques by 80% of cells not incubated with mAbs.

Some aspects of the invention relate to a monoclonal antibody or antigen binding portion thereof which has neutralizing activity against Zaire Ebola Virus. In one aspect, the invention relates to a monoclonal antibody which neutralizes Ebola virus at 50 ug/mL, as measured by a plaque reduction neutralization assay. In another aspect, the invention relates to a monoclonal antibody which neutralizes Ebola virus at less than 50 µg/mL, as measured by a plaque reduction neutralization assay. Another aspect of the invention relates to a monoclonal antibody which neutralizes Ebola virus at less than 20 µg/mL, as measured by a plaque reduction neutralization assay. Another aspect of the invention relates to a monoclonal antibody which neutralizes Ebola virus at less than 10 µg/mL, as measured by a plaque reduction neutralization assay. Another aspect of the invention relates to a monoclonal antibody which neutralizes Ebola virus at less than 5 µg/mL, as measured by a plaque reduction neutralization assay. Another aspect of the invention relates to a monoclonal antibody which neutralizes Ebola virus at 1-5 or 2-4 µg/mL, as measured by a plaque reduction neutralization assay.

To determine the in vivo capability of the mAbs described herein, BALB/c or C57BL/6 mice are used. Mice are challenged with mouse-adapted Ebola Zaire virus 24 hours after injection of purified mAbs or combinations of mAbs to determine the prophylactic benefits. To determine the therapeutic benefit of the mAbs described herein, mAbs are injected 1, 2 or 3 days after Ebola Zaire virus challenge. Animals are monitored for morbidity and mortality for 28 days post infection.

Competitive Binding Antibodies

In certain embodiments, antibodies of the invention compete (e.g., cross-compete) for binding to Ebola virus GP with the particular anti-GP antibodies described herein. Such competing antibodies can be identified based on their ability to competitively inhibit binding to Ebola virus GP of one or more of mAbs described herein in standard Ebola virus GP binding assays. For example, standard ELISA assays can be used in which a recombinant Ebola virus GP is immobilized on the plate, one of the antibodies is fluorescently labeled and the ability of non-labeled antibodies to compete off the binding of the labeled antibody is evaluated. Additionally or alternatively, BlAcore analysis can be used to assess the ability of the antibodies to cross-compete. The ability of a test antibody to inhibit the binding of an anti-GP antibody of the invention to Ebola virus GP demonstrates that the test antibody can compete with the antibody for binding to Ebola virus GP In certain embodiments, the competing antibody is an antibody that binds to the same epitope on Ebola virus GP as the particular anti-GP monoclonal antibodies described herein. Standard epitope mapping techniques, such as x-ray crystallography and 2-dimensional nuclear magnetic resonance, can be used to determine whether an antibody binds to the same epitope as a reference antibody (see, e.g., Epitope Mapping Protocols in Methods in Molecular Biology, Vol. 66, G. E. Morris, Ed. (1996)).

In certain embodiments, the antibody that competes for binding to Ebola virus GP and/or binds to the same epitope on Ebola virus GP is a humanized antibody.

Once a single, archtypal anti-GP mAb has been isolated that has the desired properties described herein, it is straightforward to generate other mAbs with similar properties, e.g., having the same epitope, by using art-known methods. For example, mice may be immunized with Ebola virus as described herein, hybridomas produced, and the resulting mAbs screened for the ability to compete with the archtypal mAb for binding to Ebola virus GP. Mice can also be immunized with a smaller fragment of Ebola virus GP containing the epitope to which the archtypal mAb binds. The epitope can be localized by, e.g., screening for binding to a series of overlapping peptides spanning Ebola virus GP. Alternatively, the method of Jespers et al., Biotechnology 12:899, 1994 ma be used to guide the selection of mAbs having the same epitope and therefore similar properties to the archtypal mAb. Using phage display, first the heavy chain of the archtypal antibody is paired with a repertoire of (preferably human) light chains to select an Ebola virus GP-binding mAb, and then the new light chain is paired with a repertoire of (preferably human) heavy chains to select an (preferably human) Ebola virus GP-binding mAb having the same epitope as the archtypal mAb. Alternatively variants of the archetypal mAb can be obtained by mutagenesis of cDNA encoding the heavy and light chains of the antibody.

Epitope mapping, e.g., as described in Champe et al. (1995) J. Biol. Chem. 270:1388-1394, can be performed to determine whether the antibody binds an epitope of interest. "Alanine scanning mutagenesis," as described by Cunningham and Wells (1989) Science 244: 1081-1085, or some other form of point mutagenesis of amino acid residues in human Ebola virus GP may also be used to determine the functional epitope for an anti-GP antibody of the present invention. Mutagenesis studies, however, may also reveal amino acid residues that are crucial to the overall three-dimensional structure of Eboal virus GP but that are not directly involved in antibody-antigen contacts, and thus other methods may be necessary to confirm a functional epitope determined using this method.

The epitope bound by a specific antibody may also be determined by assessing binding of the antibody to peptides comprising fragments of Ebola virus GP. A series of overlapping peptides encompassing the sequence of Ebola virus GP may be synthesized and screened for binding, e.g. in a direct ELISA, a competitive ELISA (where the peptide is assessed for its ability to prevent binding of an antibody to Ebola virus GP bound to a well of a microtiter plate), or on a chip. Such peptide screening methods may not be capable of detecting some discontinuous functional epitopes, i.e. functional epitopes that involve amino acid residues that are not contiguous along the primary sequence of the Ebola virus GP polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in Ebola virus GP when free and when bound in a complex with an antibody of interest (Zinn-Justin et al. (1992) Biochemistry 31, 11335-11347; Zinn-Justin et al. (1993) Biochemistry 32, 6884-6891).

With regard to X-ray crystallography, crystallization may be accomplished using any of the known methods in the art (e.g. Giege et al. (1994) Acta Crystallogr. D50:339-350; McPherson (1990) Eur. J. Biochem. 189:1-23), including microbatch (e.g. Chayen (1997) Structure 5:1269-1274), hanging-drop vapor diffusion (e.g. McPherson (1976) J. Biol. Chem. 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) Meth. Enzymol. 114 & 115, H. W. Wyckoff et al., eds., Academic Press; U.S. Patent Application Publication No. 2004/0014194), and BUSTER (Bricogne (1993) Acta Cryst. D49:37-60; Bricogne (1997) Meth. Enzymol. 276A:361-423, Carter & Sweet, eds.; Roversi et al. (2000) Acta Cryst. D56:1313-1323), the disclosures of which are hereby incorporated by reference in their entireties.

Antibody competition assays, as described herein, can be used to determine whether an antibody "binds to the same epitope" as another antibody. Typically, competition of 50% or more, 60% or more, 70% or more, such as 70%, 71%, 72%, 73%, 74%, 75%, 80%, 85%, 90%, 95% or more, of an antibody known to interact with the epitope by a second antibody under conditions in which the second antibody is in excess and the first saturates all sites, is indicative that the antibodies "bind to the same epitope." To assess the level of competition between two antibodies, for example, radioimmunoassays or assays using other labels for the antibodies, can be used. For example, an Ebola virus GP antigen can be incubated with a saturating amount of a first anti-GP antibody or antigen-binding fragment thereof conjugated to a labeled compound (e.g., $^3$H, $^{125}$I, biotin, or rubidium) in the presence the same amount of a second unlabeled anti-GP antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 50% inhibition of binding of the labeled antibody in the presence of the blocking antibody compared to binding in the absence of the blocking antibody, then there is competition between the two antibodies of 50%. Thus, reference to competition between a first and second antibody of 50% or more, 60% or more, 70% or more, such as 70%, 71%, 72%, 73%, 74%, 75%, 80%, 85%, 90%, 95% or more, means that the first antibody inhibits binding of the second antibody (or vice versa) to the antigen by 50%, 60%, 70%, 71%, 72%, 73%, 74%, 75%, 80%, 85%, 90%, 95% or more (compared to binding of the antigen by the second antibody in the absence of the first antibody). Thus, inhibition of binding of a first antibody to an antigen by a second antibody of 50%, 60%, 70%, 71%, 72%, 73%, 74%, 75%, 80%, 85%, 90%, 95% or more indicates that the two antibodies bind to the same epitope.

Testing Antibodies for Therapeutic Efficacy in Animal Models

Animal models are effective for testing the therapeutic efficacy of antibodies against Ebola virus GP. In certain embodiments, rodents (i.e., mice) can be used for Ebola infection. Briefly, mice are challenged with a strain of mouse adapted Ebola virus (e.g., Ebola Zaire 1976) by intraperitoneal inoculation, approximately 300 times the dose lethal for 50% of adult mice. In certain embodiments, guinea pigs can be used for Ebola infection. Guinea pigs are challenged with guinea pig-adapted virus. Additionally, in certain embodiments, non-human primates are used as an animal model of infection, as described in the Example below. In all animal models, antibodies can be administered 24 or 48 hours after infection to test for therapeutic efficacy.

Immunotoxins, Immunoconjugates and Antibody Derivatives

In another embodiment, the antibodies of the present invention are linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells.

Techniques for conjugating such therapeutic moiety to antibodies are well known in the art.

The toxin component of the immunotoxin can be, for example, a chemotherapeutic agent, a toxin such as an enzymatically active toxin of bacterial, fungal, plant or animal origin, or fragments thereof, or a small molecule toxin.

Additional toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, Aleurites fordii proteins, dianthin proteins, phytolaca Americana proteins (PAPI, PAPII, and PAP-S), Momordica charantia inhibitor, curcin, crotin, sapaonaria, officinalis inhibitor, gelonin, saporin, mitogellin, restrictocin, phenomycin, enomycin, and the tricothcenes. Small molecule toxins include, for example, calicheamicins, maytansinoids, palytoxin and CC1065.

Antibodies of the invention also can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

For Ebola virus GP detection, the detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{ 1,2-dioxetane-3,2'-(5'-chloro)tricyclo{3.3.1.1 3,7}decan}-4-yl) phenyl phosphate (CSPD), as well as CDP and CDP-star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Compositions

In certain embodiments, the present invention provides a composition, e.g., a composition, containing one or more monoclonal antibodies described herein, formulated together with a carrier (e.g., a pharmaceutically acceptable carrier). In one embodiment, the compositions include a combination of multiple (e.g., two or more) isolated antibodies of the invention. Preferably, each of the antibodies of the composition binds to a distinct, pre-selected epitope of Ebola virus GP.

Pharmaceutical compositions of the invention also can be administered in combination therapy, i.e., combined with other agents. For example, the combination therapy can include a composition of the present invention with at least one or more additional therapeutic agents. Co-administration with other antibodies is also encompassed by the invention.

As used herein, the terms "carrier" and "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, e.g., antibody, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) *J. Neuroimmunol.* 7:27).

Carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous or intramuscular injection or once or twice monthly by subcutaneous or intramuscular injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in certain embodiments, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p 120 (Schreier et al. (1994) *J. Biol. Chem.* 269: 9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in certain embodiments, the liposomes include a targeting moiety. In certain embodiments, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Uses and Methods of the Invention

In certain embodiments, the antibodies, bispecific molecules, and compositions of the present invention can be used to treat and/or prevent (e.g., immunize against) Ebola virus infection in a subject. In other aspects, the antibodies, and compositions of the present invention can be used to detect Ebola virus infection in a sample.

For use in therapy, the antibodies of the invention can be administered to a subject directly (i.e., in vivo), either alone or with other therapies such as an immunostimulatory agent. In all cases, the antibodies, compositions, and immunostimulatory agents and other therapies are administered in an effective amount to exert their desired therapeutic effect. The term "effective amount" refers to that amount necessary or sufficient to realize a desired biologic effect. One of ordinary skill in the art can empirically determine the effective amount of a particular molecule without necessitating undue experimentation.

Additionally, in certain embodiments, these optimized antibodies can be combined with monoclonal antibodies against Ebola virus glycoprotein characterized in U.S. Pat. No. 6,630,144, Olinger et al., *PNAS* 2012; 109, 18030-18035, and Pettitt et al., *Sci Transl Med* 2013; 5, 199ra113.

Preferred routes of administration for vaccines include, for example, injection (e.g., subcutaneous, intravenous, parenteral, intraperitoneal, intrathecal). The injection can be in a bolus or a continuous infusion. Other routes of administration include oral administration.

Antibodies of the invention also can be coadministered with adjuvants and other therapeutic agents. It will be appreciated that the term "coadministered" as used herein includes any or all of simultaneous, separate, or sequential administration of the antibodies and conjugates of the present invention with adjuvants and other agents, including administration as part of a dosing regimen. The antibodies are typically formulated in a carrier alone or in combination with such agents. Examples of such carriers include solutions, solvents, dispersion media, delay agents, emulsions and the like. The use of such media for pharmaceutically active substances is well known in the art. Any other conventional carrier suitable for use with the molecules falls within the scope of the instant invention.

The present invention is further illustrated by the following examples which should not be construed as further limiting. The contents of Sequence Listing, figures and all references, patents and published patent applications cited throughout this application are expressly incorporated herein by reference.

Antibody Combinations

In certain embodiments, a subject is administered a pharmaceutical composition comprising one or more antibodies or antigen binding fragments of the invention with a pharmaceutically acceptable carrier. In some embodiments, a combination of antibodies is formulated with a pharmaceutically acceptable carrier in a single pharmaceutical composition. In other embodiments, each antibody is formulated with a pharmaceutically acceptable carrier and a combination or two or more pharmaceutical compositions is administered to a subject.

In certain embodiments of the invention, a combination of two, three, or more antibodies is selected from the group consisting of the antibodies set forth in Table 1 and Table 2. In certain embodiments, three antibodies from Table 1 or Table 2 are formulated with a pharmaceutically acceptable carrier in a single pharmaceutical composition. In certain embodiments, the combination is administered to a subject for treatment of an Ebola virus infection. In other embodiments, each antibody from Table 1 or Table 2 is formulated with a pharmaceutically acceptable carrier and a combination or two or more pharmaceutical compositions is administered to a subject. The subject can be administered a composition comprising the antibodies disclosed herein alone or in combination, along with a therapeutic agent. In certain embodiments, the therapeutic agent is interferon-alpha. The combinations described herein may be more effective at neutralizing Ebola virus.

Peptides and Compositions Based on Ebola Virus Glycoprotein (GP) Epitopes

To facilitate the engineering of antibodies that target the Ebola virus glycoprotein (GP), epitope hotspots were determined using alanine scanning, as described herein. Based on the binding analysis, antibodies 4G7, K252, and 2G4 were found to bind to a conformational epitope that included regions V505-C511 and N550-E564 of SEQ ID NO: 91, whereas antibody 13C6 was found to bind within the regions T270-P279 and Y394-R409 of SEQ ID NO: 91 (FIG. 1). FIG. 2 summarizes the hotspots in the Ebola virus glycoprotein identified through this mutational analysis.

Peptides or peptide mimetics based on one or more epitopes within Ebola virus glycoprotein include region V505-C511, region N550-E564, region T270-P279, or region Y394-R404 of Ebola virus glycoprotein (SEQ ID NO: 91). Other peptide or peptide mimetics based on one or more epitopes Ebola virus glycoprotein include TGKLIWKVNP (SEQ ID NO: 98), YKLDISEATQVGQHHR (SEQ ID NO: 99), VNAQPKC (SEQ ID NO: 100), and NQDGLICGLRQLANE (SEQ ID NO: 101).

Generally, peptides for use as immunogens range in size from about 10 to about 50 amino acid residues in length, more preferably from about 15 to about 30 amino acid residues, and in particular, is about 20 amino acid residues in length.

A peptide of the invention can be readily modified to include at least one conservative amino acid substitution, and at any position. Preferably, that peptide specifically binds to an anti-Ebola monoclonal antibody as described herein. Peptides of the invention are chemically synthesized in vitro using known techniques.

The peptides described above are formulated into vaccine compositions. These vaccine compositions may be employed to immunize an animal in order to elicit a highly anti-Ebola antibody immune response. Vaccine compositions are also useful to administer to subjects in need thereof to induce a protective immune response. Such vaccine compositions are well known to the art and include, for example, physiologically compatible buffers, preservatives, and saline and the like, as well as adjuvants.

"Adjuvants" are agents that nonspecifically increase an immune response to a particular antigen, thus reducing the quantity of antigen necessary in any given vaccine, and/or the frequency of injection necessary in order to generate an adequate immune response to the antigen of interest. Suitable adjuvants for the vaccination of animals include, but are not limited to, Adjuvant 65 (containing peanut oil, mannide monooleate and aluminum monostearate); Freund's complete or incomplete adjuvant; mineral gels, such as aluminum hydroxide, aluminum phosphate and alum; surfactants, such as hexadecylamine, octadecylamine, lysolecithin, dimethyldioctadecylammonium bromide, N,N-dioctadecyl-N', N'-bis(2-hydroxymethyl) propanediamine, methoxyhexadecylglycerol and pluronic polyols; polyanions, such as pyran, dextran sulfate, poly IC, polyacrylic acid and carbopol; peptides, such as muramyl dipeptide, dimethylglycine and tuftsin; and oil emulsions. The protein or peptides could also be administered following incorporation into liposomes or other microcarriers. Information concerning adjuvants and various aspects of immunoassays are disclosed, e.g., in the series by P. Tijssen, Practice and Theory of Enzyme Immunoassays, 3rd Edition, 1987, Elsevier, N.Y., incorporated by reference herein.

The vaccine composition includes a sufficient amount of the desired immunogen, such as the peptides of the invention, to elicit an immune response. The amount administered can range from about 0.0001 g/kg to about 1.0 g/kg, relative to the mass of the animal. Any suitable vertebrate animal is readily employed to obtain polyclonal antiserum. Preferably, the animal is a mammal, and includes, but is not limited to, rodents, such as a mice, rats, rabbits, horses, canines, felines, bovines, ovines, e.g., goats and sheep, primates, e.g., monkeys, great apes and humans, and the like.

The vaccine composition is readily administered by any standard route, including intravenously, intramuscularly, subcutaneously, intraperitoneally, and/or orally. The artisan will appreciate that the vaccine composition is preferably formulated appropriately for each type of recipient animal and route of administration.

Other aspects of the invention relate to methods of treating or preventing of Ebola virus infection by administering to a subject in need thereof an effective amount of a vaccine according to the invention.

Other Embodiments

The invention described herein pertains to antibodies directed towards Ebola virus glycoprotein (GP). In one aspect, the invention relates to an isolated monoclonal antibody, or antigen binding portion thereof, which specifically binds to Ebola virus glycoprotein, comprises a variable heavy chain and a variable light chain selected from the group consisting of:
(a) SEQ ID NOs: 15 and 17;
(b) SEQ ID NOs: 15 and 18;
(c) SEQ ID NOs: 16 and 17;
(d) SEQ ID NOs: 16 and 18;
(e) SEQ ID NOs: 19 and 20;
(f) SEQ ID NOs: 19 and 21;
(g) SEQ ID NOs: 22 and 23;
(h) SEQ ID NOs: 22 and 24;
(i) SEQ ID NOs: 9 and 10;
(j) SEQ ID NOs: 9 and 27;
(k) SEQ ID NOs: 9 and 28;
(l) SEQ ID NOs: 9 and 29;
(m) SEQ ID NOs: 9 and 30;
(n) SEQ ID NOs: 9 and 31;
(o) SEQ ID NOs: 25 and 10;
(p) SEQ ID NOs: 25 and 27;
(q) SEQ ID NOs: 25 and 28;
(r) SEQ ID NOs: 25 and 29;
(s) SEQ ID NOs: 25 and 30;
(t) SEQ ID NOs: 25 and 31;
(u) SEQ ID NOs: 26 and 10;
(v) SEQ ID NOs: 26 and 27;
(w) SEQ ID NOs: 26 and 28;
(x) SEQ ID NOs: 26 and 29;
(y) SEQ ID NOs: 26 and 30;
(z) SEQ ID NOs: 26 and 31;
(aa) SEQ ID NOs: 11 and 12;
(bb) SEQ ID NOs: 11 and 36;
(cc) SEQ ID NOs: 11 and 37;
(dd) SEQ ID NOs: 32 and 12;
(ee) SEQ ID NOs: 32 and 36;
(ff) SEQ ID NOs: 32 and 37;
(gg) SEQ ID NOs: 33 and 12;
(hh) SEQ ID NOs: 33 and 36;
(ii) SEQ ID NOs: 33 and 37;
(jj) SEQ ID NOs: 34 and 12;
(kk) SEQ ID NOs: 34 and 36;
(ll) SEQ ID NOs: 34 and 37;
(mm) SEQ ID NOs: 35 and 12:
(nn) SEQ ID NOs: 35 and 36;
(oo) SEQ ID NOs: 35 and 37;
(pp) SEQ ID NOs: 13 and 14;
(qq) SEQ ID NOs: 13 and 42;
(rr) SEQ ID NOs: 13 and 43;
(ss) SEQ ID NOs: 13 and 44;
(tt) SEQ ID NOs: 38 and 14;
(uu) SEQ ID NOs: 38 and 42;
(vv) SEQ ID NOs: 38 and 43;
(ww) SEQ ID NOs: 38 and 44;
(xx) SEQ ID NOs: 39 and 14;
(yy) SEQ ID NOs: 39 and 42;
(zz) SEQ ID NOs: 39 and 43;
(aaa) SEQ ID NOs: 39 and 44;
(bbb) SEQ ID NOs: 40 and 14;
(ccc) SEQ ID NOs: 40 and 42;
(ddd) SEQ ID NOs: 40 and 43;
(eee) SEQ ID NOs: 40 and 44;
(fff) SEQ ID NOs: 41 and 14;
(ggg) SEQ ID NOs: 41 and 42;
(hhh) SEQ ID NOs: 41 and 43; and
(iii) SEQ ID NOs: 41 and 44.

Certain aspects of the invention relate to an isolated monoclonal antibody, or antigen binding portion thereof, which binds to Ebola virus glycoprotein and comprises heavy and light chain variable regions, wherein the heavy chain variable region comprises an amino acid sequence which is at least 90% identical to the amino acid sequence is selected from the group consisting of SEQ ID NOs: 9, 11, 13, 15, 16, 19, 22, 25, 26, 32, 33, 34, 35, 38, 39, 40, and 41.

In another aspect, the invention relates to an isolated monoclonal antibody, or antigen binding portion thereof, which binds to Ebola virus glycoprotein and comprises heavy and light chain variable regions, wherein the light chain variable region comprises an amino acid sequence which is at least 90% identical to the amino acid sequence is selected from the group consisting of SEQ ID NOs: 10, 12, 14, 17, 18, 20, 21, 23, 24, 27, 28, 29, 30, 31, 36, 37, 42, 43, and 44.

In a further aspect, the invention relates to an isolated monoclonal antibody, or antigen binding portion thereof, which binds to Ebola virus glycoprotein and comprises heavy chain and light chain sequences is at least 80%, 85%, 90%, 95%, 96%, 97%, 98%, or 99% identical to the amino acid sequences selected from the group consisting of:
(a) SEQ ID NOs: 15 and 17, respectively;
(b) SEQ ID NOs: 15 and 18, respectively;
(c) SEQ ID NOs: 16 and 17, respectively;
(d) SEQ ID NOs: 16 and 18, respectively;
(e) SEQ ID NOs: 19 and 20, respectively;
(f) SEQ ID NOs:19 and 21, respectively;
(g) SEQ ID NOs: 22 and 23, respectively;
(h) SEQ ID NOs: 22 and 24, respectively;
(i) SEQ ID NOs: 9 and 10, respectively;
(j) SEQ ID NOs: 9 and 27, respectively;
(k) SEQ ID NOs: 9 and 28, respectively;
(l) SEQ ID NOs: 9 and 29, respectively;
(m) SEQ ID NOs: 9 and 30, respectively;
(n) SEQ ID NOs: 9 and 31, respectively;
(o) SEQ ID NOs: 25 and 10, respectively;
(p) SEQ ID NOs: 25 and 27, respectively;
(q) SEQ ID NOs: 25 and 28, respectively;
(r) SEQ ID NOs: 25 and 29, respectively;
(s) SEQ ID NOs: 25 and 30, respectively;
(t) SEQ ID NOs: 25 and 31, respectively;
(u) SEQ ID NOs: 26 and 10, respectively;
(v) SEQ ID NOs: 26 and 27, respectively;
(w) SEQ ID NOs: 26 and 28, respectively;
(x) SEQ ID NOs: 26 and 29, respectively;
(y) SEQ ID NOs: 26 and 30, respectively;
(z) SEQ ID NOs: 26 and 31, respectively;
(aa) SEQ ID NOs: 11 and 12, respectively;
(bb) SEQ ID NOs: 11 and 36, respectively;
(cc) SEQ ID NOs: 11 and 37, respectively;
(dd) SEQ ID NOs: 32 and 12, respectively;
(ee) SEQ ID NOs: 32 and 36, respectively;
(ff) SEQ ID NOs: 32 and 37, respectively;
(gg) SEQ ID NOs: 33 and 12, respectively;
(hh) SEQ ID NOs: 33 and 36, respectively;
(ii) SEQ ID NOs: 33 and 37, respectively;
(jj) SEQ ID NOs: 34 and 12, respectively;
(kk) SEQ ID NOs: 34 and 36, respectively;
(ll) SEQ ID NOs: 34 and 37, respectively;
(mm) SEQ ID NOs: 35 and 12, respectively;
(nn) SEQ ID NOs: 35 and 36, respectively;
(oo) SEQ ID NOs: 35 and 37, respectively;
(pp) SEQ ID NOs: 13 and 14, respectively;
(qq) SEQ ID NOs: 13 and 42, respectively;
(rr) SEQ ID NOs: 13 and 43, respectively;
(ss) SEQ ID NOs: 13 and 44, respectively;
(tt) SEQ ID NOs: 38 and 14, respectively;
(uu) SEQ ID NOs: 38 and 42, respectively;
(vv) SEQ ID NOs: 38 and 43, respectively;
(ww) SEQ ID NOs: 38 and 44, respectively;
(xx) SEQ ID NOs: 39 and 14, respectively;
(yy) SEQ ID NOs: 39 and 42, respectively;
(zz) SEQ ID NOs: 39 and 43, respectively;
(aaa) SEQ ID NOs: 39 and 44, respectively;
(bbb) SEQ ID NOs: 40 and 14, respectively;
(ccc) SEQ ID NOs: 40 and 42, respectively;
(ddd) SEQ ID NOs: 40 and 43, respectively;
(eee) SEQ ID NOs: 40 and 44, respectively;
(fff) SEQ ID NOs: 41 and 14, respectively;
(ggg) SEQ ID NOs: 41 and 42, respectively;
(hhh) SEQ ID NOs: 41 and 43, respectively; and
(iii) SEQ ID NOs: 41 and 44, respectively.

In certain embodiments, the preceding antibody, or antigen binding portion thereof comprises heavy and light chain variable regions comprising an amino acid sequence at least 90% identical to the heavy and light chain variable regions selected from the group consisting of (a)-(iii). In certain embodiments, antibody, or antigen binding portion thereof comprises an amino acid sequence at least 95% identical to the heavy and light chain variable regions selected from the group consisting of (a)-(iii). In another embodiment, the antibody, or antigen binding portion thereof comprises a heavy and light chain variable region comprising an amino acid sequence at least 90% identical to the heavy and light chain variable regions selected from the group consisting of (a)-(iii).

In a further embodiment, the antibody is selected from the group consisting of an IgG1, an IgG2, an IgG3, an IgG4, an IgM, an IgA1, an IgA2, an IgD, and an IgE antibody. In an even further embodiment, the antibody, or antigen binding portion thereof is an IgG1 antibody.

Another aspect of the invention relates to an isolated monoclonal antibody that competes for binding to Ebola virus GP with an antibody described herein.

In a further aspect, the invention relates to a pharmaceutical composition comprising a monoclonal antibody or antigen binding portion thereof of and a pharmaceutically acceptable carrier. In certain embodiments the pharmaceutical composition comprises one or more of the monoclonal antibodies (a combination of monoclonal antibodies) or antigen binding portions thereof of and a pharmaceutically acceptable carrier. In one embodiment, a combination of antibodies is formulated with a pharmaceutically acceptable carrier in a single pharmaceutical composition. In another embodiment, each antibody is formulated with a pharmaceutically acceptable carrier and two or more pharmaceutical compositions with one or more antibodies is administered to a subject.

One aspect of the invention relates to a method for treating Ebola virus infection comprising administering an effective amount of the pharmaceutical compositions described above. In a further embodiment, the method further comprises administering a therapeutic agent. In certain embodiments the therapeutic agent is interferon alpha.

In another aspect, the invention relates to an isolated monoclonal antibody, or antigen binding portion thereof, which binds to Ebola virus glycoprotein, comprises a heavy chain comprising CDR1, CDR2, and CDR3, sequences set forth in SEQ ID NOs: 68, 69, and 70, respectively, and variable region framework residues selected from the group consisting of 49H, 71H, or a combination thereof (Kabat numbering convention) from the heavy chain variable region set forth in SEQ ID NO: 92, wherein the remainder of the heavy chain is from a human immunoglobulin; and a light chain comprising CDR1, CDR2, and CDR3 sequences set forth in SEQ ID NOs: 71, 72, and 73, respectively, and variable region framework residues selected from the group consisting of 42 L, 59 L, 70 L, 99 L, or a combination thereof (Kabat numbering convention) from the light chain variable region set forth in SEQ ID NO: 93, wherein the remainder of the light chain is from a human immunoglobulin.

In certain embodiments, the preceding antibody, or antigen binding portion thereof comprises variable region framework residue 49G (Kabat numbering convention). In certain embodiments, the preceding antibody, or antigen binding portion thereof comprises variable region framework residue 71T (Kabat numbering convention). In certain embodiments, the preceding antibody, or antigen binding portion thereof comprises variable region framework residue 42S (Kabat numbering convention). In certain embodiments, the preceding antibody, or antigen binding portion thereof comprises variable region framework residues 59V, 70Y, and 99G (Kabat numbering convention).

In another aspect, the invention relates to an isolated monoclonal antibody, or antigen binding portion thereof, which binds to Ebola virus glycoprotein, comprises a heavy chain comprising CDR1, CDR2, and CDR3 sequences set forth in SEQ ID NOs: 74, 75, and 76, respectively, and variable region framework residues selected from the group consisting of 49H, 50H, or a combination thereof (Kabat numbering convention) from the heavy chain variable region set forth in SEQ ID NO: 94, wherein the remainder of the heavy chain is from a human immunoglobulin; and a light chain comprising CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In certain embodiments, the preceding antibody, or antigen binding portion thereof comprises variable region framework residues 49A and 50E (Kabat numbering convention). In certain embodiments the preceding antibody, or antigen binding portion thereof comprises variable region framework residues 43S, 45Q, and 100G (Kabat numbering convention). In certain embodiments, the preceding antibody, or antigen binding portion thereof comprises variable region framework residues 3V, 70Q, and 71Y (Kabat numbering convention).

Another aspect of the invention relates to an isolated monoclonal antibody, or antigen binding portion thereof, which binds to Ebola virus glycoprotein, comprising a heavy chain comprising CDR1, CDR2, and CDR3 sequences set forth in SEQ ID NOs: 74, 77, and 78, respectively, wherein the remainder of the heavy chain is from a human immunoglobulin; and a light chain comprising CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In certain embodiments, the preceding antibody, or antigen binding portion thereof comprises variable region framework residues 43S, 45Q, and 100G (Kabat numbering convention). In certain embodiments the preceding antibody, or antigen binding portion thereof comprises variable region framework residues 3V, 70Q, and 71Y (Kabat numbering convention).

In another aspect of the invention relates to an isolated monoclonal antibody, or antigen binding portion thereof, which binds to Ebola virus glycoprotein, comprise a heavy chain comprising CDR1, CDR2, and CDR3 sequences set forth in SEQ ID NOs: 74, 77, and 79, respectively, wherein the remainder of the heavy chain is from a human immunoglobulin; and a light chain comprising CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin.

In certain embodiments the preceding antibody, or antigen binding portion thereof comprises variable region framework residues 43S, 45Q, and 100G (Kabat numbering convention). In certain embodiments, the preceding antibody, or antigen binding portion thereof comprises variable region framework residues 3V, 70Q, and 71Y (Kabat numbering convention).

In another aspect, the invention relates to an isolated monoclonal antibody, or antigen binding portion thereof, which binds to Ebola virus glycoprotein, comprises a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 88, and 89 respectively, and variable region framework residues selected from the group consisting of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the preceding antibody, or antigen binding portion thereof comprises variable region framework residue 44S (Kabat numbering convention). In certain embodiments, the preceding antibody, or antigen binding portion thereof comprises variable region framework residues 48I, 70 L, and 72V (Kabat numbering convention). In certain embodiments, the preceding antibody, or antigen binding portion thereof comprises variable region framework residue 50V (Kabat numbering convention). In certain embodiments, the preceding antibody, or antigen binding portion thereof comprises variable region framework residues 43S and 87F (Kabat numbering convention). In certain embodiments, the preceding antibody, or antigen binding portion thereof comprises variable region framework residues 3V, 70Q, 72S, 73 L, and 100S (Kabat numbering convention).

In another aspect, the invention relates to an isolated monoclonal antibody, or antigen binding portion thereof, which binds to Ebola virus glycoprotein, comprises a heavy chain comprising CDR1, CDR2, and CDR3 sequences set forth in SEQ ID NOs: 86, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 88, and 89 respectively, and variable region framework residues selected from the group consisting of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the preceding antibody, or antigen binding portion thereof comprises variable region framework residue 44S (Kabat numbering convention). In certain embodiments, the preceding antibody, or antigen binding portion thereof comprises variable region framework residues 48I, 70 L, and 72V (Kabat numbering convention). In certain embodiments, the preceding antibody, or antigen binding portion thereof comprises variable region framework residue 50V (Kabat numbering convention). In certain embodiments, the preceding antibody, or antigen binding portion thereof comprises variable region framework residues 43S and 87F (Kabat numbering convention). In certain embodiments, the preceding antibody, or antigen binding portion thereof comprises variable region framework residues 3V, 70Q, 72S, 73 L, and 100S (Kabat numbering convention).

In another aspect, the invention relates to an isolated monoclonal antibody, or antigen binding portion thereof, which binds to Ebola virus glycoprotein, comprises a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96 wherein the remainder of the heavy chain is from a human immunoglobulin; and a light chain comprising CDR1, CDR2, and CDR3 sequences set forth in SEQ ID NOs: 87, 90, and 89, respectively, and variable region framework residues selected from the group consisting of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the preceding antibody, or antigen binding portion thereof comprises variable region framework residue 44S (Kabat numbering convention). In certain embodiments, the preceding antibody, or antigen binding portion thereof comprises variable region framework residues 48I, 70 L, and 72V (Kabat numbering convention). In certain embodiments, the preceding antibody, or antigen binding portion thereof comprises variable region framework residue 50V (Kabat numbering convention). In certain embodiments, the preceding antibody, or antigen binding portion thereof comprises variable region framework residues 43S and 87F (Kabat numbering convention). In certain embodiments, the preceding antibody, or antigen binding portion thereof comprises variable region framework residues 3V, 70Q, 72S, 73 L, and 100S (Kabat numbering convention).

In another aspect, the invention relates to an isolated monoclonal antibody, or antigen binding portion thereof, which binds to Ebola virus glycoprotein, comprises a heavy chain comprising CDR1, CDR2, and CDR3 sequences set forth in SEQ ID NOs: 86, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and a light chain comprising CDR1, CDR2, and CDR3 sequences set forth in SEQ ID NOs: 87, 90, and 89, respectively, and variable region framework residues selected from the group consisting of 3 L, 43 L, 70 L, 72 L, 73 L, 87 L, 100 L, or a combination thereof (Kabat numbering convention) from the light chain variable region set forth in SEQ ID NO: 97, wherein the remainder of the light chain is from a human immunoglobulin.

In certain embodiments, the preceding antibody, or antigen binding portion thereof comprises variable region framework residue 44S (Kabat numbering convention). In certain embodiments, the preceding antibody, or antigen binding portion thereof comprises variable region framework residues 48I, 70 L, and 72V (Kabat numbering convention). In certain embodiments, the preceding antibody, or antigen binding portion thereof comprises variable region framework residue 50V (Kabat numbering convention). In certain embodiments, the preceding antibody, or antigen binding portion thereof comprises variable region framework residues 43S and 87F (Kabat numbering convention). In certain embodiments, the preceding antibody, or antigen binding portion thereof comprises variable region framework residues 3V, 70Q, 72S, 73 L, and 100S (Kabat numbering convention).

In another aspect, the invention relates to an isolated monoclonal antibody, or antigen binding portion thereof, which binds to Ebola virus glycoprotein, comprises:
  a) heavy chain CDR1, CDR2, and CDR3 sequences comprising SEQ ID NOs: 45, 46, and 47, respectively, and light chain CDR1, CDR2, and CDR3 sequences comprising SEQ ID NOs: 48, 50, and 51 respectively;
  b) heavy chain CDR1, CDR2, and CDR3 sequences comprising SEQ ID NOs: 52, 53, and 54, respectively, and light chain CDR1, CDR2, and CDR3 sequences comprising SEQ ID NOs: 55, 56, and 58 respectively;
  c) heavy chain CDR1, CDR2, and CDR3 sequences comprising SEQ ID NOs: 52, 53, and 54, respectively, and light chain CDR1, CDR2, and CDR3 sequences comprising SEQ ID NOs: 55, 56, and 59, respectively;
  d) heavy chain CDR1, CDR2, and CDR3 sequences comprising SEQ ID NOs: 60, 61, and 63, respectively, and light chain CDR1, CDR2, and CDR3 sequences comprising SEQ ID NOs: 64, 65, and 67, respectively;
  e) heavy chain CDR1, CDR2, and CDR3 sequences comprising SEQ ID NOs: 74, 77, and 78, respectively, and light chain CDR1, CDR2, and CDR3 sequences comprising SEQ ID NOs: 80, 81, and 82, respectively;
  f) heavy chain CDR1, CDR2, and CDR3 sequences comprising SEQ ID NOs: 74, 77, and 79, respectively, and light chain CDR1, CDR2, and CDR3 sequences comprising SEQ ID NOs: 80, 81, and 82, respectively;
  g) heavy chain CDR1, CDR2, and CDR3 sequences comprising SEQ ID NOs: 83, 84 and 85, respectively, and light chain CDR1, CDR2, and CDR3 sequences comprising SEQ ID NOs: 87, 90 and 89, respectively;
  h) heavy chain CDR1, CDR2, and CDR3 sequences comprising SEQ ID NOs: 86, 84, and 85, respectively, and light chain CDR1, CDR2, and CDR3 sequences comprising SEQ ID NOs: 87, 88, and 89, respectively; or
  i) heavy chain CDR1, CDR2, and CDR3 sequences comprising SEQ ID NOs: 86, 84, and 85, respectively, and light chain CDR1, CDR2, and CDR3 sequences comprising SEQ ID NOs: 87, 90, and 89, respectively.

One aspect of the invention is a pharmaceutical composition comprising the preceding antibody or antigen binding portion thereof and a pharmaceutically acceptable carrier.

A further aspect of the invention is a pharmaceutical composition comprising one or more of the preceding antibodies or antigen binding positions thereof and a pharmaceutically acceptable carrier.

One aspect of the invention is a method for treating Ebola virus infection comprising administering an effective amount of the pharmaceutical compositions described herein. In certain embodiments the method includes administering a therapeutic agent. In certain embodiments, the therapeutic agent is interferon alpha.

EXAMPLES

The examples below utilize monoclonal antibodies of the invention which have been optimized based on previously characterized mouse monoclonal antibodies 1H3, 2G4, and 4G7 (U.S. Pat. No. 8,513,391, Qiu et al., *Sci Transl Med* 2012; 4, 138ra81, and Qiu et al., *Clin Immunol* 2011; 141, 218-227, herein incorporated by reference)), and mouse monoclonal antibodies 13C6, 6D8, and 13F6 (U.S. Pat. Nos. 6,630,144 and 7,335,356, herein incorporated by reference).

Example 1

Epitope Mapping of the Ebola Virus Glycoprotein

To facilitate the engineering of antibodies that target the Ebola virus glycoprotein (GP), epitope hotspots were determined using alanine scanning, as described below.

GP Expression Platform

A GP expression platform that allows for alanine mutations to be made and for their binding properties to be assayed was first established. A pcDNA 3.3 expression vector containing a sequence encoding GPΔTMΔmuc (missing transmembrane and mucin domains) was transiently transfected into HEK 293F cells. After 6 days, supernatant was harvested and purified using a 1 mL HisTrap HP column on an AKTA FPLC (GE Healthcare). Fractions were collected and analyzed using Native PAGE (Invitrogen). Fractions containing trimeric GP species were combined and buffer exchanged into PBS using Amicon Ultra Centrifugation Filters (Millipore). Protein concentration was determined using a BCA assay (Pierce) and GP was assessed again using Native PAGE to confirm purity.

Site-Directed Mutagenesis for Alanine-Scanning Studies

GPΔTMΔmuc point mutants were created using site-directed mutagenesis. Mutagenesis primers were designed corresponding to the mutant sequence, and a PCR amplification reaction was carried out using a QuikChange Mutagenesis Kit (Agilent). PCR reactions were then digested using Dpn 1 for 3 hours, transformed into One Shot TOP10 Chemically Competent cells (Thermo) and then plated onto LB agar plates containing ampicillin. Plasmid DNA was generated by growing colonies in LB broth containing ampicillin overnight and then by purifying using Plasmid DNA preparation kits (Invitrogen). Positive colonies were confirmed using Sanger sequencing (Genewiz). The functional consequences of the alanine mutations were assessed by assaying the binding of various mAbs (e.g. 13C6, 2G4, 4G7) to the mutants. An ELISA was used wherein either the mutant or WT GP was coated on the plate and antibodies were added. Change in binding between the specific mutant and WT was analyzed to determine the effect of the mutation on binding.

Based on the binding analysis, antibodies 4G7, K252, and 2G4 were found to bind to a conformational epitope that included regions V505-C511 and N550-E564 of SEQ ID NO: 91, whereas antibody 13C6 was found to bind within the regions T270-P279 and Y394-R409 of SEQ ID NO: 91 (FIG. 1). FIG. 2 summarizes the hotspots in the glycoprotein identified through this mutational analysis.

Example 2

Binding Affinity of Ebola Glycoprotein-Specific Antibodies

Based on the epitope hostspot data from Example 1, antibodies from Table 1 were further selected based on their binding affinity to the Ebola virus glycoprotein using ELISA.

For the ELISA, 100 μL of Ebola GPd™ (IBT Bioservices) was plated onto a Maxisorp 96 well plate (Nunc) at a concentration of 1 μg/mL and left at 4° C. overnight. The following day, the plate was washed 3× with PBST (PBS+ 0.05% TWEEN-20 (polysorbate-20)) and 100 μL of 1% BSA in PBST was incubated for 1 hour at room temperature. The plate was then washed 3× and 100 μL of an antibody dilution series was added. For each antibody dilution series, the first well contained antibody at a concentration of 9 μg/mL, and then each well was a 3-fold dilution across an 11-point series (12$^{th}$ well was PBST). After antibody addition, plates were incubated for 2 hours at room temperature. Plates were then washed 3× and 100 μL secondary antibody (Rabbit anti-human IgG Fc with HRP, Jackson Immunoresearch) was added to each well at a dilution of 1:5000 (from 0.8 mg/mL stock) for 1 hour. Plates were then washed 3×, and 100 μL TMB microwell peroxidase (KPL) was added for 5 minutes before neutralization with 100 μL 1N H$_2$SO$_4$. Plates were then read using a SpectraMax M5e plate reader at 450 nm.

Figure 3A:
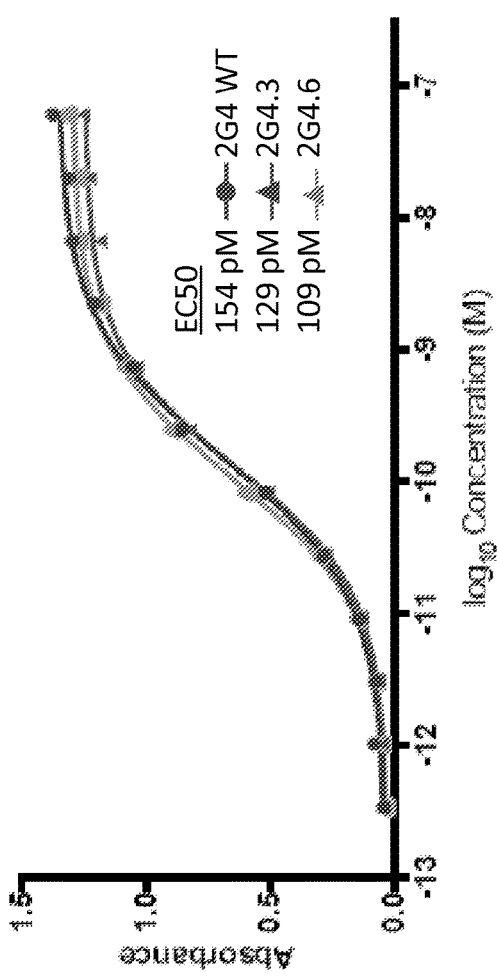
FIGS. 3A-3C are graphs showing the binding affinities of antibodies 2G4 (FIG. 3A), 4G7 (FIG. 3B), and 13C6 (FIG. 3C) for Ebola virus glycoprotein, as determined by ELISA. Both wild-type antibodies and related constructs are shown.
Figure 3B:
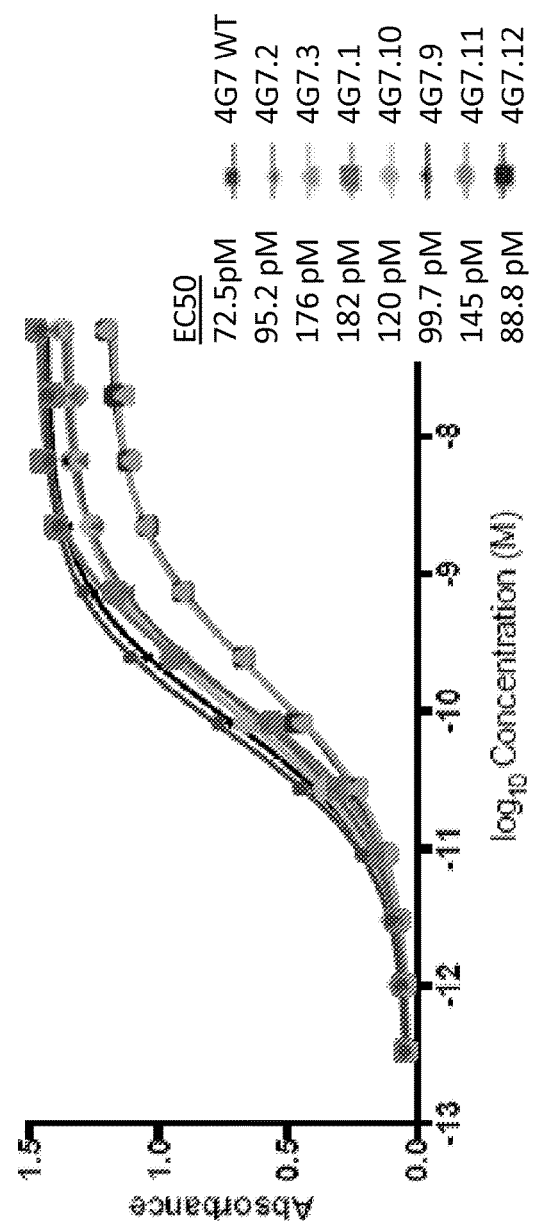
Figure 3C:
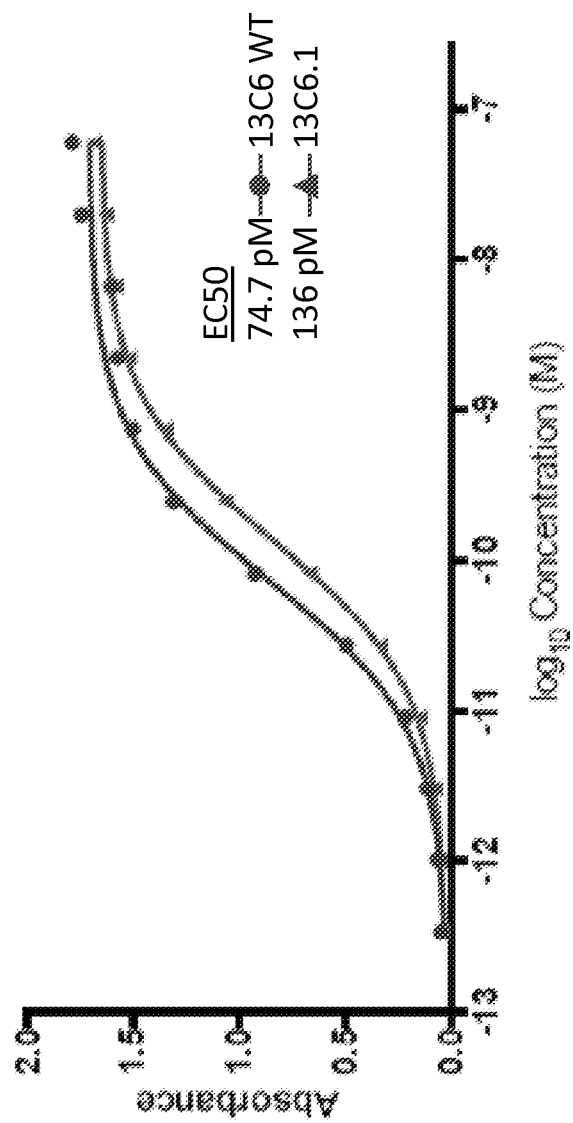
Figure 4:
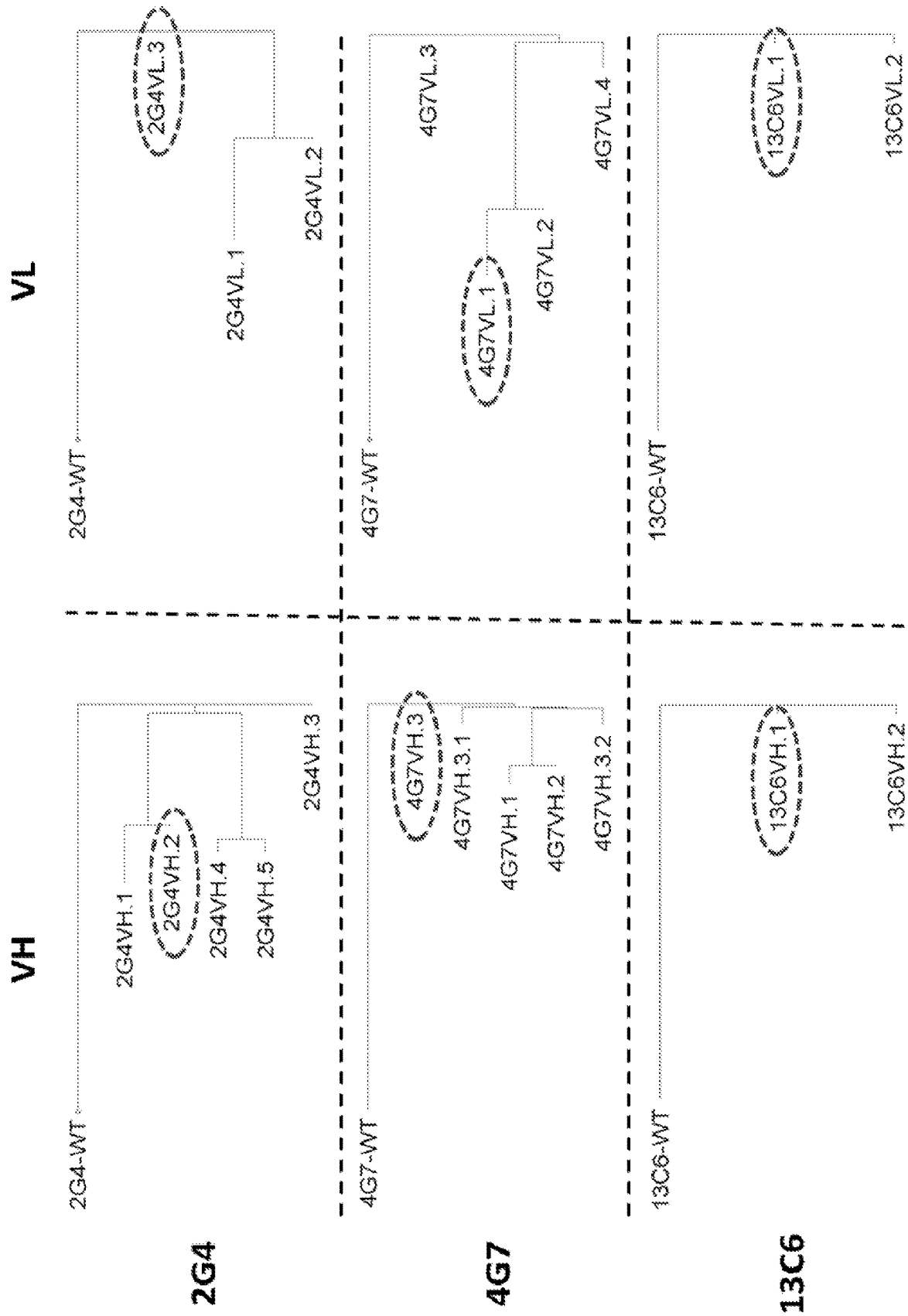
FIG. 4 is a phylogram of the variable region heavy chains (VH) and variable region light chains (VL) for antibodies 2G4, 4G7, and 13C6. The lead candidates are circled by dotted ovals.

FIGS. 3A-3C show the data generated from the ELISA. The data is a representation of different antibodies (13C6.X, 2G4.X, 4G7.X) from the screening process. The 2G4 antibodies tested were wild type (WT), 2G4.3, and 2G4.6, with EC50 values of 154 pM, 129 pM, and 109 pM, respectively (FIG. 3A). The 4G7 antibodies tested were Wt, 4G7.2, 4G7.3, 4G7.1, 4G7.10, 4G7.9, 4G7.11, and 4G7.12, with EC50 values of 72.5 pM, 95.2 pM, 176 pM, 182 pM, 120 pM, 99.7 pM, 145 pM, and 88.8 pM, respectively (FIG. 3B). The 13C6 antibodies tested were WT and 13C6.1, having EC50 values of 74.7 pM and 136 pM, respectively (FIG. 3C). These data show that the antibodies bound to Ebola glycoprotein with an EC50 of 200 pM or less, as measured by ELISA The candidates were generated using in silico antibody design, and the lead candidates were selected on the basis of binding affinity values. The phylogram shown in FIG. 4 illustrates the sequence similarity between the different antibodies. In each case, the lead candidate is circled in a dotted oval. For each candidate there is a large distance from the parent monoclonal antibody (WT). In addition, the in silico generated candidates cluster closely, illustrating the similarity between these candidates. Phylogeny trees were constructed for the representative antibody amino acid sequences by Neighbor-Joining method using Geneious (geneious.com/).

Example 3

Neutralization of Ebola Virus Glycoprotein by Optimized Monoclonal Antibodies

In order to determine if the anti-Ebola glycoprotein antibodies neutralize Ebola virus in vitro, purified mAbs were evaluated for their ability to inhibit plaque formation by various strains of Ebola virus as compared to plaques formation in the absence of the antibodies (i.e., control). Known amounts of antibody were mixed with 200 pfu of Ebola virus and incubated at 37° C. for 30 minutes. The virus/antibody mix was then added to a monolayer of vero E6 cells and allowed to adsorb for 30 minutes at 37° C. After this, the cells were washed twice with PBS and then overlayed with media containing 1% methyl cellulose. Cells were incubated for 4 days at 37° C. and then fixed with formalin for removal from BSL4 lab. Ebola virus infected plaques were visualized by IFA staining and the number of plaques in each well counted. Percent reduction in plaque number was calculated from wells with no serum. Titre is expressed as either 50 or 80% plaque reduction.

FIG. 5 shows the results of the neutralization assay. Antibody 13C6.1 neutralized each of the three Ebola strains at a concentration of greater than 50 µg/mL. Antibody 2G4.6 neutralized the three Ebola strains at concentrations of 2 to 4 µg/mL. Antibody 4G7.9 neutralized the three strains at a concentration of 1 µg/mL.

Example 4

In Vivo Non-Human Primate Study

Cynomolgus macaques are used to test whether and how effectively an anti-GP mAb can improve survival when administered after high-dose EBOV infection.

Ebola virus (EBOV) strain Kikwit 95 is produced on Vero E6 cells in complete minimal essential medium (cMEM), 2% FBS, and 1% penicillin/stretopmycin.

Macaques are randomized into groups on the basis of treatment regimens, plus one receiving only PBS as a positive control for infection. Each subject is infected with 1000 PFU (1 mL each into two sites intramuscularly) of EBOV in Dulbecco's modified Eagle's medium (DMEM). Half of the groups begin treatment 24 hours post infection and the other half of the groups begin treatment 48 hours post infection. The subjects are treated intravenously with one of the EBOV-GP-specific neutralizing antibodies disclosed herein at 25 mg/kg, or a mixture of antibodies disclosed herein, as a 5 mL slow bolus in the saphenous vein. The subjects are monitored daily and scored for disease progression with an internal filovirus scoring protocol. Changes in the subject's posture/activity, attitude, activity level, feces/urine output, food/water intake, weight, temperature, respiration, and scored disease manifestations such as a visible rash, hemorrhage, cyanosis, or flushed skin are scored. Tests for weight, temperature, blood, and oropharyngeal, nasal, and rectal swabs are taken at days 1, 4, 7, 14, 21, and 28 post infection for the 24-hour group or at 2, 5, 8, 14, 21, and 28 days post infection for the 48-hour group, before the animals receive the mAb or mAb mixture.

Example 5

Human Study

Humans infected with Ebola virus are administered a single anti-GP antibody disclosed herein, or a combination thereof. Ideally, the antibodies will be given 24 or 48 hours post infection. Subjects are monitored for disease manifestations such as visible rash, hemorrhage, cyanosis, or flushed skin. Viral titers are also be monitored.

EQUIVALENTS

Those skilled in the art will recognize, or be able to ascertain using no more than routine experimentation, many equivalents of the specific embodiments of the invention described herein. Such equivalents are intended to be encompassed by the following claims.

TABLE 1

Antibody Pairs by SEQ ID Number

| Antibody | VH | VL | VH CDR | | | VL CDR | | |
| --- | --- | --- | --- | --- | --- | --- | --- | --- |
| | | | CDR1 | CDR2 | CDR3 | CDR1 | CDR2 | CDR3 |
| 13C6.1 | 15 | 17 | 45 | 46 | 47 | 48 | 50 | 51 |
| 13C6.2 | 15 | 18 | 45 | 46 | 47 | 48 | 50 | 51 |
| 13C6.3 | 16 | 17 | 45 | 46 | 47 | 48 | 50 | 51 |
| 13C6.4 | 16 | 18 | 45 | 46 | 47 | 48 | 50 | 51 |
| 6D8.1 | 19 | 20 | 52 | 53 | 54 | 55 | 56 | 58 |
| 6D8.2 | 19 | 21 | 52 | 53 | 54 | 55 | 56 | 59 |
| 13F6.1 | 22 | 23 | 60 | 61 | 63 | 64 | 65 | 67 |
| 13F6.2 | 22 | 24 | 60 | 61 | 63 | 64 | 65 | 67 |
| 1H3.1 | 9 | 10 | 68 | 69 | 70 | 71 | 72 | 73 |
| 1H3.2 | 9 | 27 | 68 | 69 | 70 | 71 | 72 | 73 |
| 1H3.3 | 9 | 28 | 68 | 69 | 70 | 71 | 72 | 73 |
| 1H3.4 | 9 | 29 | 68 | 69 | 70 | 71 | 72 | 73 |
| 1H3.5 | 9 | 30 | 68 | 69 | 70 | 71 | 72 | 73 |
| 1H3.6 | 9 | 31 | 68 | 69 | 70 | 71 | 72 | 73 |
| 1H3.7 | 25 | 10 | 68 | 69 | 70 | 71 | 72 | 73 |
| 1H3.8 | 25 | 27 | 68 | 69 | 70 | 71 | 72 | 73 |
| 1H3.9 | 25 | 28 | 68 | 69 | 70 | 71 | 72 | 73 |
| 1H3.10 | 25 | 29 | 68 | 69 | 70 | 71 | 72 | 73 |
| 1H3.11 | 25 | 30 | 68 | 69 | 70 | 71 | 72 | 73 |
| 1H3.12 | 25 | 31 | 68 | 69 | 70 | 71 | 72 | 73 |
| 1H3.13 | 26 | 10 | 68 | 69 | 70 | 71 | 72 | 73 |
| 1H3.14 | 26 | 27 | 68 | 69 | 70 | 71 | 72 | 73 |
| 1H3.15 | 26 | 28 | 68 | 69 | 70 | 71 | 72 | 73 |
| 1H3.16 | 26 | 29 | 68 | 69 | 70 | 71 | 72 | 73 |
| 1H3.17 | 26 | 30 | 68 | 69 | 70 | 71 | 72 | 73 |
| 1H3.16 | 26 | 31 | 68 | 69 | 70 | 71 | 72 | 73 |
| 2G4.1 | 11 | 12 | 74 | 75 | 76 | 80 | 81 | 82 |
| 2G4.2 | 11 | 36 | 74 | 75 | 76 | 80 | 81 | 82 |
| 2G4.3 | 11 | 37 | 74 | 75 | 76 | 80 | 81 | 82 |
| 2G4.4 | 32 | 12 | 74 | 75 | 76 | 80 | 81 | 82 |
| 2G4.5 | 32 | 36 | 74 | 75 | 76 | 80 | 81 | 82 |
| 2G4.6 | 32 | 37 | 74 | 75 | 76 | 80 | 81 | 82 |
| 2G4.7 | 33 | 12 | 74 | 75 | 76 | 80 | 81 | 82 |

TABLE 1-continued

Antibody Pairs by SEQ ID Number

| Antibody | VH | VL | VH CDR | | | VL CDR | | |
| --- | --- | --- | --- | --- | --- | --- | --- | --- |
| | | | CDR1 | CDR2 | CDR3 | CDR1 | CDR2 | CDR3 |
| 2G4.8 | 33 | 36 | 74 | 75 | 76 | 80 | 81 | 82 |
| 2G4.9 | 33 | 37 | 74 | 75 | 76 | 80 | 81 | 82 |
| 2G4.10 | 34 | 12 | 74 | 77 | 78 | 80 | 81 | 82 |
| 2G4.11 | 34 | 36 | 74 | 77 | 78 | 80 | 81 | 82 |
| 2G4.12 | 34 | 37 | 74 | 77 | 78 | 80 | 81 | 82 |
| 2G4.13 | 35 | 12 | 74 | 77 | 79 | 80 | 81 | 82 |
| 2G4.14 | 35 | 36 | 74 | 77 | 79 | 80 | 81 | 82 |
| 2G4.15 | 35 | 37 | 74 | 77 | 79 | 80 | 81 | 82 |
| 4G7.1 | 13 | 14 | 83 | 84 | 85 | 87 | 88 | 89 |
| 4G7.2 | 13 | 42 | 83 | 84 | 85 | 87 | 88 | 89 |
| 4G7.3 | 13 | 43 | 83 | 84 | 85 | 87 | 88 | 89 |
| 4G7.4 | 13 | 44 | 83 | 84 | 85 | 87 | 90 | 89 |
| 4G7.5 | 38 | 14 | 83 | 84 | 85 | 87 | 88 | 89 |
| 4G7.6 | 38 | 42 | 83 | 84 | 85 | 87 | 88 | 89 |
| 4G7.7 | 38 | 43 | 83 | 84 | 85 | 87 | 88 | 89 |
| 4G7.8 | 38 | 44 | 83 | 84 | 85 | 87 | 90 | 89 |
| 4G7.9 | 39 | 14 | 83 | 84 | 85 | 87 | 88 | 89 |
| 4G7.10 | 39 | 42 | 83 | 84 | 85 | 87 | 88 | 89 |
| 4G7.11 | 39 | 43 | 83 | 84 | 85 | 87 | 88 | 89 |
| 4G7.12 | 39 | 44 | 83 | 84 | 85 | 87 | 90 | 89 |
| 4G7.13 | 40 | 14 | 83 | 84 | 85 | 87 | 88 | 89 |
| 4G7.14 | 40 | 42 | 83 | 84 | 85 | 87 | 88 | 89 |
| 4G7.15 | 40 | 43 | 83 | 84 | 85 | 87 | 88 | 89 |
| 4G7.16 | 40 | 44 | 83 | 84 | 85 | 87 | 90 | 89 |
| 4G7.17 | 41 | 14 | 86 | 84 | 85 | 87 | 88 | 89 |
| 4G7.18 | 41 | 42 | 86 | 84 | 85 | 87 | 88 | 89 |
| 4G7.19 | 41 | 43 | 86 | 84 | 85 | 87 | 88 | 89 |
| 4G7.20 | 41 | 44 | 86 | 84 | 85 | 87 | 90 | 89 |

TABLE 2

Summary Sequence Table

| SEQ ID Number | Description | Sequence |
| --- | --- | --- |
| 1 | Human IgG1 Heavy Chain | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 2 | Human IgG1 Light chain (kappa) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 3 | 13C6 $V_H$ Wild Type | QLTLKESGPGILKPSQTLSLTCSLSGFSLSTSGVGVGWFRQPSGKGLEWLALIVVWDDDKYYNPSLKSQLSISKDFSRNQVFLKISNVDIADTATYYCARRDPFGYDNAMGYWGQGTSVTVSS |
| 4 | 13C6 $V_L$ Wild Type | DIVMTQSQKFMSTSVGDRVSLTCKASQNVGTAVAWYQQKPGQSPKLLIYSASNRYTGVPDRFTGSGSGTDFTLTISNMQSEDLADYFCQQYSSYPLTFGAGTKLELR |
| 5 | 6D8 $V_H$ Wild Type | DVKLLESGGGLVQPGGSLKLSCAASGFDFSRYWMSWVRQAPGKGLEWIGEINPDSSTINYTPSLKDKFIISRDNAKNTLYLQMSKVRSEDTALYYCTRQGYGYNYWGQGTTLIVSS |
| 6 | 6D8 $V_L$ Wild Type | DVLLTQIPLSLPVSLGDQASISCRSSQSIVHSNGNTYLEWYLQKPGQSPKLLIYKASNRFSGVPDRFSGSGSGTDFTLKINRVEAEDLGVYYCLQGSHVPSTFGGGTKLEIK |
| 7 | 13F6 $V_H$ Wild Type | EVQVVESGGGLVKPGGSLKLSCAASGFAFSSYDMSWVRQTPEKRLEWVAYISRGGGYTYYPDTVKGRFTISRDNAKNTLYLQMSSLKSEDTAMYYCSRHIYYGSSHYYAMDYWGQGTSVTVSS |

TABLE 2-continued

Summary Sequence Table

| SEQ ID Number | Description | Sequence |
|---|---|---|
| 8 | 13F6 V$_L$ Wild Type | QLVLTQSSSASFSLGASAKLTCTLSRQHSTYTIEWYQQQPLKP PRYVMELKKDGSHSTGDGIPDRFSGSSSGADRYLSISNIQPEDE AIYICGVGDTIKEQFVYVFGGGTKVTVLG |
| 9 | 1H3V$_H$.1 | EVQLVESGGGLVQPGGSLRLSCTASGFNIKDTYIHWVRQAPG KGLEWVARIDPANGNTKYADSVKGRFTISADTSKNTAYLQM NSLRAEDTAVYYCARESRISTMLTTGYFDYWGQGTLVTVSS |
| 10 | 1H3V$_L$.1 | DIQMTQSPSTLSASVGDRVTITCSASSSVSYMYWYQQKPGKA PKLLIYDTSNLASGVPARFSGSGSGTEFTLTISSLQPDDFATYY CQQWSSYPYTFGQGTKVEVK |
| 11 | 2G4V$_H$.1 | EVQLLESGGGLVQPGGSLRLSCVASGFTFSNYWMNWVRQAP GKGLEWLGFIRLKSNNYATHYSASVKGRFTISRDKSKSTLYLQ MNTLQAEDSAIYYCTRGNGNYRAMDYWGQGTLVTVSS |
| 12 | 2G4V$_L$.1 | DIQMTQSPSSLSASVGDRVTITCRASENIYSSLAWYQQKPGKA PKLLVYSATILADGVPSRFSGSGSGTDFTLTISSLQPEDFATYY CQHFWGTPYTFGQGTKVEIK |
| 13 | 4G7V$_H$.1 | QVQLVQSGAEVKKPGSSVKVSCKASGSSFTGFSMNWVRQAP GQGLEWMGNIDTYYGGTTYNGKFKGRVTITADKSTSTAYME LSSLRSEDTAVYYCARSAYYGSTFAYWGQGTLVTVSS |
| 14 | 4G7V$_L$.1 | DIQMTQSPSSLSASVGDRVTITCRASENIYSYLAWYQQKPGKA PKLLVYNAKTLIEGVPSRFSGSGSGTDFTFTISSLQPEDIATYYC QHHFGTPFTFGQGTKVEIK |
| 15 | 13C6 V$_H$.1 (T56S) | QLTLKESGPTLVKPTQTLSLTCTFSGFSLSTSGVGVGWFRQPP GKALEWLALIWWDDDKYYSPSLKSRLTITKDTSKNQVVLTM TNMDPVDTATYYCARRDPFGYDNAMGYWGQGTTVTVSS |
| 16 | 13C6 V$_H$.2 (T56S) | QLTLKESGPTLVKPTQTLSLTCTFSGFSLSTSGVGVGWFRQPP GKALEWLALIWWDDDKYYGPSLKSRLTITKDTSKNQVVLTM TNMDPVDTATYYCARRDPFGYDNAMGYWGQGTTVTVSS |
| 17 | 13C6 V$_L$.1 | DIVMTQSPSFLSASVGDRVTITCKASQNVGTAVAWYQQKPGK APKLLIYSASNRYSGVPSRFSGSGSGTDFTLTISSLQPEDFATYF CQQYSSYPLTFGGGTKLEIK |
| 18 | 13C6 V$_L$.2 | DIVMTQSPSFLSASVGDRVTITCKASQNVGTAVAWYQQKPGK APKLLIYSASNRYSGVPSRFSGSGSGTDFTLTISSLQPEDFATYF CQQYSSYPLTFGGGTKLEIK |
| 19 | 6D8 V$_H$.3 | EVKLVESGGGLVQPGGSLRLSCAASGFDFSRYWMSWVRQAP GKGLVWVSEINPDSSTINYADSVKGRFTISRDNAKNTLYLQM NSLRAEDTAVYYCTRQGYGYNYWGQGTTVTVSS |
| 20 | 6D8 V$_L$.3 | DVLLTQSPLSLPVTLGQPASISCRSSQSIVHSNGNTYLEWYLQ KPGQSPRLLIYKASNRFSGVPDRFSGSGSGTDFTLKISRVEAED VGVYYCLNGSHVPSTFGGGTKVEIK |
| 21 | 6D8 V$_L$.4 | DVLLTQTPLSLPVTLGQPASISCRSSQSIVHSNGNTYLEWYLQ KPGQSPQLLIYKASNRFSGVPDRFSGSGSGTDFTLKISRVEAED VGVYYCLQGSHVPSSFGGGTKVEIK |
| 22 | 13F6 V$_H$.4 | EVQVVESGGGLVQPGGSLRLSCAASGFAFSSYDMSWVRQAP GKGLEWVSYISRGGGYTYYADSVKGRFTISRDNAKNTLYLQ MNSLKAEDTAVYYCSRHIYYGSSHYYAMDVWGQGTTVTVSS |
| 23 | 13F6 V$_L$.5 | QLVLTQSPSASASLGASIKLTCTLSRQHSTYTIEWYQQQPGKS PRYVMELKKDGSHSTGDGIPDRFSGSSSGADRYLTISNLQSED EAEYICGEGDTIKEQFVYVFGGGTKVTVLG |
| 24 | 13F6 V$_L$.6 | QLVLTQSPSASASLGASIKLTCTLSRQHSTYTIEWYQQQPEKG PRYVMELKKDGSHSTGDGIPDRFSGSSSGADRYLTISNLQSED EADYICGEGDTIKEQFVYVFGGGTKVTVLG |
| 25 | 1H3V$_H$.2 (A49G) | EVQLVESGGGLVQPGGSLRLSCTASGFNIKDTYIHWVRQAPG KGLEWVGRIDPANGNTKYADSVKGRFTISADTSKNTAYLQM NSLRAEDTAVYYCARESRISTMLTTGYFDYWGQGTLVTVSS |
| 26 | 1H3V$_H$.3 (A49G, S71T) | EVQLVESGGGLVQPGGSLRLSCTASGFNIKDTYIHWVRQAPG KGLEWVGRIDPANGNTKYADSVKGRFTITADTSKNTAYLQM NSLRAEDTAVYYCARESRISTMLTTGYFDYWGQGTLVTVSS |

TABLE 2-continued

Summary Sequence Table

| SEQ ID Number | Description | Sequence |
|---|---|---|
| 27 | 1H3V$_L$.2 (A42S) | DIQMTQSPSTLSASVGDRVTITCSASSSVSYMYWYQQKPGKSP KLLIYDTSNLASGVPARFSGSGSGTEFTLTISSLQPDDFATYYC QQWSSYPYTFGQGTKVEVK |
| 28 | 1H3$_{VL}$.3 (A42S, A59V, F70Y, Q99G) | DIQMTQSPSTLSASVGDRVTITCSASSSVSYMYWYQQKPGKSP KLLIYDTSNLASGVPVRFSGSGSGTEYTLTISSLQPDDFATYYC QQWSSYPYTFGGGTKVEVK |
| 29 | 1H3V$_L$.4 | DIQMTQSPASVGDRVTITCSASSSVSYMYWYQQKPGKSPKLLI YDTSNLASGVPARFSGSGSGTEFTLTISSLQPDDFATYYCQQW SSYPYTFGQGTKVEVK |
| 30 | 1H3V$_L$.5 (A59V, F70Y, Q99G) | DIQMTQSPASVGDRVTITCSASSSVSYMYWYQQKPGKSPKLLI YDTSNLASGVPVRFSGSGSGTEYTLTISSLQPDDFATYYCQQW SSYPYTFGGGTKVEVK |
| 31 | 1H3V$_L$.6 | MTQTPAIMSASPGEKVTMTCSASSSVSYMYVVYQQKPGSSPRL LIYDTSNLASGVPVRFSGSGSGTSYSLTISRMEAEDAATYYCQ QWSSYPYTFGGGTKLEIK |
| 32 | 2G4V$_H$.2 (G49A, F50E) | EVQLLESGGGLVQPGGSLRLSCVASGFTFSNYWMNWVRQAP GKGLEWLAEIRLKSNNYATHYSASVKGRFTISRDKSKSTLYL QMNTLQAEDSAIYYCTRGNGNYRAMDYWGQGTLVTVSS |
| 33 | 2G4V$_H$.3 | EVQLLESGGGLVQPGGSLRLSCVASGFTFSNYWMNWVRQAP GKGLEWLAEIRLKSNNYATHYSASVKGRFTISRDDSKRSVYL QMNTLQAEDSAIYYCTRGNGNYRAMDYWGQGTLVTVSS |
| 34 | 2G4V$_H$.4 | EVQLLESGGGLVQPGGSLRLSCVASGFTFSNYWMNWVRQAP GKGLEWLAEIRLKSVNYATHYSASVKGRFTISRDDSKRSVYL QMNTLQAEDSAIYYCTRGAGVFRAMFYWGQGTLVTVSS |
| 35 | 2G4V$_H$.5 (A102V) | EVQLLESGGGLVQPGGSLRLSCVASGFTFSNYWMNWVRQAP GKGLEWLAEIRLKSVNYATHYSASVKGRFTISRDDSKRSVYL QMNTLQAEDSAIYYCTRGVGVFRAMFYWGQGTLVTVSS |
| 36 | 2G4V$_L$.2 (A43S, K45Q, Q100G) | DIQMTQSPSSLSASVGDRVTITCRASENIYSSLAWYQQKPGKS PQLLVYSATILADGVPSRFSGSGSGTDFTLTISSLQPEDFATYY CQHFWGTPYTFGGGTKVEIK |
| 37 | 2G4V$_L$.3 (Q3V, A43S, K45Q, D70Q, F71Y, Q100G) | DIVMTQSPSSLSASVGDRVTITCRASENIYSSLAWYQQKPGKS PQLLVYSATILADGVPSRFSGSGSGTQYTLTISSLQPEDFATYY CQHFWGTPYTFGGGTKVEIK |
| 38 | 4G7V$_H$.2 (G44S) | QVQLVQSGAEVKKPGSSVKVSCKASGSSFTGFSMNWVRQAP GQSLEWMGNIDTYYGGTTYNGKFKGRVTITADKSTSTAYME LSSLRSEDTAVYYCARSAYYGSTFAYWGQGTLVTVSS |
| 39 | 4G7V$_H$.3 (G44S, M48I, I70L, A72V) | QVQLVQSGAEVKKPGSSVKVSCKASGSSFTGFSMNWVRQAP GQSLEWIGNIDTYYGGTTYNGKFKGRVTLTVDKSTSTAYMEL SSLRSEDTAVYYCARSAYYGSTFAYWGQGTLVTVSS |
| 40 | 4G7V$_H$.3.1 (G44S, M48I, N50V, I70L, A72V) | QVQLVQSGAEVKKPGSSVKVSCKASGSSFTGFSMNWVRQAP GQSLEWIGVIDTYYGGTTYNGKFKGRVTLTVDKSTSTAYMEL SSLRSEDTAVYYCARSAYYGSTFAYWGQGTLV |
| 41 | 4G7V$_H$.3.2 (F32V, G44S, M48I, I70L, A72V) | QVQLVQSGAEVKKPGSSVKVSCKASGSSFTGVSMNWVRQAP GQSLEWIGNIDTYYGGTTYNGKFKGRVTLTVDKSTSTAYMEL SSLRSEDTAVYYCARSAYYGSTFAYWGQGTLVTVSS |
| 42 | 4G7V$_L$.2 (A43S, Y87F) | DIQMTQSPSSLSASVGDRVTITCRASENIYSYLAWYQQKPGKS PKLLVYNAKTLIEGVPSRFSGSGSGTDFTFTISSLQPEDIATYFC QHHFGTPFTFGQGTKVEIK |
| 43 | 4G7V$_L$.3 (Q3V, A48S, D70Q, T72S, F73L, Y87F, Q100S) | DIVMTQSPSSLSASVGDRVTITCRASENIYSYLAWYQQKPGKS PKLLVYNAKTLIEGVPSRFSGSGSGTQFSLTISSLQPEDIATYFC QHHFGTPFTFGSGTKVEIK |

TABLE 2-continued

Summary Sequence Table

| SEQ ID Number | Description | Sequence |
|---|---|---|
| 44 | 4G7 $V_L$.4 (Q3V, A48S, K52V, D70Q, T72S, F73L, Y87F, Q100S) | DIVMTQSPSSLSASVGDRVTITCRASENIYSYLAWYQQKPGKS PKLLVYNAVTLIEGVPSRFSGSGSGTQFSLTISSLQPEDIATYFC QHHFGTPFTFGSGTKVEIK |
| 45 | 13C6 $V_H$ CDR1 | GFSLSTSGV |
| 46 | 13C6 $V_H$ CDR2 | WWDDD |
| 47 | 13C6 $V_H$ CDR3 | RDPFGYDNAMGY |
| 48 | 13C6 $V_L$ CDR1 | KASQNVGTAVA |
| 49 | 13C6 $V_L$ WT CDR2 | SASNRYT |
| 50 | 13C6 $V_L$.1 and $V_L$.2 CDR2 | SASNRYS |
| 51 | 13C6 $V_L$ CDR3 | QQYSSYPLT |
| 52 | 6D8 $V_H$ CDR1 | GFDFSRY |
| 53 | 6D8 $V_H$ CDR2 | NPDSST |
| 54 | 6D8 $V_H$ CDR3 | QGYGYNY |
| 55 | 6D8 $V_L$ CDR1 | RSSQSIVHSNGNTYLE |
| 56 | 6D8 $V_L$ CDR2 | KASNRFS |
| 57 | 6D8 $V_L$ WT CDR3 | LQGSHVPST |
| 58 | 6D8 $V_L$.3 CDR3 | LNGSHVPST |
| 59 | 6D8 $V_L$.4 CDR3 | LQGSHVPSS |
| 60 | 13F6 $V_H$ CDR1 | GFAFSSY |
| 61 | 13F6 $V_H$ CDR2 | SRGGGY |
| 62 | 13F6 $V_H$ WT CDR3 | HIYYGSSHYYAMDY |
| 63 | 13F6 $V_H$.4 CDR3 | HIYYGSSHYYAMDV |
| 64 | 13F6 $V_L$ CDR1 | TLSRQHSTYTIE |
| 65 | 13F6 $V_L$ CDR2 | LKKDGSHSTGD |
| 66 | 13F6 $V_L$ WT CDR3 | GVGDTIKEQFVYV |

TABLE 2-continued

Summary Sequence Table

| SEQ ID Number | Description | Sequence |
|---|---|---|
| 67 | 13F6 $V_L$.5 and $V_L$.6 CDR3 | GEGDTIKEQFVYV |
| 68 | 1H3 $V_H$ CDR1 | GFNIKDT |
| 69 | 1H3 $V_H$ CDR2 | DPANGN |
| 70 | 1H3 $V_H$ CDR3 | ESRISTMLTTGYFDY |
| 71 | 1H3 $V_L$ CDR1 | SASSSVSYMY |
| 72 | 1H3 $V_L$ CDR2 | DTSNLAS |
| 73 | 1H3 $V_L$ CDR3 | QQWSSYPYT |
| 74 | 2G4 $V_H$ CDR1 | GFTFSNY |
| 75 | 2G4 $V_H$ CDR2 | RLKSNNYA |
| 76 | 2G4 $V_H$ CDR3 | GNGNYRAMDY |
| 77 | 2G4$V_H$.4 and 2G4$V_H$.5 CDR2 | RLKSVNYA |
| 78 | 2G4$V_H$.4 CDR3 | GAGVFRAMFY |
| 79 | 2G4$V_H$.5 CDR3 | GVGVFRAMFY |
| 80 | 2G4 $V_L$ CDR1 | RASENIYSSLA |
| 81 | 2G4 $V_L$ CDR2 | SATILAD |
| 82 | 2G4 $V_L$ CDR3 | QHFWGTPYT |
| 83 | 4G7 $V_H$ CDR1 | GSSFTGF |
| 84 | 4G7 $V_H$ CDR2 | DTYYGG |
| 85 | 4G7 $V_H$ CDR3 | SAYYGSTFAY |
| 86 | 4G7$V_H$.3.2 CDR1 | GSSFTGV |
| 87 | 4G7 $V_L$ CDR1 | RASENIYSYLA |
| 88 | 4G7 $V_L$ CDR2 | NAKTLIE |
| 89 | 4G7 $V_L$ CDR3 | QHHFGTPFT |
| 90 | 4G7 $V_L$.4 CDR2 | NAVTLIEG |

TABLE 2-continued

Summary Sequence Table

| SEQ ID Number | Description | Sequence |
|---|---|---|
| 91 | Ebola virus glycoprotein precursor, Genebank Accession: AIG96634,1 | MGVTGILQLPRDRFKRTSFFLWVIILFQRTFSIPLGVIHNSTLQV SDVDKLVCRDKLSSTNQLRSVGLNLEGNGVATDVPSVTKRW GFRSGVPPKVVNYEAGEWAENCYNLEIKKPDGSECLPAAPDG IRGFPRCRYVHKVSGTGPCAGDFAFHKEGAFFLYDRLASTVIY RGTTFAEGVVAFLILPQAKKDFFSSHPLREPVNATEDPSSGYY STTIRYQATGFGTNETEYLFEVDNLTYVQLESRFTPQFLLQLN ETIYASGKRSNTTGKLIVVKVNPEIDTTIGEWAFWETKKNLTRK IRSEELSFTAVSNGPKNISGQSPARTSSDPETNTTNEDHKIMAS ENSSAMVQVHSQGRKAAVSHLTTLATISTSPQPPTTKTGPDNS THNTPVYKLDISEATQVGQHHRRADNDSTASDTPPATTAAGP LKAENTNTSKSADSLDLATTTSPQNYSETAGNNNTHHQDTGE ESASSGKLGLITNTIAGVAGLITGGRRTRREVIVNAQPKCNPNL HYWTTQDEGAAIGLAWIPYFGPAAEGIYTEGLMHNQDGLICG LRQLANETTQALQLFLRATTELRTFSILNRKAIDFLLQRWGGT CHILGPDCCIEPHDWTKNITDKIDQIIHDFVDKTLPDQGDNDN WWTGWRQWIPAGIGVTGVIIAVIALFCICKFVF |
| 92 | 1H3-V$_H$ (mouse) | EVQLQQSGAELVKPGASVKLSCTASGFNIKDTYIHWVKQGPE QGLEWIGRIDPANGNTKYDPKFQGKATITADTSSNTAYLQLS GLTSEDTAVYYCARESRISTMLTTGYFDYWGQGTTLTVSS |
| 93 | 1H3-V$_L$ (mouse) | DIVMTQSPASPGEKVTMTCSASSSVSYMWYQQKPGSSPRLL IYDTSNLASGVPVRFSGSGSGTSYSLTISRMEAEDAATYYCQQ WSSYPYTFGGGTKLEIK |
| 94 | 2G4-V$_H$ (mouse) | EVQLQQSGGGLMQPGGSMKLSCVASGFTFSNYWMNWVRQS PEKGLEWVAEIRLKSNNYATHYAESVKGRFTISRDDSKRSVY LQMNTLRAEDTGIYYCTRGNGNYRAMDYWGQGTSVTVSS |
| 95 | 2G4-V$_L$ (mouse) | DIVMTQSPASLSVSVGETVSITCRASENIYSSLAWYQQKQGKS PQLLVYSATILADGVPSRFSGSGSGTQYSLKINSLQSEDFGTYY CQHFWGTPYTFGGGTKLEIK |
| 96 | 4G7-V$_H$ (mouse) | EVQLQQSGPELEMPGASVKISCKASGSSFTGFSMNWVKQSNG KSLEWIGNIDTYYGGTTYNQKFKGKATLTVDKSSSTAYMQLK SLTSEDSAVYYCARSAYYGSTFAYWGQGTLVTVSS |
| 97 | 4G7-V$_L$ (mouse) | DIVMTQSPASLSASVGETVTITCRASENIYSYLAWYQQKQGKS PQLLVYNAKTLIEGVPSRFSGSGSGTQFSLKINSLQPEDFGSYF CQHHFGTPFTFGSGTELEIK |
| 98 | Ebola virus GP T270-P279 | TGKLIVVKVNP |
| 99 | Ebola virus GP Y394-R409 | YKLDISEATQVGQHHR |
| 100 | Ebola virus GPV505-C511 | VNAQPKC |
| 101 | Ebola virus GP N550-E564 | NQDGLICGLRQLANE |

The invention claimed is:

1. An isolated monoclonal antibody, or antigen binding portion thereof, which binds to Ebola virus glycoprotein, wherein the monoclonal antibody is selected from the group consisting of:
   (a) a monoclonal antibody comprising a variable heavy chain and a variable light chain set forth in SEQ ID NOs: 39 and 14;
   (b) a monoclonal antibody comprising a variable heavy chain and a variable light chain set forth in SEQ ID NOs: 32 and 37; and
   (c) a monoclonal antibody comprising a variable heavy chain and a variable light chain set forth in SEQ ID NOs: 15 and 17.

2. The monoclonal antibody of claim 1, comprising a variable heavy chain and a variable light chain set forth in SEQ ID NOs: 39 and 14.

3. The monoclonal antibody of claim 1, comprising a variable heavy chain and a variable light chain set forth in SEQ ID NOs: 32 and 37.

4. The monoclonal antibody of claim 1, comprising a variable heavy chain and a variable light chain set forth in SEQ ID NOs: 15 and 17.

5. An isolated monoclonal antibody, or antigen binding portion thereof, which binds to Ebola virus glycoprotein, comprising:
   (a) a heavy chain comprising CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and
   (b) a light chain comprising CDR1, CDR2, and CDR3 sequences set forth in SEQ ID NOs: 87, 88, and 89 respectively, wherein the remainder of the light chain is from a human immunoglobulin; or
   (a) a heavy chain comprising CDR1, CDR2, and CDR3 sequences set forth in SEQ ID NOs: 74, 75, and 76, respectively, and variable region framework residues selected from the group consisting of 49H, 50H, or a combination thereof (Kabat numbering convention) from the heavy chain variable region set forth in SEQ ID NO: 94, wherein the remainder of the heavy chain is from a human immunoglobulin; and
   (b) a light chain comprising CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin; or
   (a) a heavy chain comprising CDR1, CDR2, and CDR3 sequences set forth in SEQ ID NOs: 45, 46, and 47, respectively, wherein the remainder of the heavy chain is from a human immunoglobulin; and
(b) a light chain comprising CDR1, CDR2, and CDR3 sequences set forth in SEQ ID NOs: 48, 50, and 51, respectively, wherein the remainder of the light chain is from a human immunoglobulin.

6. An isolated monoclonal antibody, or antigen binding portion thereof, which binds to Ebola virus glycoprotein, and comprises a heavy chain variable region and light chain variable region comprising an amino acid sequence at least 90% identical to the amino acid sequences selected from the group consisting of:
(a) SEQ ID NOs: 15 and 17, respectively;
(b) SEQ ID NOs: 32 and 37, respectively; and
(c) SEQ IS NOs: 39 and 14, respectively;
wherein the monoclonal antibody is a neutralizing antibody and specifically binds to Ebola virus glycoprotein with an EC50 of 200 pM or less, as measured by ELISA.

7. The isolated monoclonal antibody of claim 1 wherein the monoclonal antibody exhibits at least one of the following properties:
(a) binds to Ebola virus glycoprotein with an EC50 of 200 pM or less, as measured by ELISA;
(b) binds to a conformational epitope on Ebola virus glycoprotein (SEQ ID NO: 91);
(c) binds within the region V505-C511 of Ebola virus glycoprotein (SEQ ID NO: 91);
(d) binds within the region N550-E564 of Ebola virus glycoprotein (SEQ ID NO: 91);
(e) binds within the region T270-P279 of Ebola virus glycoprotein (SEQ ID NO: 91);
(f) binds within the region Y394-R404 of Ebola virus glycoprotein (SEQ ID NO: 91); and
(g) engages immune components such as antibody-dependent cellular cytotoxicity (ADCC) or complement-dependent cytotoxicity (CDC).

8. The monoclonal antibody of claim 1 which binds to a conformational epitope on Ebola virus glycoprotein (SEQ ID NO: 91) that spans V505-C511 and N550-E564.

9. The monoclonal antibody of claim 1 which binds to a conformational epitope on Ebola virus glycoprotein (SEQ ID NO: 91) that spans T270-P279 and Y394-R409.

10. The monoclonal antibody of claim 1, having neutralizing activity against the Zaire Ebola Virus.

11. The monoclonal antibody of claim 1, which specifically binds to Ebola virus glycoprotein with an $EC_{50}$ of 200 pM or less, as measured by ELISA.

12. The monoclonal antibody of claim 1, wherein the antibody is selected from the group consisting of an IgG1, an IgG2, an IgG3, an IgG4, an IgM, an IgA1, an IgA2, an IgD, and an IgE antibody.

13. The monoclonal antibody of claim 12, wherein the antibody is an IgG1 antibody.

14. A pharmaceutical composition comprising a monoclonal antibody or antigen binding portion thereof of claim 1 and a pharmaceutically acceptable carrier.

15. A pharmaceutical composition comprising one or more of the monoclonal antibodies or antigen binding portions thereof of claim 1 and a pharmaceutically acceptable carrier.

16. An isolated monoclonal antibody, or antigen binding portion thereof, which binds to Ebola virus glycoprotein, comprising:
(a) a heavy chain and a light chain, wherein:
(i) the heavy chain comprises CDR1, CDR2, and CDR3 sequences set forth in SEQ ID NOs: 83, 84, and 85, respectively, and variable region framework residues selected from the group consisting of 44H, 48H, 70H, 72H, or a combination thereof (Kabat numbering convention) from the heavy chain variable region set forth in SEQ ID NO: 96, wherein the remainder of the heavy chain is from a human immunoglobulin; and
(ii) the light chain comprises CDR1, CDR2, and CDR3 sequences set forth in SEQ ID NOs: 87, 88, and 89 respectively, wherein the remainder of the light chain is from a human immunoglobulin; or
(b) a heavy chain and light chain, wherein:
(i) the heavy chain comprises CDR1, CDR2, and CDR3 sequences set forth in SEQ ID NOs: 74, 75, and 76, respectively, and variable region framework residues selected from the group consisting of 49H, 50H, or a combination thereof (Kabat numbering convention) from the heavy chain variable region set forth in SEQ ID NO: 94, wherein the remainder of the heavy chain is from a human immunoglobulin; and
(ii) the light chain comprises CDR1, CDR2, and CDR3 sequences set forth in SEQ ID NOs: 80, 81, and 82, respectively, and variable region framework residues selected from the group consisting of 3 L, 43 L, 45 L, 70 L, 71 L, 100 L, or a combination thereof (Kabat numbering convention) from the light chain variable region set forth in SEQ ID NO: 95, wherein the remainder of the light chain is from a human immunoglobulin;
and wherein the monoclonal antibody binds to a conformational epitope on Ebola virus glycoprotein (SEQ ID NO: 91) comprising an amino acid sequence that spans V505-C511 and N550-E564.

17. The isolated monoclonal antibody of claim 16, wherein the heavy and light chains set forth in (a) comprise a variable heavy chain and a variable light chain selected from the group consisting of:
(i) SEQ ID NOs: 11 and 12, respectively;
(ii) SEQ ID NOs: 11 and 36, respectively;
(iii) SEQ IS NOs: 11 and 37, respectively;
(iv) SEQ ID NOs: 32 and 12, respectively;
(v) SEQ ID NOs: 32 and 36, respectively;
(vi) SEQ ID NOs: 32 and 37, respectively;
(vii) SEQ ID NOs: 33 and 12, respectively;
(viii) SEQ ID NOs: 33 and 36, respectively; and
(ix) SEQ ID NOs: 33 and 37, respectively.

18. The isolated monoclonal antibody of claim 16, wherein the heavy and light chains set forth in (b) comprise a variable heavy chain and a variable light chain selected from the group consisting of:
(i) SEQ ID NOs: 13 and 14, respectively;
(ii) SEQ ID NOs: 13 and 42, respectively;
(iii) SEQ ID NOs: 13 and 43, respectively;
(iv) SEQ ID NOs: 38 and 14, respectively;
(v) SEQ ID NOs: 38 and 42, respectively;
(vi) SEQ ID NOs: 38 and 43, respectively;
(vii) SEQ ID NOs: 39 and 42, respectively;
(viii) SEQ ID NOs: 39 and 43, respectively;
(ix) SEQ ID NOs: 40 and 14, respectively;
(x) SEQ ID NOs: 40 and 42, respectively; and
(xi) SEQ ID NOs: 40 and 43, respectively.

19. A pharmaceutical composition comprising both isolated monoclonal antibodies of claim 16 (a) and (b), and an isolated monoclonal antibody or antigen binding portion thereof, which binds to Ebola virus glycoprotein, comprising:
(a) a heavy chain comprising CDR1, CDR2, and CDR3 sequences set forth in SEQ ID NOs: 45, 46, and 47, respectively, wherein the remainder of the heavy chain is from a human immunoglobulin; and (b) a light chain comprising CDR1, CDR2, and CDR3 sequences set forth in SEQ ID NOs: 48, 50, and 51, respectively, wherein the remainder of the light chain is from a human immunoglobulin.

20. A pharmaceutical composition comprising a monoclonal antibody or antigen binding portion thereof of claim 2 and a pharmaceutically acceptable carrier.

21. A pharmaceutical composition comprising a monoclonal antibody or antigen binding portion thereof of claim 3 and a pharmaceutically acceptable carrier.

22. A pharmaceutical composition comprising a monoclonal antibody or antigen binding portion thereof of claim 4 and a pharmaceutically acceptable carrier.

23. A pharmaceutical composition comprising a monoclonal antibody or antigen binding portion thereof of claim 5 and a pharmaceutically acceptable carrier.

24. A pharmaceutical composition comprising a monoclonal antibody or antigen binding portion thereof of claim 6 and a pharmaceutically acceptable carrier.

25. A pharmaceutical composition comprising a monoclonal antibody or antigen binding portion thereof of claim 16 and a pharmaceutically acceptable carrier.

26. A pharmaceutical composition comprising a monoclonal antibody or antigen binding portion thereof of claim 17 and a pharmaceutically acceptable carrier.

27. A pharmaceutical composition comprising a monoclonal antibody or antigen binding portion thereof of claim 18 and a pharmaceutically acceptable carrier.

28. A pharmaceutical composition comprising one or more of the monoclonal antibodies or antigen binding portions thereof of claim 5 and a pharmaceutically acceptable carrier.

29. A pharmaceutical composition comprising one or more of the monoclonal antibodies or antigen binding portions thereof of claim 6 and a pharmaceutically acceptable carrier.

30. A pharmaceutical composition comprising one or more of the monoclonal antibodies or antigen binding portions thereof of claim 16 and a pharmaceutically acceptable carrier.

* * * * *

SEQUENCE LISTING

<160> NUMBER OF SEQ ID NOS: 101

<210> SEQ ID NO 1
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 Heavy Chain -continued

```
<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human IgG1 Light chain (kappa)

<400> SEQUENCE: 2

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 3
<211> LENGTH: 122
<212> TYPE: PRT
<213> ORGANISM: Homo sapiens
<220> FEATURE:
<221> NAME/KEY: misc_feature
<222> LOCATION: (1)..(122)
<223> OTHER INFORMATION: 13C6 VH Wild Type

<400> SEQUENCE: 3

Gln Leu Thr Leu Lys Glu Ser Gly Pro Gly Ile Leu Lys Pro Ser Gln
 1               5                  10                  15

Thr Leu Ser Leu Thr Cys Ser Leu Ser Gly Phe Ser Leu Ser Thr Ser
             20                  25                  30

Gly Val Gly Val Gly Trp Phe Arg Gln Pro Ser Gly Lys Gly Leu Glu
             35                  40                  45

Trp Leu Ala Leu Ile Trp Trp Asp Asp Lys Tyr Tyr Asn Pro Ser
 50                  55                  60

Leu Lys Ser Gln Leu Ser Ile Ser Lys Asp Phe Ser Arg Asn Gln Val
 65                  70                  75                  80

Phe Leu Lys Ile Ser Asn Val Asp Ile Ala Asp Thr Ala Thr Tyr Tyr
                 85                  90                  95

Cys Ala Arg Arg Asp Pro Phe Gly Tyr Asp Asn Ala Met Gly Tyr Trp
                100                 105                 110

Gly Gln Gly Thr Ser Val Thr Val Ser Ser
        115                 120

<210> SEQ ID NO 4
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: 13C6 VL Wild Type

<400> SEQUENCE: 4

Asp Ile Val Met Thr Gln Ser Gln Lys Phe Met Ser Thr Ser Val Gly
 1               5                  10                  15

Asp Arg Val Ser Leu Thr Cys Lys Ala Ser Gln Asn Val Gly Thr Ala
             20                  25                  30

Val Ala Trp Tyr Gln Gln Lys Pro Gly Gln Ser Pro Lys Leu Leu Ile
             35                  40                  45

Tyr Ser Ala Ser Asn Arg Tyr Thr Gly Val Pro Asp Arg Phe Thr Gly
 50                  55                  60
```

Ser Gly Ser Gly Thr Asp Phe Thr Leu Thr Ile Ser Asn Met Gln Ser
 65                  70                  75                  80

Glu Asp Leu Ala Asp Tyr Phe Cys Gln Gln Tyr Ser Ser Tyr Pro Leu
                 85                  90                  95

Thr Phe Gly Ala Gly Thr Lys Leu Glu Leu Arg
            100                 105

<210> SEQ ID NO 5
<211> LENGTH: 116
<212> TYPE: PRT
<213> ORGANISM: Homo sapiens
<220> FEATURE:
<221> NAME/KEY: misc_feature
<222> LOCATION: (1)..(116)
<223> OTHER INFORMATION: 6D8 VH  Wild Type

<400> SEQUENCE: 5

Asp Val Lys Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Thr Pro Ser Leu
     50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                 90                   95

Thr Arg Gln Gly Tyr Gly Tyr Asn Tyr Trp Gly Gln Gly Thr Thr Leu
            100                 105                 110

Ile Val Ser Ser
            115

<210> SEQ ID NO 6
<211> LENGTH: 112
<212> TYPE: PRT
<213> ORGANISM: Homo sapiens
<220> FEATURE:
<221> NAME/KEY: misc_feature
<222> LOCATION: (1)..(112)
<223> OTHER INFORMATION: 6D8 VL Wild Type

<400> SEQUENCE: 6

Asp Val Leu Leu Thr Gln Ile Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Ala Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Asn Arg Val Glu Ala Glu Asp Leu Gly Val Tyr Tyr Cys Leu Gln Gly
                 85                  90                  95

Ser His Val Pro Ser Thr Phe Gly Gly Gly Thr Lys Leu Glu Ile Lys
            100                 105                 110

```
<210> SEQ ID NO 7
<211> LENGTH: 123
<212> TYPE: PRT
<213> ORGANISM: Homo sapiens
<220> FEATURE:
<221> NAME/KEY: misc_feature
<222> LOCATION: (1)..(123)
<223> OTHER INFORMATION: 13F6 VH Wild Type

<400> SEQUENCE: 7
```

Glu Val Gln Val Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Arg Gly Gly Tyr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg His Ile Tyr Tyr Gly Ser Ser His Tyr Tyr Ala Met Asp Tyr
            100                 105                 110

Trp Gly Gln Gly Thr Ser Val Thr Val Ser Ser
        115                 120

```
<210> SEQ ID NO 8
<211> LENGTH: 116
<212> TYPE: PRT
<213> ORGANISM: Homo sapiens
<220> FEATURE:
<221> NAME/KEY: misc_feature
<222> LOCATION: (1)..(116)
<223> OTHER INFORMATION: 13F6 VL Wild Type

<400> SEQUENCE: 8
```

Gln Leu Val Leu Thr Gln Ser Ser Ser Ala Ser Phe Ser Leu Gly Ala
1               5                   10                  15

Ser Ala Lys Leu Thr Cys Thr Leu Ser Arg Gln His Ser Thr Tyr Thr
            20                  25                  30

Ile Glu Trp Tyr Gln Gln Pro Leu Lys Pro Pro Arg Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Thr Ile Lys Glu Gln Phe Val Tyr Val Phe Gly Gly Gly Thr Lys Val
            100                 105                 110

Thr Val Leu Gly
        115

```
<210> SEQ ID NO 9
<211> LENGTH: 124
<212> TYPE: PRT
<213> ORGANISM: Artificial Sequence
<220> FEATURE:
<223> OTHER INFORMATION: Synthetic: 1H3VH .1
```

```
<400> SEQUENCE: 9

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Gly Asn Thr Lys Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Ile Ser Thr Met Leu Thr Thr Gly Tyr Phe Asp
            100                 105                 110

Tyr Trp Gly Gln Gly Thr Leu Val Thr Val Ser Ser
        115                 120

<210> SEQ ID NO 10
<211> LENGTH: 106
<212> TYPE: PRT
<213> ORGANISM: Artificial Sequence
<220> FEATURE:
<223> OTHER INFORMATION: Synthetic:  1H3VL.1

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Tyr Pro Tyr Thr
                85                  90                  95

Phe Gly Gln Gly Thr Lys Val Glu Val Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Synthetic:  2G4VH .1

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Leu
        35                  40                  45

Gly Phe Ile Arg Leu Lys Ser Asn Asn Tyr Ala Thr His Tyr Ser Ala
    50                  55                  60
```

```
Ser Val Lys Gly Arg Phe Thr Ile Ser Arg Asp Lys Ser Lys Ser Thr
 65                  70                  75                  80

Leu Tyr Leu Gln Met Asn Thr Leu Gln Ala Glu Asp Ser Ala Ile Tyr
                 85                  90                  95

Tyr Cys Thr Arg Gly Asn Gly Asn Tyr Arg Ala Met Asp Tyr Trp Gly
            100                 105                 110

Gln Gly Thr Leu Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic:  2G4VL.1

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Ser
            20                  25                  30

Leu Ala Trp Tyr Gln Gln Lys Pro Gly Lys Ala Pro Lys Leu Leu Val
        35                  40                  45

Tyr Ser Ala Thr Ile Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gln Gly Thr Lys Val Glu Ile Lys
            100                 105

<210> SEQ ID NO 13
<211> LENGTH: 119
<212> TYPE: PRT
<213> ORGANISM: Artificial Sequence
<220> FEATURE:
<223> OTHER INFORMATION: Synthetic:  4G7VH .1

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Ser Ser Phe Thr Gly Phe
            20                  25                  30

Ser Met Asn Trp Val Arg Gln Ala Pro Gly Gln Gly Leu Glu Trp Met
        35                  40                  45

Gly Asn Ile Asp Thr Tyr Tyr Gly Gly Thr Thr Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Gly Ser Thr Phe Ala Tyr Trp Gly Gln Gly
            100                 105                 110

Thr Leu Val Thr Val Ser Ser
        115

<210> SEQ ID NO 14
```

```
<211> LENGTH: 107
<212> TYPE: PRT
<213> ORGANISM: Artificial Sequence
<220> FEATURE:
<223> OTHER INFORMATION: Synthetic: 4G7VL.1

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ile Glu Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His His Phe Gly Thr Pro Phe
                85                  90                  95

Thr Phe Gly Gln Gly Thr Lys Val Glu Ile Lys
            100                 105

<210> SEQ ID NO 15
<211> LENGTH: 122
<212> TYPE: PRT
<213> ORGANISM: Artificial Sequence
<220> FEATURE:
<223> OTHER INFORMATION: Synthetic: 13C6 VH.1 (T56S)

<400> SEQUENCE: 15

Gln Leu Thr Leu Lys Glu Ser Gly Pro Thr Leu Val Lys Pro Thr Gln
1               5                   10                  15

Thr Leu Ser Leu Thr Cys Thr Phe Ser Gly Phe Ser Leu Ser Thr Ser
            20                  25                  30

Gly Val Gly Val Gly Trp Phe Arg Gln Pro Pro Gly Lys Ala Leu Glu
        35                  40                  45

Trp Leu Ala Leu Ile Trp Trp Asp Asp Asp Lys Tyr Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asp Pro Phe Gly Tyr Asp Asn Ala Met Gly Tyr Trp
            100                 105                 110

Gly Gln Gly Thr Thr Val Thr Val Ser Ser
        115                 120

<210> SEQ ID NO 16
<211> LENGTH: 122
<212> TYPE: PRT
<213> ORGANISM: Artificial Sequence
<220> FEATURE:
<223> OTHER INFORMATION: Synthetic: 13C6 VH.2 (T56S)

<400> SEQUENCE: 16

Gln Leu Thr Leu Lys Glu Ser Gly Pro Thr Leu Val Lys Pro Thr Gln
1               5                   10                  15

Thr Leu Ser Leu Thr Cys Thr Phe Ser Gly Phe Ser Leu Ser Thr Ser
            20                  25                  30
```

Gly Val Gly Val Gly Trp Phe Arg Gln Pro Pro Gly Lys Ala Leu Glu
             35                  40                  45

Trp Leu Ala Leu Ile Trp Trp Asp Asp Lys Tyr Tyr Gly Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Asp Pro Phe Gly Tyr Asp Asn Ala Met Gly Tyr Trp
                100                 105                 110

Gly Gln Gly Thr Thr Val Thr Val Ser Ser
            115                 120

<210> SEQ ID NO 17
<211> LENGTH: 107
<212> TYPE: PRT
<213> ORGANISM: Artificial Sequence
<220> FEATURE:
<223> OTHER INFORMATION: Synthetic: 13C6 VL.1

<400> SEQUENCE: 17

Asp Ile Val Met Thr Gln Ser Pro Ser Phe Leu Ser Ala Ser Val Gly
 1               5                  10                  15

Asp Arg Val Thr Ile Thr Cys Lys Ala Ser Gln Asn Val Gly Thr Ala
                 20                  25                  30

Val Ala Trp Tyr Gln Gln Lys Pro Gly Lys Ala Pro Lys Leu Leu Ile
             35                  40                  45

Tyr Ser Ala Ser Asn Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Ser Ser Tyr Pro Leu
                 85                  90                  95

Thr Phe Gly Gly Gly Thr Lys Leu Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Synthetic: 13C6 VL.2

<400> SEQUENCE: 18

Asp Ile Val Met Thr Gln Ser Pro Ser Phe Leu Ser Ala Ser Val Gly
 1               5                  10                  15

Asp Arg Val Thr Ile Thr Cys Lys Ala Ser Gln Asn Val Gly Thr Ala
                 20                  25                  30

Val Ala Trp Tyr Gln Gln Lys Pro Gly Lys Ala Pro Lys Leu Leu Ile
             35                  40                  45

Tyr Ser Ala Ser Asn Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Ser Ser Tyr Pro Leu
                 85                  90                  95

Thr Phe Gly Gln Gly Thr Lys Leu Glu Ile Lys
            100                 105

```
<210> SEQ ID NO 19
<211> LENGTH: 116
<212> TYPE: PRT
<213> ORGANISM: Artificial Sequence
<220> FEATURE:
<223> OTHER INFORMATION: Synthetic:  6D8 VH.3

<400> SEQUENCE: 19

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Val Trp Val
        35                  40                  45

Ser Glu Ile Asn Pro Asp Ser Ser Thr Ile Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Gly Tyr Gly Tyr Asn Tyr Trp Gly Gln Gly Thr Thr Val
            100                 105                 110

Thr Val Ser Ser
        115

<210> SEQ ID NO 20
<211> LENGTH: 112
<212> TYPE: PRT
<213> ORGANISM: Artificial Sequence
<220> FEATURE:
<223> OTHER INFORMATION: Synthetic:  6D8 VL.3

<400> SEQUENCE: 20

Asp Val Leu Leu Thr Gln Ser Pro Leu Ser Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Asn Gly
                85                  90                  95

Ser His Val Pro Ser Thr Phe Gly Gly Gly Thr Lys Val Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Synthetic:  6D8 VL.4

<400> SEQUENCE: 21

Asp Val Leu Leu Thr Gln Thr Pro Leu Ser Leu Pro Val Thr Leu Gly
1               5                   10                  15
```

```
Gln Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Ala Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Ser His Val Pro Ser Ser Phe Gly Gly Gly Thr Lys Val Glu Ile Lys
            100                 105                 110
```

<210> SEQ ID NO 22
<211> LENGTH: 123
<212> TYPE: PRT
<213> ORGANISM: Artificial Sequence
<220> FEATURE:
<223> OTHER INFORMATION: Synthetic: 13F6 VH.4

<400> SEQUENCE: 22

```
Glu Val Gln Val Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
                20                  25                  30

Asp Met Ser Trp Val Arg Gln Ala Pro Gly Lys Gly Leu Glu Trp Val
            35                  40                  45

Ser Tyr Ile Ser Arg Gly Gly Gly Tyr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ser Arg His Ile Tyr Tyr Gly Ser Ser His Tyr Tyr Ala Met Asp Val
            100                 105                 110

Trp Gly Gln Gly Thr Thr Val Thr Val Ser Ser
        115                 120
```

<210> SEQ ID NO 23
<211> LENGTH: 116
<212> TYPE: PRT
<213> ORGANISM: Artificial Sequence
<220> FEATURE:
<223> OTHER INFORMATION: Synthetic: 13F6 VL.5

<400> SEQUENCE: 23

```
Gln Leu Val Leu Thr Gln Ser Pro Ser Ala Ser Ala Ser Leu Gly Ala
1               5                   10                  15

Ser Ile Lys Leu Thr Cys Thr Leu Ser Arg Gln His Ser Thr Tyr Thr
                20                  25                  30

Ile Glu Trp Tyr Gln Gln Pro Gly Lys Ser Pro Arg Tyr Val Met
            35                  40                  45

Glu Leu Lys Lys Asp Gly Ser His Ser Thr Gly Asp Gly Ile Pro Asp
        50                  55                  60

Arg Phe Ser Gly Ser Ser Ser Gly Ala Asp Tyr Leu Thr Ile Ser
65                  70                  75                  80

Asn Leu Gln Ser Glu Asp Glu Ala Glu Tyr Ile Cys Gly Glu Gly Asp
                85                  90                  95
```

-continued

```
Thr Ile Lys Glu Gln Phe Val Tyr Val Phe Gly Gly Gly Thr Lys Val
                100                 105                 110
Thr Val Leu Gly
        115

<210> SEQ ID NO 24
<211> LENGTH: 116
<212> TYPE: PRT
<213> ORGANISM: Artificial Sequence
<220> FEATURE:
<223> OTHER INFORMATION: Synthetic: 13F6 VL.6

<400> SEQUENCE: 24

Gln Leu Val Leu Thr Gln Ser Pro Ser Ala Ser Ala Ser Leu Gly Ala
1               5                   10                  15

Ser Ile Lys Leu Thr Cys Thr Leu Ser Arg Gln His Ser Thr Tyr Thr
                20                  25                  30

Ile Glu Trp Tyr Gln Gln Pro Glu Lys Gly Pro Arg Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Gly Ala Asp Arg Tyr Leu Thr Ile Ser
65                  70                  75                  80

Asn Leu Gln Ser Glu Asp Glu Ala Asp Tyr Ile Cys Gly Glu Gly Asp
                85                  90                  95

Thr Ile Lys Glu Gln Phe Val Tyr Val Phe Gly Gly Gly Thr Lys Val
                100                 105                 110

Thr Val Leu Gly
        115

<210> SEQ ID NO 25
<211> LENGTH: 124
<212> TYPE: PRT
<213> ORGANISM: Artificial Sequence
<220> FEATURE:
<223> OTHER INFORMATION: Synthetic: 1H3VH .2 (A49G)

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Asn Ile Lys Asp Thr
                20                  25                  30

Tyr Ile His Trp Val Arg Gln Ala Pro Gly Lys Gly Leu Glu Trp Val
        35                  40                  45

Gly Arg Ile Asp Pro Ala Asn Gly Asn Thr Lys Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Ile Ser Thr Met Leu Thr Thr Gly Tyr Phe Asp
                100                 105                 110

Tyr Trp Gly Gln Gly Thr Leu Val Thr Val Ser Ser
        115                 120

<210> SEQ ID NO 26
<211> LENGTH: 124
<212> TYPE: PRT
```

<213> ORGANISM: Artificial Sequence
<220> FEATURE:
<223> OTHER INFORMATION: Synthetic: 1H3VH.3 (A49G, S71T)

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Gly Arg Ile Asp Pro Ala Asn Gly Asn Thr Lys Tyr Ala Asp Ser Val
50                  55                  60

Lys Gly Arg Phe Thr Ile Thr Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Glu Ser Arg Ile Ser Thr Met Leu Thr Thr Gly Tyr Phe Asp
        100                 105                 110

Tyr Trp Gly Gln Gly Thr Leu Val Thr Val Ser Ser
        115                 120

<210> SEQ ID NO 27
<211> LENGTH: 106
<212> TYPE: PRT
<213> ORGANISM: Artificial Sequence
<220> FEATURE:
<223> OTHER INFORMATION: Synthetic:  1H3VL.2 (A42S)

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ser Pro Lys Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Tyr Pro Tyr Thr
            85                  90                  95

Phe Gly Gln Gly Thr Lys Val Glu Val Lys
        100                 105

<210> SEQ ID NO 28
<211> LENGTH: 106
<212> TYPE: PRT
<213> ORGANISM: Artificial Sequence
<220> FEATURE:
<223> OTHER INFORMATION: Synthetic:  1H3VL.3 (A42S, A59V, F70Y, Q99G)

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ser Pro Lys Leu Leu Ile Tyr
        35                  40                  45

```
Asp Thr Ser Asn Leu Ala Ser Gly Val Pro Val Arg Phe Ser Gly Ser
            50                  55                  60

Gly Ser Gly Thr Glu Tyr Thr Leu Thr Ile Ser Ser Leu Gln Pro Asp
 65                  70                  75                  80

Asp Phe Ala Thr Tyr Tyr Cys Gln Gln Trp Ser Ser Tyr Pro Tyr Thr
                 85                  90                  95

Phe Gly Gly Gly Thr Lys Val Glu Val Lys
            100                 105

<210> SEQ ID NO 29
<211> LENGTH: 102
<212> TYPE: PRT
<213> ORGANISM: Artificial Sequence
<220> FEATURE:
<223> OTHER INFORMATION: Synthetic: 1H3VL.4

<400> SEQUENCE: 29

Asp Ile Gln Met Thr Gln Ser Pro Ala Ser Val Gly Asp Arg Val Thr
 1               5                  10                  15

Ile Thr Cys Ser Ala Ser Ser Val Ser Tyr Met Tyr Trp Tyr Gln
             20                  25                  30

Gln Lys Pro Gly Lys Ser Pro Lys Leu Leu Ile Tyr Asp Thr Ser Asn
             35                  40                  45

Leu Ala Ser Gly Val Pro Ala Arg Phe Ser Gly Ser Gly Ser Gly Thr
 50                  55                  60

Glu Phe Thr Leu Thr Ile Ser Ser Leu Gln Pro Asp Asp Phe Ala Thr
 65                  70                  75                  80

Tyr Tyr Cys Gln Gln Trp Ser Ser Tyr Pro Tyr Thr Phe Gly Gln Gly
                 85                  90                  95

Thr Lys Val Glu Val Lys
            100

<210> SEQ ID NO 30
<211> LENGTH: 102
<212> TYPE: PRT
<213> ORGANISM: Artificial Sequence
<220> FEATURE:
<223> OTHER INFORMATION: Synthetic: 1H3VL.5 (A59V, F70Y, Q99G)

<400> SEQUENCE: 30

Asp Ile Gln Met Thr Gln Ser Pro Ala Ser Val Gly Asp Arg Val Thr
 1               5                  10                  15

Ile Thr Cys Ser Ala Ser Ser Val Ser Tyr Met Tyr Trp Tyr Gln
             20                  25                  30

Gln Lys Pro Gly Lys Ser Pro Lys Leu Leu Ile Tyr Asp Thr Ser Asn
             35                  40                  45

Leu Ala Ser Gly Val Pro Val Arg Phe Ser Gly Ser Gly Ser Gly Thr
 50                  55                  60

Glu Tyr Thr Leu Thr Ile Ser Ser Leu Gln Pro Asp Asp Phe Ala Thr
 65                  70                  75                  80

Tyr Tyr Cys Gln Gln Trp Ser Ser Tyr Pro Tyr Thr Phe Gly Gly Gly
                 85                  90                  95

Thr Lys Val Glu Val Lys
            100

<210> SEQ ID NO 31
<211> LENGTH: 103
<212> TYPE: PRT
```

```
<213> ORGANISM: Artificial Sequence
<220> FEATURE:
<223> OTHER INFORMATION: Synthetic: 1H3VL.6

<400> SEQUENCE: 31

Met Thr Gln Thr Pro Ala Ile Met Ser Ala Ser Pro Gly Glu Lys Val
1               5                   10                  15

Thr Met Thr Cys Ser Ala Ser Ser Val Ser Tyr Met Tyr Trp Tyr
            20                  25                  30

Gln Gln Lys Pro Gly Ser Ser Pro Arg Leu Leu Ile Tyr Asp Thr Ser
            35                  40                  45

Asn Leu Ala Ser Gly Val Pro Val Arg Phe Ser Gly Ser Gly Ser Gly
50                  55                  60

Thr Ser Tyr Ser Leu Thr Ile Ser Arg Met Glu Ala Glu Asp Ala Ala
65                  70                  75                  80

Thr Tyr Tyr Cys Gln Gln Trp Ser Ser Tyr Pro Tyr Thr Phe Gly Gly
                85                  90                  95

Gly Thr Lys Leu Glu Ile Lys
            100

<210> SEQ ID NO 32
<211> LENGTH: 121
<212> TYPE: PRT
<213> ORGANISM: Artificial Sequence
<220> FEATURE:
<223> OTHER INFORMATION: Synthetic: 2G4VH .2 (G49A, F50E)

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Leu
            35                  40                  45

Ala Glu Ile Arg Leu Lys Ser Asn Asn Tyr Ala Thr His Tyr Ser Ala
    50                  55                  60

Ser Val Lys Gly Arg Phe Thr Ile Ser Arg Asp Lys Ser Lys Ser Thr
65                  70                  75                  80

Leu Tyr Leu Gln Met Asn Thr Leu Gln Ala Glu Asp Ser Ala Ile Tyr
                85                  90                  95

Tyr Cys Thr Arg Gly Asn Gly Asn Tyr Arg Ala Met Asp Tyr Trp Gly
                100                 105                 110

Gln Gly Thr Leu Val Thr Val Ser Ser
            115                 120

<210> SEQ ID NO 33
<211> LENGTH: 121
<212> TYPE: PRT
<213> ORGANISM: Artificial Sequence
<220> FEATURE:
<223> OTHER INFORMATION: Synthetic: 2G4VH .3

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Leu
            35                  40                  45
```

```
Ala Glu Ile Arg Leu Lys Ser Asn Asn Tyr Ala Thr His Tyr Ser Ala
    50                  55                  60

Ser Val Lys Gly Arg Phe Thr Ile Ser Arg Asp Asp Ser Lys Arg Ser
65                  70                  75                  80

Val Tyr Leu Gln Met Asn Thr Leu Gln Ala Glu Asp Ser Ala Ile Tyr
                85                  90                  95

Tyr Cys Thr Arg Gly Asn Gly Asn Tyr Arg Ala Met Asp Tyr Trp Gly
                100                 105                 110

Gln Gly Thr Leu Val Thr Val Ser Ser
        115                 120
```

<210> SEQ ID NO 34
<211> LENGTH: 121
<212> TYPE: PRT
<213> ORGANISM: Artificial Sequence
<220> FEATURE:
<223> OTHER INFORMATION: Synthetic: 2G4VH .4

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
                20                  25                  30

Trp Met Asn Trp Val Arg Gln Ala Pro Gly Lys Gly Leu Glu Trp Leu
            35                  40                  45

Ala Glu Ile Arg Leu Lys Ser Val Asn Tyr Ala Thr His Tyr Ser Ala
    50                  55                  60

Ser Val Lys Gly Arg Phe Thr Ile Ser Arg Asp Asp Ser Lys Arg Ser
65                  70                  75                  80

Val Tyr Leu Gln Met Asn Thr Leu Gln Ala Glu Asp Ser Ala Ile Tyr
                85                  90                  95

Tyr Cys Thr Arg Gly Ala Gly Val Phe Arg Ala Met Phe Tyr Trp Gly
                100                 105                 110

Gln Gly Thr Leu Val Thr Val Ser Ser
        115                 120
```

<210> SEQ ID NO 35
<211> LENGTH: 121
<212> TYPE: PRT
<213> ORGANISM: Artificial Sequence
<220> FEATURE:
<223> OTHER INFORMATION: Synthetic: 2G4VH .5 (A102V)

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
                20                  25                  30

Trp Met Asn Trp Val Arg Gln Ala Pro Gly Lys Gly Leu Glu Trp Leu
            35                  40                  45

Ala Glu Ile Arg Leu Lys Ser Val Asn Tyr Ala Thr His Tyr Ser Ala
    50                  55                  60

Ser Val Lys Gly Arg Phe Thr Ile Ser Arg Asp Asp Ser Lys Arg Ser
65                  70                  75                  80

Val Tyr Leu Gln Met Asn Thr Leu Gln Ala Glu Asp Ser Ala Ile Tyr
                85                  90                  95

Tyr Cys Thr Arg Gly Val Gly Val Phe Arg Ala Met Phe Tyr Trp Gly
```

```
                    100                 105                 110
Gln Gly Thr Leu Val Thr Val Ser Ser
            115                 120

<210> SEQ ID NO 36
<211> LENGTH: 107
<212> TYPE: PRT
<213> ORGANISM: Artificial Sequence
<220> FEATURE:
<223> OTHER INFORMATION: Synthetic: 2G4VL.2 (A43S, K45Q, Q100G)

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Ser
            20                  25                  30

Leu Ala Trp Tyr Gln Gln Lys Pro Gly Lys Ser Pro Gln Leu Leu Val
        35                  40                  45

Tyr Ser Ala Thr Ile Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Val Glu Ile Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic: 2G4VL.3 (Q3V, A43S, K45Q, D70Q,
      F71Y, Q100G)

<400> SEQUENCE: 37

Asp Ile Val Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Ser
            20                  25                  30

Leu Ala Trp Tyr Gln Gln Lys Pro Gly Lys Ser Pro Gln Leu Leu Val
        35                  40                  45

Tyr Ser Ala Thr Ile Leu Ala Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Val Glu Ile Lys
            100                 105

<210> SEQ ID NO 38
<211> LENGTH: 119
<212> TYPE: PRT
<213> ORGANISM: Artificial Sequence
<220> FEATURE:
<223> OTHER INFORMATION: Synthetic: 4G7VH .2 (G44S)

<400> SEQUENCE: 38

Gln Val Gln Leu Val Gln Ser Gly Ala Glu Val Lys Lys Pro Gly Ser
```

```
                1               5                   10                  15
Ser Val Lys Val Ser Cys Lys Ala Ser Gly Ser Ser Phe Thr Gly Phe
            20                  25                  30

Ser Met Asn Trp Val Arg Gln Ala Pro Gly Gln Ser Leu Glu Trp Met
        35                  40                  45

Gly Asn Ile Asp Thr Tyr Tyr Gly Gly Thr Thr Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Gly Ser Thr Phe Ala Tyr Trp Gly Gln Gly
                100                 105                 110

Thr Leu Val Thr Val Ser Ser
            115

<210> SEQ ID NO 39
<211> LENGTH: 119
<212> TYPE: PRT
<213> ORGANISM: Artificial Sequence
<220> FEATURE:
<223> OTHER INFORMATION: Synthetic: 4G7VH .3 (G44S, M48I, I70L, A72V)

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Ser Ser Phe Thr Gly Phe
            20                  25                  30

Ser Met Asn Trp Val Arg Gln Ala Pro Gly Gln Ser Leu Glu Trp Ile
        35                  40                  45

Gly Asn Ile Asp Thr Tyr Tyr Gly Gly Thr Thr Tyr Asn Gly Lys Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Gly Ser Thr Phe Ala Tyr Trp Gly Gln Gly
                100                 105                 110

Thr Leu Val Thr Val Ser Ser
            115

<210> SEQ ID NO 40
<211> LENGTH: 115
<212> TYPE: PRT
<213> ORGANISM: Artificial Sequence
<220> FEATURE:
<223> OTHER INFORMATION: Synthetic: 4G7VH .3.1 (G44S, M48I, N50V, I70L,
      A72V)

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Ser Ser Phe Thr Gly Phe
            20                  25                  30

Ser Met Asn Trp Val Arg Gln Ala Pro Gly Gln Ser Leu Glu Trp Ile
        35                  40                  45

Gly Val Ile Asp Thr Tyr Tyr Gly Gly Thr Thr Tyr Asn Gly Lys Phe
    50                  55                  60
```

```
Lys Gly Arg Val Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Tyr Tyr Gly Ser Thr Phe Ala Tyr Trp Gly Gln Gly
            100                 105                 110

Thr Leu Val
        115

<210> SEQ ID NO 41
<211> LENGTH: 119
<212> TYPE: PRT
<213> ORGANISM: Artificial Sequence
<220> FEATURE:
<223> OTHER INFORMATION: Synthetic: 4G7VH.3.2 (F32V, G44S, M48I, I70L,
      A72V)

<400> SEQUENCE: 41

Gln Val Gln Leu Val Gln Ser Gly Ala Glu Val Lys Lys Pro Gly Ser
  1               5                  10                  15

Ser Val Lys Val Ser Cys Lys Ala Ser Gly Ser Ser Phe Thr Gly Val
                 20                  25                  30

Ser Met Asn Trp Val Arg Gln Ala Pro Gly Gln Ser Leu Glu Trp Ile
             35                  40                  45

Gly Asn Ile Asp Thr Tyr Tyr Gly Gly Thr Thr Tyr Asn Gly Lys Phe
         50                  55                  60

Lys Gly Arg Val Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Tyr Tyr Gly Ser Thr Phe Ala Tyr Trp Gly Gln Gly
            100                 105                 110

Thr Leu Val Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: Synthetic: 4G7VL.2 (A43S, Y87F)

<400> SEQUENCE: 42

Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Asn Ile Tyr Ser Tyr
                 20                  25                  30

Leu Ala Trp Tyr Gln Gln Lys Pro Gly Lys Ser Pro Lys Leu Leu Val
             35                  40                  45

Tyr Asn Ala Lys Thr Leu Ile Glu Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln His Phe Gly Thr Pro Phe
                 85                  90                  95

Thr Phe Gly Gln Gly Thr Lys Val Glu Ile Lys
            100                 105
```

<210> SEQ ID NO 43
<211> LENGTH: 107
<212> TYPE: PRT
<213> ORGANISM: Artificial Sequence
<220> FEATURE:
<223> OTHER INFORMATION: Synthetic: 4G7VL.3 (Q3V, A48S, D70Q, T72S, F73L, Y87F, Q100S)

<400> SEQUENCE: 43

Asp Ile Val Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Val
        35                  40                  45

Tyr Asn Ala Lys Thr Leu Ile Glu Gly Val Pro Ser Arg Phe Ser Gly
    50                  55                  60

Ser Gly Ser Gly Thr Gln Phe Ser Leu Thr Ile Ser Ser Leu Gln Pro
65                  70                  75                  80

Glu Asp Ile Ala Thr Tyr Phe Cys Gln His His Phe Gly Thr Pro Phe
                85                  90                  95

Thr Phe Gly Ser Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: Synthetic: 4G7VL.4 (Q3V, A48S, K52V, D70Q, T72S, F73L, Y87F, Q100S)

<400> SEQUENCE: 44

Asp Ile Val Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Val
        35                  40                  45

Tyr Asn Ala Val Thr Leu Ile Glu Gly Val Pro Ser Arg Phe Ser Gly
    50                  55                  60

Ser Gly Ser Gly Thr Gln Phe Ser Leu Thr Ile Ser Ser Leu Gln Pro
65                  70                  75                  80

Glu Asp Ile Ala Thr Tyr Phe Cys Gln His His Phe Gly Thr Pro Phe
                85                  90                  95

Thr Phe Gly Ser Gly Thr Lys Val Glu Ile Lys
            100                 105

<210> SEQ ID NO 45
<211> LENGTH: 9
<212> TYPE: PRT
<213> ORGANISM: Artificial Sequence
<220> FEATURE:
<223> OTHER INFORMATION: Synthetic: 13C6 VH CDR1

<400> SEQUENCE: 45

Gly Phe Ser Leu Ser Thr Ser Gly Val
1               5

<210> SEQ ID NO 46

```
<211> LENGTH: 5
<212> TYPE: PRT
<213> ORGANISM: Artificial Sequence
<220> FEATURE:
<223> OTHER INFORMATION: Synthetic: 13C6 VH CDR2

<400> SEQUENCE: 46

Trp Trp Asp Asp Asp
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic: 13C6 VH  CDR3

<400> SEQUENCE: 47

Arg Asp Pro Phe Gly Tyr Asp Asn Ala Met Gly Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic: 13C6 VL CDR1

<400> SEQUENCE: 48

Lys Ala Ser Gln Asn Val Gly Thr Ala Val Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic: 13C6 VL WT CDR2

<400> SEQUENCE: 49

Ser Ala Ser Asn Arg Tyr Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic: 13C6 VL.1 and VL.2 CDR2

<400> SEQUENCE: 50

Ser Ala Ser Asn Arg Tyr Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic: 13C6 VL CDR3

<400> SEQUENCE: 51

Gln Gln Tyr Ser Ser Tyr Pro Leu Thr
1               5

<210> SEQ ID NO 52
<211> LENGTH: 7
```

```
<212> TYPE: PRT
<213> ORGANISM: Artificial Sequence
<220> FEATURE:
<223> OTHER INFORMATION: Synthetic: 6D8 VH CDR1

<400> SEQUENCE: 52

Gly Phe Asp Phe Ser Arg Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic: 6D8 VH CDR2

<400> SEQUENCE: 53

Asn Pro Asp Ser Ser Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic: 6D8 VH CDR3

<400> SEQUENCE: 54

Gln Gly Tyr Gly Tyr Asn Tyr
1               5

<210> SEQ ID NO 55
<211> LENGTH: 16
<212> TYPE: PRT
<213> ORGANISM: Artificial Sequence
<220> FEATURE:
<223> OTHER INFORMATION: Synthetic: 6D8 VL CDR1

<400> SEQUENCE: 55

Arg Ser Ser Gln Ser Ile Val His Ser Asn Gly Asn Thr Tyr Leu Glu
1               5                   10                  15

<210> SEQ ID NO 56
<211> LENGTH: 7
<212> TYPE: PRT
<213> ORGANISM: Artificial Sequence
<220> FEATURE:
<223> OTHER INFORMATION: Synthetic: 6D8 VL CDR2

<400> SEQUENCE: 56

Lys Ala Ser Asn Arg Phe Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic: 6D8 VL WT CDR3

<400> SEQUENCE: 57

Leu Gln Gly Ser His Val Pro Ser Thr
1               5

<210> SEQ ID NO 58
<211> LENGTH: 9
<212> TYPE: PRT
```

```
<213> ORGANISM: Artificial Sequence
<220> FEATURE:
<223> OTHER INFORMATION: Synthetic:  6D8 VL.3 CDR3

<400> SEQUENCE: 58

Leu Asn Gly Ser His Val Pro Ser Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic:  6D8 VL.4 CDR3

<400> SEQUENCE: 59

Leu Gln Gly Ser His Val Pro Ser Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic:  13F6 VH  CDR1

<400> SEQUENCE: 60

Gly Phe Ala Phe Ser Ser Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic:  13F6 VH CDR2

<400> SEQUENCE: 61

Ser Arg Gly Gly Gly Tyr
1               5

<210> SEQ ID NO 62
<211> LENGTH: 14
<212> TYPE: PRT
<213> ORGANISM: Artificial Sequence
<220> FEATURE:
<223> OTHER INFORMATION: Synthetic:  13F6 VH  WT CDR3

<400> SEQUENCE: 62

His Ile Tyr Tyr Gly Ser Ser His Tyr Tyr Ala Met Asp Tyr
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic:  13F6 VH .4 CDR3

<400> SEQUENCE: 63

His Ile Tyr Tyr Gly Ser Ser His Tyr Tyr Ala Met Asp Val
1               5                   10

<210> SEQ ID NO 64
<211> LENGTH: 12
<212> TYPE: PRT
<213> ORGANISM: Artificial Sequence
```

```
<220> FEATURE:
<223> OTHER INFORMATION: Synthetic: 13F6 VL CDR1

<400> SEQUENCE: 64

Thr Leu Ser Arg Gln His Ser Thr Tyr Thr Ile Glu
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic: 13F6 VL CDR2

<400> SEQUENCE: 65

Leu Lys Lys Asp Gly Ser His Ser Thr Gly Asp
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic: 13F6 VL WT CDR3

<400> SEQUENCE: 66

Gly Val Gly Asp Thr Ile Lys Glu Gln Phe Val Tyr Val
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic: 13F6 VL.5 and VL.6 CDR3

<400> SEQUENCE: 67

Gly Glu Gly Asp Thr Ile Lys Glu Gln Phe Val Tyr Val
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetic: 1H3 VH CDR1

<400> SEQUENCE: 68

Gly Phe Asn Ile Lys Asp Thr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic: 1H3 VH CDR2

<400> SEQUENCE: 69

Asp Pro Ala Asn Gly Asn
1               5

<210> SEQ ID NO 70
<211> LENGTH: 15
<212> TYPE: PRT
<213> ORGANISM: Artificial Sequence
<220> FEATURE:
```

<223> OTHER INFORMATION: Synthetic: 1H3 VH CDR3

<400> SEQUENCE: 70

Glu Ser Arg Ile Ser Thr Met Leu Thr Thr Gly Tyr Phe Asp Tyr
1               5                   10                  15

<210> SEQ ID NO 71
<211> LENGTH: 10
<212> TYPE: PRT
<213> ORGANISM: Artificial Sequence
<220> FEATURE:
<223> OTHER INFORMATION: Synthetic: 1H3 VL CDR1

<400> SEQUENCE: 71

Ser Ala Ser Ser Ser Val Ser Tyr Met Tyr
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Synthetic: 1H3 VL CDR2

<400> SEQUENCE: 72

Asp Thr Ser Asn Leu Ala Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic: 1H3 VL CDR3

<400> SEQUENCE: 73

Gln Gln Trp Ser Ser Tyr Pro Tyr Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic: 2G4 VH CDR1

<400> SEQUENCE: 74

Gly Phe Thr Phe Ser Asn Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic: 2G4 VH  CDR2

<400> SEQUENCE: 75

Arg Leu Lys Ser Asn Asn Tyr Ala
1               5

<210> SEQ ID NO 76
<211> LENGTH: 10
<212> TYPE: PRT
<213> ORGANISM: Artificial Sequence
<220> FEATURE:
<223> OTHER INFORMATION: Synthetic: 2G4 VH  CDR3

```
<400> SEQUENCE: 76

Gly Asn Gly Asn Tyr Arg Ala Met Asp Tyr
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Synthetic: 2G4VH .4 and 2G4VH.5 CDR2

<400> SEQUENCE: 77

Arg Leu Lys Ser Val Asn Tyr Ala
1               5

<210> SEQ ID NO 78
<211> LENGTH: 10
<212> TYPE: PRT
<213> ORGANISM: Artificial Sequence
<220> FEATURE:
<223> OTHER INFORMATION: Synthetic: 2G4VH .4  CDR3

<400> SEQUENCE: 78

Gly Ala Gly Val Phe Arg Ala Met Phe Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic: 2G4VH .5 CDR3

<400> SEQUENCE: 79

Gly Val Gly Val Phe Arg Ala Met Phe Tyr
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic: 2G4 VL CDR1

<400> SEQUENCE: 80

Arg Ala Ser Glu Asn Ile Tyr Ser Ser Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic: 2G4 VL CDR2

<400> SEQUENCE: 81

Ser Ala Thr Ile Leu Ala Asp
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic: 2G4 VL CDR3
```

```
<400> SEQUENCE: 82

Gln His Phe Trp Gly Thr Pro Tyr Thr
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic: 4G7 VH CDR1

<400> SEQUENCE: 83

Gly Ser Ser Phe Thr Gly Phe
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic: 4G7 VH CDR2

<400> SEQUENCE: 84

Asp Thr Tyr Tyr Gly Gly
1               5

<210> SEQ ID NO 85
<211> LENGTH: 10
<212> TYPE: PRT
<213> ORGANISM: Artificial Sequence
<220> FEATURE:
<223> OTHER INFORMATION: Synthetic: 4G7 VH CDR3

<400> SEQUENCE: 85

Ser Ala Tyr Tyr Gly Ser Thr Phe Ala Tyr
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Synthetic: 4G7VH.3.2 CDR1

<400> SEQUENCE: 86

Gly Ser Ser Phe Thr Gly Val
1               5

<210> SEQ ID NO 87
<211> LENGTH: 11
<212> TYPE: PRT
<213> ORGANISM: Artificial Sequence
<220> FEATURE:
<223> OTHER INFORMATION: Synthetic: 4G7 VL CDR1

<400> SEQUENCE: 87

Arg Ala Ser Glu Asn Ile Tyr Ser Tyr Leu Ala
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Synthetic: 4G7 VL CDR2

<400> SEQUENCE: 88
```

Asn Ala Lys Thr Leu Ile Glu
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic: 4G7 VL CDR3

<400> SEQUENCE: 89

Gln His His Phe Gly Thr Pro Phe Thr
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic: 4G7VL.4 CDR2

<400> SEQUENCE: 90

Asn Ala Val Thr Leu Ile Glu Gly
1               5

<210> SEQ ID NO 91
<211> LENGTH: 676
<212> TYPE: PRT
<213> ORGANISM: Zaire ebolavirus
<220> FEATURE:
<221> NAME/KEY: misc_feature
<222> LOCATION: (1)..(676)
<223> OTHER INFORMATION: Ebola virus glycoprotein precursor

<400> SEQUENCE: 91

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp

```
                195                 200                 205
Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620
```

-continued

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 92
<211> LENGTH: 124
<212> TYPE: PRT
<213> ORGANISM: Mouse sp.
<220> FEATURE:
<221> NAME/KEY: misc_feature
<222> LOCATION: (1)..(124)
<223> OTHER INFORMATION: 1H3-VH (mouse)

<400> SEQUENCE: 92

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Gly Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Asn Thr Ala Tyr
65                  70                  75                  80

Leu Gln Leu Ser Gly Leu Thr Ser Glu Asp Thr Ala Val Tyr Tyr Cys
                85                  90                  95

Ala Arg Glu Ser Arg Ile Ser Thr Met Leu Thr Gly Tyr Phe Asp
            100                 105                 110

Tyr Trp Gly Gln Gly Thr Thr Leu Thr Val Ser Ser
        115                 120

<210> SEQ ID NO 93
<211> LENGTH: 102
<212> TYPE: PRT
<213> ORGANISM: Mouse sp.
<220> FEATURE:
<221> NAME/KEY: misc_feature
<222> LOCATION: (1)..(102)
<223> OTHER INFORMATION: 1H3-VL (mouse)

<400> SEQUENCE: 93

Asp Ile Val Met Thr Gln Ser Pro Ala Ser Pro Gly Glu Lys Val Thr
1               5                   10                  15

Met Thr Cys Ser Ala Ser Ser Ser Val Ser Tyr Met Tyr Trp Tyr Gln
            20                  25                  30

Gln Lys Pro Gly Ser Ser Pro Arg Leu Leu Ile Tyr Asp Thr Ser Asn
        35                  40                  45

Leu Ala Ser Gly Val Pro Val Arg Phe Ser Gly Ser Gly Ser Gly Thr
    50                  55                  60

Ser Tyr Ser Leu Thr Ile Ser Arg Met Glu Ala Glu Asp Ala Ala Thr
65                  70                  75                  80

Tyr Tyr Cys Gln Gln Trp Ser Ser Tyr Pro Tyr Thr Phe Gly Gly Gly
                85                  90                  95

```
Thr Lys Leu Glu Ile Lys
            100
```

<210> SEQ ID NO 94
<211> LENGTH: 121
<212> TYPE: PRT
<213> ORGANISM: Mouse sp.
<220> FEATURE:
<221> NAME/KEY: misc_feature
<222> LOCATION: (1)..(121)
<223> OTHER INFORMATION: 2G4-VH (mouse)

<400> SEQUENCE: 94

```
Glu Val Gln Leu Gln Gln Ser Gly Gly Gly Leu Met Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Arg Ser
65                  70                  75                  80

Val Tyr Leu Gln Met Asn Thr Leu Arg Ala Glu Asp Thr Gly Ile Tyr
                85                  90                  95

Tyr Cys Thr Arg Gly Asn Gly Asn Tyr Arg Ala Met Asp Tyr Trp Gly
            100                 105                 110

Gln Gly Thr Ser Val Thr Val Ser Ser
        115                 120
```

<210> SEQ ID NO 95
<211> LENGTH: 107
<212> TYPE: PRT
<213> ORGANISM: Mouse sp.
<220> FEATURE:
<221> NAME/KEY: misc_feature
<222> LOCATION: (1)..(107)
<223> OTHER INFORMATION: 2G4-VL (mouse)

<400> SEQUENCE: 95

```
Asp Ile Val Met Thr Gln Ser Pro Ala Ser Leu Ser Val Ser Val Gly
1               5                   10                  15

Glu Thr Val Ser Ile Thr Cys Arg Ala Ser Glu Asn Ile Tyr Ser Ser
            20                  25                  30

Leu Ala Trp Tyr Gln Gln Lys Gln Gly Lys Ser Pro Gln Leu Leu Val
        35                  40                  45

Tyr Ser Ala Thr Ile Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Tyr
                85                  90                  95

Thr Phe Gly Gly Gly Thr Lys Leu Glu Ile Lys
            100                 105
```

<210> SEQ ID NO 96
<211> LENGTH: 119
<212> TYPE: PRT
<213> ORGANISM: Mouse sp.
<220> FEATURE:
<221> NAME/KEY: misc_feature

```
<222> LOCATION: (1)..(119)
<223> OTHER INFORMATION: 4G7-VH  (mouse)

<400> SEQUENCE: 96

Glu Val Gln Leu Gln Gln Ser Gly Pro Glu Leu Glu Met Pro Gly Ala
1               5                   10                  15

Ser Val Lys Ile Ser Cys Lys Ala Ser Gly Ser Ser Phe Thr Gly Phe
            20                  25                  30

Ser Met Asn Trp Val Lys Gln Ser Asn Gly Lys Ser Leu Glu Trp Ile
        35                  40                  45

Gly Asn Ile Asp Thr Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Ala Tyr Tyr Gly Ser Thr Phe Ala Tyr Trp Gly Gln Gly
            100                 105                 110

Thr Leu Val Thr Val Ser Ser
        115

<210> SEQ ID NO 97
<211> LENGTH: 107
<212> TYPE: PRT
<213> ORGANISM: Mouse sp.
<220> FEATURE:
<221> NAME/KEY: misc_feature
<222> LOCATION: (1)..(107)
<223> OTHER INFORMATION: 4G7-VL (mouse)

<400> SEQUENCE: 97

Asp Ile Val Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ile Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Phe Cys Gln His His Phe Gly Thr Pro Phe
                85                  90                  95

Thr Phe Gly Ser Gly Thr Glu Leu Glu Ile Lys
            100                 105

<210> SEQ ID NO 98
<211> LENGTH: 10
<212> TYPE: PRT
<213> ORGANISM: Ebola virus
<220> FEATURE:
<221> NAME/KEY: misc_feature
<222> LOCATION: (1)..(10)
<223> OTHER INFORMATION: Ebola virus GP T270-P279

<400> SEQUENCE: 98

Thr Gly Lys Leu Ile Trp Lys Val Asn Pro
1               5                   10

<210> SEQ ID NO 99
```

```
<211> LENGTH: 16
<212> TYPE: PRT
<213> ORGANISM: Ebola virus
<220> FEATURE:
<221> NAME/KEY: misc_feature
<222> LOCATION: (1)..(16)
<223> OTHER INFORMATION: Ebola virus GP Y394-R409

<400> SEQUENCE: 99

Tyr Lys Leu Asp Ile Ser Glu Ala Thr Gln Val Gly Gln His His Arg
1               5                   10                  15

<210> SEQ ID NO 100
<211> LENGTH: 7
<212> TYPE: PRT
<213> ORGANISM: Ebola virus
<220> FEATURE:
<221> NAME/KEY: misc_feature
<222> LOCATION: (1)..(7)
<223> OTHER INFORMATION: Ebola virus GPV505-C511

<400> SEQUENCE: 100

Val Asn Ala Gln Pro Lys Cys
1               5

<210> SEQ ID NO 101
<211> LENGTH: 15
<212> TYPE: PRT
<213> ORGANISM: Ebola virus
<220> FEATURE:
<221> NAME/KEY: misc_feature
<222> LOCATION: (1)..(15)
<223> OTHER INFORMATION: Ebola virus GP N550-E564

<400> SEQUENCE: 101

Asn Gln Asp Gly Leu Ile Cys Gly Leu Arg Gln Leu Ala Asn Glu
1               5                   10                  15
```

UNITED STATES PATENT AND TRADEMARK OFFICE
CERTIFICATE OF CORRECTION

| | | |
|---|---|---|
| PATENT NO. | : 10,894,818 B2 | Page 1 of 1 |
| APPLICATION NO. | : 15/515746 | |
| DATED | : January 19, 2021 | |
| INVENTOR(S) | : Sasisekharan et al. | |

It is certified that error appears in the above-identified patent and that said Letters Patent is hereby corrected as shown below:

In the Specification

In Column 1, Lines 11-14, delete:
"This invention was made with Government support under Grant Nos. R01 AI111395 and R37 GM057073 awarded by the National Institutes of Health. The Government has certain rights in the invention."

And insert:
-- This invention was made with government support under R01 AI111395 and R37 GM057073 awarded by the National Institutes of Health. The government has certain rights in the invention. --

Signed and Sealed this
Twenty-fifth Day of November, 2025

John A. Squires
*Director of the United States Patent and Trademark Office*